United States Patent
Cai

(10) Patent No.: US 10,899,750 B2
(45) Date of Patent: Jan. 26, 2021

(54) METHODS AND COMPOSITIONS OF SMALL MOLECULE MODULATORS OF HEPATOCYTE GROWTH FACTOR (SCATTER FACTOR) ACTIVITY

(71) Applicant: ANGION BIOMEDICA CORP., Uniondale, NY (US)

(72) Inventor: Weizhong Cai, Dix Hills, NY (US)

(73) Assignee: ANGION BIOMEDICA CORP., Uniondale, NY (US)

(*) Notice: Subject to any disclaimer, the term of this patent is extended or adjusted under 35 U.S.C. 154(b) by 0 days.

(21) Appl. No.: 16/239,836

(22) Filed: Jan. 4, 2019

(65) Prior Publication Data
US 2019/0375739 A1 Dec. 12, 2019

Related U.S. Application Data

(63) Continuation of application No. 15/978,576, filed on May 14, 2018, now abandoned, which is a continuation of application No. 15/720,164, filed on Sep. 29, 2017, now abandoned, which is a continuation of application No. 15/440,398, filed on Feb. 23, 2017, now abandoned, which is a continuation of application No. 14/287,039, filed on May 25, 2014, now abandoned, which is a continuation of application No. 13/003,514, filed as application No. PCT/US2009/004014 on Jul. 9, 2009, now Pat. No. 8,772,326.

(60) Provisional application No. 61/134,485, filed on Jul. 10, 2008.

(51) Int. Cl.
| C07D 409/14 | (2006.01) |
| A61K 9/00 | (2006.01) |
| A61K 9/14 | (2006.01) |
| A61K 9/16 | (2006.01) |
| A61K 9/19 | (2006.01) |
| A61K 9/48 | (2006.01) |
| A61K 31/415 | (2006.01) |
| A61K 31/4155 | (2006.01) |
| C07D 231/12 | (2006.01) |
| C07D 405/06 | (2006.01) |
| C07D 405/14 | (2006.01) |
| C07D 409/06 | (2006.01) |

(52) U.S. Cl.
CPC .......... *C07D 409/14* (2013.01); *A61K 9/0019* (2013.01); *A61K 9/145* (2013.01); *A61K 9/146* (2013.01); *A61K 9/1652* (2013.01); *A61K 9/19* (2013.01); *A61K 9/4866* (2013.01); *A61K 31/415* (2013.01); *A61K 31/4155* (2013.01); *C07D 231/12* (2013.01); *C07D 405/06* (2013.01); *C07D 405/14* (2013.01); *C07D 409/06* (2013.01)

(58) Field of Classification Search
CPC .. C07D 231/12; C07D 405/06; C07D 405/14; C07D 409/06; C07D 409/14; A61K 9/0019; A61K 9/145; A61K 9/146; A61K 9/1652; A61K 9/19; A61K 9/4866; A61K 31/415; A61K 31/4155
See application file for complete search history.

(56) References Cited

U.S. PATENT DOCUMENTS

| 4,806,535 A | 2/1989 | Faith et al. |
| 5,837,676 A | 11/1998 | Goldberg et al. |
| 5,919,759 A | 7/1999 | Goldberg et al. |
| 5,965,523 A | 10/1999 | Goldberg et al. |
| 5,997,868 A | 12/1999 | Goldberg et al. |
| 6,011,009 A | 1/2000 | Goldberg et al. |
| 6,013,624 A | 1/2000 | Goldberg et al. |
| 6,248,722 B1 | 6/2001 | Morishita et al. |

(Continued)

FOREIGN PATENT DOCUMENTS

| DE | 138-770 C | 11/1979 |
| JP | 48-000713 | 1/1973 |

(Continued)

OTHER PUBLICATIONS

Anzaldi, M. et al., Synthesis and antimicrobial activity of heterocyclic ionone-like derivatives, European Journal of Medicinal Chemistry, 34(10): 837-842 (1999).

(Continued)

*Primary Examiner* — Umamaheswari Ramachandran
(74) *Attorney, Agent, or Firm* — Choate, Hall & Stewart LLP; Kristen C. Buteau; Erica M. D'Amato

(57) ABSTRACT

The present invention provides compositions and formulations of compounds having formula (I):

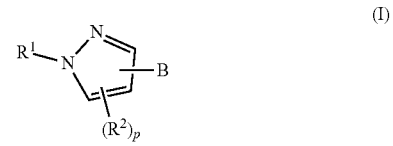

and pharmaceutically acceptable derivatives thereof, wherein p, $R^1$, $R^2$ and B are as described generally and in classes and subclasses herein, and additionally provides pharmaceutical compositions thereof, and methods for the use thereof for the treatment of any of a number of injuries, conditions or diseases in which HGF/SF or the activities thereof, or agonists or antagonists thereof have a therapeutically useful role. In addition, methods are provided for treating such diseases or diseases starting at a time after the onset of the injury, condition or disease.

24 Claims, No Drawings

(56) References Cited

U.S. PATENT DOCUMENTS

| | | |
|---|---|---|
| 6,258,787 B1 | 7/2001 | Isner |
| 6,303,126 B1 | 10/2001 | Nakamura et al. |
| 6,432,406 B1 | 8/2002 | Goldberg et al. |
| 6,437,006 B1 | 8/2002 | Yoon et al. |
| 6,498,144 B1 | 12/2002 | Goldberg et al. |
| 6,566,098 B1 | 5/2003 | Chan et al. |
| 6,589,997 B2 | 7/2003 | Pillarisetti et al. |
| 6,610,726 B2 | 8/2003 | Pillarisetti et al. |
| 6,677,333 B1 | 1/2004 | Seko et al. |
| 6,699,837 B2 | 3/2004 | Nakamura |
| 6,855,728 B2 | 2/2005 | Pillarisetti et al. |
| 6,994,857 B2 | 2/2006 | Rosen et al. |
| 7,192,976 B2 | 3/2007 | Zembower et al. |
| 7,250,437 B2 | 7/2007 | Zembower et al. |
| 7,265,112 B2 | 9/2007 | Zembower et al. |
| 7,648,978 B2 | 1/2010 | Zembower et al. |
| 7,674,790 B2 | 3/2010 | Ugwu et al. |
| 7,879,898 B1 | 2/2011 | He |
| 8,193,177 B2 | 6/2012 | Paka |
| 8,580,834 B2 | 11/2013 | Zembower et al. |
| 8,772,326 B2 | 7/2014 | Cai et al. |
| 9,663,471 B2 | 5/2017 | Zembower et al. |
| 2002/0183325 A1 | 12/2002 | Martin et al. |
| 2003/0022924 A1 | 1/2003 | Pillarisetti et al. |
| 2003/0022934 A1 | 1/2003 | Heil et al. |
| 2003/0045559 A1 | 3/2003 | Pillarisetti et al. |
| 2003/0060403 A1 | 3/2003 | Nakamura |
| 2003/0073692 A1 | 4/2003 | Pulici |
| 2003/0125247 A1 | 7/2003 | Rosen et al. |
| 2003/0216459 A1 | 11/2003 | Pillarisetti et al. |
| 2004/0180882 A1 | 9/2004 | Zembower et al. |
| 2005/0096372 A1 | 5/2005 | Pillarisetti et al. |
| 2005/0113369 A1 | 5/2005 | Zembower et al. |
| 2005/0192331 A1 | 9/2005 | Zembower et al. |
| 2006/0063767 A1 | 3/2006 | Javaid et al. |
| 2008/0015243 A1 | 1/2008 | Zembower et al. |
| 2010/0137285 A1 | 6/2010 | Zembower et al. |
| 2010/0168065 A1 | 7/2010 | Vialard et al. |
| 2010/0256117 A1 | 10/2010 | Paka |
| 2011/0098304 A1 | 4/2011 | Panicker et al. |
| 2011/0184038 A1 | 7/2011 | Cai et al. |
| 2011/0230407 A1 | 9/2011 | Yuzhakov |
| 2014/0256727 A1 | 9/2014 | Cai et al. |
| 2014/0256780 A1 | 9/2014 | Zembower et al. |
| 2018/0009793 A1 | 1/2018 | Cai et al. |
| 2019/0382348 A1 | 12/2019 | Zembower et al. |

FOREIGN PATENT DOCUMENTS

| | | |
|---|---|---|
| JP | 02-193994 | 7/1990 |
| JP | 11-288112 | 10/1999 |
| WO | WO-01/02369 A2 | 1/2001 |
| WO | WO-01/34650 A1 | 5/2001 |
| WO | WO-02/02593 A2 | 1/2002 |
| WO | WO-2004/009599 A1 | 1/2004 |
| WO | WO-2004/058721 A2 | 7/2004 |
| WO | WO-2006/036981 A2 | 4/2006 |
| WO | WO-2009/064422 A2 | 5/2009 |
| WO | WO-2010/005580 A2 | 1/2010 |
| WO | WO-2011/019400 A2 | 2/2011 |
| WO | WO-2012/047826 A2 | 4/2012 |

OTHER PUBLICATIONS

Attaby, F.A. et al., Reactions with Cyanothioacetamide and its Derivatives: Synthesis and Reactions of Several New Thieno- and Azolopyridine Derivatives, Phosphorus, Sulfur, Silicon and the Related Elements, 119:1-10 (1996).

Boekelheide, V. and Fedoruk, N.A., Syntheses of Fused Aromatic Heterocycles by 1,3-Dipolar Addition Reactions. 3-Azapyrrocolines, Journal of Organic Chemistry, 33(5):2062-2064 (1968).

Chau-Hua, et al., Hepatocyte growth factor gene therapy prevents radiation-induced liver damage, World Journal of Gastroenterology, 11(10):1496-1502 (2005).

Dohi, M. et al., Hepatocyte Growth Factor Attenuates Collagen Accumulation in a Murine Model of Pulmonary Fibrosis, American Journal of Respiratory and Critical Care Medicine, 162:2302-2307 (2000).

Eldin, S.M. et al., Reactions with Cyanothioacetamide Derivatives: Synthesis and Reactions of Some Pyridine and Annelated Pyridine Derivatives, Egyptian Journal of Pharmaceutical Sciences, 34(4-6):805-815 (1993).

Elghandour, A. et al., A Facile Synthesis of Pyrazolo [1,5-a]pyridine Derivatives: Reaction of Cinnamonitriles with 5-Amino-4-cyano-3-cyanomethlypyrazole, Journal für Praktische Chemie, 330(4):657-660 (1988).

Franquesa, M. et al., Direct electrotransfer of hHGF gene into kidney ameliorates ischemic acute renal failure, Gene Therapy, 12:1551-1558 (2005).

Fujimoto, J., Hepatology: Microcirculation and Pathogenesis of Alcoholic Liver Injury, Journal of Gastroenterology and Hepatology, 15:33-36 (2000).

Herrero-Fresneda, I. et al., HGF gene therapy attenuates renal allograft scarring by preventing the profibrotic inflammatory-induced mechanisms, Kidney International, 70:265-274 (2006).

Hwang, T.H. et al., A single administration of adenoviral-mediated HGF cDNA permits survival of mice from acute hepatic failure, Life Sciences, 72:851-861, (2003).

International Search Report for PCT/US2003/040917, 6 pages (dated Sep. 22, 2004).

International Search Report for PCT/US2008/011990, 3 pages (dated Aug. 6, 2009).

International Search Report for PCT/US2009/004014, 4 pages (dated Jan. 14, 2010).

Jin, H. et al., Early Treatment with Hepatocyte Growth Factor Improves Cardiac Function in Experimental Heart Failure Induced by Myrocardial Infarction, Journal of Pharmacology and Experimental Therapeutics, 304(2):654-660 (2003).

Kaspar, C.D.W. et al., A Review of Pediatric Chronic Kidney Disease, Blood Purif, 41: 211-214 (2016).

Lopez-Talavera, J.C. et al., Hepatocyte growth factor gene therapy for pancreatic islets in diabetes: reducing the minimal islet transplant mass required in a glucocorticoid-free rat model of allogeneic portal vein islet transplantation, Division of Endocrinology, 145(2):467-474 (2004).

Marigny, K. et al., Particular cutaneous side effects with etoposide-containing courses: is VP16 or etoposide phosphate responsible?, Cancer Chemotherapy and Pharmacology, 55:244-250 (2005).

Matsuno, Y. et al., Hepatocyte growth factor gene transfer into the liver via the portal vein using electroporation attenuates rat liver cirrhosis, Gene Therapy, 10:1559-1566 (2003).

Morishita, R. et al., Safety evaluation of clinical gene therapy using heptocyte growth factor to treat peripheral arterial disease, Hypertension, 44:203-209 (2004).

Morishita, R. et al., Therapeutic angiogenesis using heptocyte growth factor (HGF), Current Gene Therapy, 4:199-206 (2004).

Nakagami, H. et al., Hepatocyte growth factor prevents endothelial cell death through inhibition of bax translocation from cytosol to mitochondrial membrane, Diabetes, 51:2604-2611 (2002).

Nakamura, T. et al., Myocardial protection from ischmia/reperfusion injury by endogenous and exogenous HGF, The Journal of Clinical Investigation, 106(12):1511-1519 (2000).

Numata, M. et al., Hepatocyte Growth Factor Facilitates the Repair of Large Colonic Ulcers in 2,4,6-Trinitrobenzene Sulfonic Acid-Induced Colitis in Rats, Inflammatory Bowel Diseases, 11(6):551-558 (2005).

OE, S. et al., Continuous intravenous infusion of deleted form of hepatocyte growth factor attenuates hepatic ischemia-reperfusion injury in rats, Journal of Hepatology, 34:832-839 (2001).

Ono, I. et al., Local administration of hepatocyte growth factor gene enhances the regeneration of dermis in acute incisional wounds, Journal of Surgical Research, 120:47-55 (2004).

Patani, G.A. and Lavoie, E.L., Biosterism: a rational approach in drug design, Chemical Review, 93:3147-3176 (1996).

(56) References Cited

OTHER PUBLICATIONS

Perevalov, V.P. et al., Spectroscopic features of isomeric trans-styrylpyrazoles, Khimiya Geterotsiklicheskikh Soedinenii, 8:1061-1064 (1990).

Powell, R.J. et al., Therapeutic angiogenesis for critical limb ischemia: design of the hepatocyte growth factor therapeutic angiogenesis clinical trial, Vascular Medicine, 9:193-198 (2004).

Rahmoune, H. et al., Hepatocyte growth factor/scatter factor has distinct classes of binding site in heparan sulfate from mammary cells, Biochemistry, 37:6003-6008 (1998).

Rateb, L. et al., Reactions of Hydroxymethylene Ketones. Part II, Other Routes for the Preparation of Isoxazoles and Pyrazoles, Journal of the Chemical Society, 17:2137-2139 (1968).

Schneider, M. et al. Facile Synthesis of Cyclopropyl Alkadienes, Angewandte Chemie, 91(2):231-234 (1979).

Schvartsberg, M.S. et al., Acetylenic Derivatives of Heterocycles. Transformations of 3-ethynylpyrazole, Khimiya Geterotsiklicheskikh Soedinenii, 4(4):695-697 (1968).

Shimamura, M. et al., Novel Therapeutic Strategy to Treat Brain Ischemia: Overexpression of Hepatocyte Growth Factor Gene Reduced Ischemic Injury Without Cerebral Edema in Rat Model, Circulation: Journal of the American Heart Association, 109:424-431 (2004).

Sottofatori, E. et al., Synthesis of New Heterocyclic Derivatives of Retinoids, Journal of Heterocyclic Chemistry, 35(6):1377-1380, (1998).

Strickley, R.G., Solubilizing Excipients in Oral and Injectable Formulations, Pharmaceutical Research, 21(2):201-230 (2004).

Subramaniam, M.A. et al., Nonlinear Optic Properties of Heterocyclic Compounds Hyperpolarizability-structure Correlation, Ferroelectrics and Related Materials, 122(1-4):229-238 (1991).

Tashiro, H. et al., Hepatocyte growth factor prevents chronic allograft dysfunction in liver-transplanted rats, Transplantation: The Official Journal of the Transplantation Society, 76:761-765 (2003).

Tejwani, R.W. et al., Study of Phase Behavior of Poly(ethylene glycol)-Polysorbate 80 and Poly(ethylene glycol)-Polysorbate 80-Water Mixtures, Journal of Pharmaceutical Sciences, 89(7):946-950 (2000).

Tsuruta, H. et al., $\beta$-(2,4,6-Cycloheptatrien-1-yl) ethylcarbene. The Synthesis of 9-Substituted bicyclo[4.2.1]nona-2,4,7-trienes and 9-Substituted Barbaralanes, Bulletin of the Chemical Society of Japan, 45:2822-2828 (1972).

Tsuruta, H. et al., Isolation of a Potential Intermediate Leading to 9-Phenylbicyclo[4.2.1]nona-2,4,7-triene in the Thermal Decomposition of $\alpha$-phenyl-$\alpha$-tropylacetoaldehyde Tosylhydrazone, Journal of American Chemical Society, 90(25):7167-7168 (1968).

Tsuzuki, N. et al., Hepatocyte growth factor reduces infarct volume after transient focal cerebral ischemis in rats, Acta Neurochirurgica: The European Journal of Neurosurgery, 76:311-316 (2000).

Ueki, T. et al., Hepatocyte growth factor gene therapy of liver cirrhosis in rats, Nature Medicine, 5(2):226-230 (1999).

Watanabe, M. et al., Hepatocyte growth factor gene transfer to alveolar septa for effective suppression of lung fibrosis, Molecular Therapy, 12(1):58-67 (2005).

Written Opinion for PCT/US2003/040917, 35 pages (dated Apr. 1, 2005).

Written Opinion for PCT/US2005/034669, 11 pages (dated Jul. 27, 2006).

Written Opinion for PCT/US2009/004014, 6 pages (dated Jan. 14, 2010).

Yang, J. and Liu, Y., Delayed administration of hepatocyte growth factor reduces renal fibrosis in obstructive nephropathy, American Journal of Physiology: Renal Physiology, 284:F349-F357 (2003).

Yang, J. et al., Continuous AMD3100 Treatment Worsens Renal Fibrosis through Regulation of Bone Marrow Derived Pro-Angiogenic Cells Homing and T-Cell-Related Inflammation, PLOS One, 1-16 (2016).

Yoshida, S. et al., Recombinant hepatocyte growth factor accelerates cutaneous wound healing in a diabetic mouse model, Growth Factors, 22(2):111-119 (2004).

Zhou, Y.J. et al., Hepatocyte growth factor protects human endothelial cells against advanced glycation end products-induced apoptosis, Biochemical and Biophysical Research Communications, 344:658-666 (2006).

METHODS AND COMPOSITIONS OF SMALL MOLECULE MODULATORS OF HEPATOCYTE GROWTH FACTOR (SCATTER FACTOR) ACTIVITY

CROSS REFERENCE TO RELATED APPLICATIONS

This application is a continuation of U.S. application Ser. No. 15/978,576, filed May 14, 2018, which is a continuation of U.S. application Ser. No. 15/720,164, filed Sep. 29, 2017, which is a continuation of U.S. application Ser. No. 15/440,398, filed Feb. 23, 2017, which is a continuation of U.S. application Ser. No. 14/287,039, filed May 25, 2014, which is a continuation of U.S. application Ser. No. 13/003,514, now U.S. Pat. No. 8,772,326, filed on Jul. 8, 2014, which is a U.S. National Phase Application under 35 U.S.C. § 371 of International PCT Application No. PCT/US2009/004014, filed Jul. 9, 2009, which claims priority to U.S. Provisional Application No. 61/134,485, filed Jul. 10, 2008, the contents of each of which are hereby incorporated by reference.

GOVERNMENT SUPPORT

This invention was made with government support under Grant No. NS053152 from the National Institutes of Health. The government has certain rights in the invention.

BACKGROUND OF THE INVENTION

Scatter factor (SF; also known as hepatocyte growth factor [HGF], and hereinafter referred to and abbreviated as HGF/SF) is a pleiotropic growth factor that stimulates cell growth, cell motility, morphogenesis and angiogenesis. HGF/SF is produced as an inactive monomer (~100 kDa) which is proteolytically converted to its active form. Active HGF/SF is a heparin-binding heterodimeric protein composed of a 62 kDa α chain and a 34 kDa β$ chain. HGF/SF is a potent mitogen for parenchymal liver, epithelial and endothelial cells (Matsumoto, K, and Nakamura, T., 1997, Hepatocyte growth factor (HGF) as a tissue organizer for organogenesis and regeneration. Biochem. Biophys. Res. Commun. 239, 639-44; Boros, P. and Miller, C. M., 1995, Hepatocyte growth factor: a multifunctional cytokine. Lancet 345, 293-5). It stimulates the growth of endothelial cells and also acts as a survival factor against endothelial cell death (Morishita, R, Nakamura, S, Nakamura, Y, Aoki, M, Moriguchi, A, Kida, I, Yo, Y, Matsumoto, K, Nakamura, T, Higaki, J, Ogihara, T, 1997, Potential role of an endothelium-specific growth factor, hepatocyte growth factor, on endothelial damage in diabetes. Diabetes 46:138-42). HGF/SF synthesized and secreted by vascular smooth muscle cells stimulates endothelial cells to proliferate, migrate and differentiate into capillary-like tubes in vitro (Grant, D. S, Kleinman, H. K., Goldberg, I. D., Bhargava, M. M., Nickoloff, B. J., Kinsella, J. L., Polverini, P., Rosen, E. M., 1993, Scatter factor induces blood vessel formation in vivo. Proc. Natl. Acad. Sci. USA 90:1937-41; Morishita, R., Nakamura, S., Hayashi, S., Taniyama, Y., Moriguchi, A., Nagano, T., Taiji, M., Noguchi, H., Takeshita, S., Matsumoto, K., Nakamura, T., Higaki, J., Ogihara, T., 1999, Therapeutic angiogenesis induced by human recombinant hepatocyte growth factor in rabbit hind limb ischemia model as cytokine supplement therapy. Hypertension 33:1379-84). HGF/SF-containing implants in mouse subcutaneous tissue and rat cornea induce growth of new blood vessels from surrounding tissue. HGF/SF protein is expressed at sites of neovascularization including in tumors (Jeffers, M., Rong, S., Woude, G. F., 1996, Hepatocyte growth factor/scatter factor-Met signaling in tumorigenicity and invasion/metastasis. J. Mol. Med. 74:505-13; Moriyama, T., Kataoka, H., Koono, M., Wakisaka, S., 1999, Expression of hepatocyte growth factor/scatter factor and its receptor c-met in brain tumors: evidence for a role in progression of astrocytic tumors Int. J. Mol. Med. 3:531-6). These findings suggest that HGF/SF plays a significant role in the formation and repair of blood vessels under physiologic and pathologic conditions. Further discussion of angiogenic proteins may be found in U.S. Pat. Nos. 6,011,009 and 5,997,868, both of which are incorporated herein by reference in their entireties.

In certain embodiments, the present invention is directed toward formulations and compositions comprising such compounds, and various methods of use of the compounds as well as of the formulations and compositions embodied herein.

All citations in the present application are incorporated herein by reference in their entireties. The citation of any reference herein should not be construed as an admission that such reference is available as "Prior Art" to the instant application.

SUMMARY OF THE INVENTION

As discussed above, there remains a need for the development of novel therapeutics that are capable of mimicking or modulating HGF/SF activity.

In one embodiment, compositions and formulations are provided which compositions provide increased solubility of inventive compounds in liquid dosage forms, for facility of parenteral administration in manageable volumes of administration. In another embodiment, the compositions provide concentrations of inventive compound in solution high enough to provide efficacious peak blood levels from facile volumes of administration. In other embodiments, solid dosage forms are provided with increased bioavailability.

In another embodiment, solid formulations are provided comprising compounds of the invention, said formulations providing improved oral bioavailability.

In another embodiment, compounds of the invention as well as compositions and formulations thereof are therapeutically beneficial when administered at a time after the onset of the acute disease or acute condition or time of injury. In certain instances administration at least 3 hours after onset is beneficial. In other embodiments administration at least 24 hours after onset is beneficial. In certain other embodiments administration at least 1-3 weeks after onset is beneficial. In other embodiments methods are provided for treating an acute disease or condition wherein compound is administered at a time after the onset or induction of the disease or condition. In other embodiments, temporal separation of the induction, onset, recurrence or recrudescence of a disease or injury, and the optimal effective response to an HGF mimetic, provides guidance to the timing of administration of a compound of the invention or a composition of formulation thereof.

In another embodiment, the timing of single or multiple administrations of a compound of the invention is coordinated with the expression of the HGF receptor, c-Met. In another embodiment, c-Met expression is delayed from the time of onset of the disease or condition, for several hours to up to 24-48 hours afterwards. In another embodiment, the kinetics of c-Met receptor expression and the pharmacokinetics of inventive compound are coordinated such that peak or near peak circulating levels of inventive compound are present at the peak or near expression of c-Met. In one embodiment, the expression of c-Met following acute myocardial infarction is 24-48 hours.

In other embodiments, methods are provided for effectively treating chronic diseases and conditions is found using inventive compounds and compositions. In one embodiment, the chronic disease is amyotrophic lateral sclerosis (ALS, or Lou Gehrig's disease). In another embodiment, the chronic disease or condition is chronic heart failure.

In general, inventive compounds have the structure:

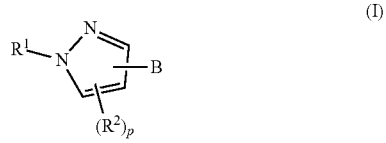

wherein p, $R^1$, $R^2$ and B are as described generally and in classes and subclasses herein In certain embodiments, the present invention provides novel compounds of general formula ($II^{A1}$) and ($III^{D1}$),

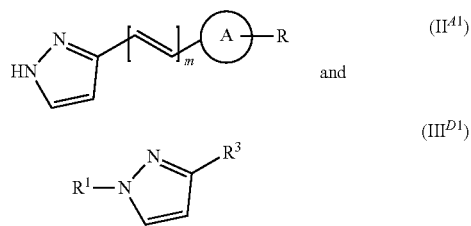

tautomers thereof, C(5)-positional isomers thereof; and pharmaceutical compositions thereof, as described generally and in subclasses herein, which compounds are useful as modulators of HGF/SF activity.

In another aspect, the invention provides methods for the use of any of the compositions and formulations embodied herein for modulating HGF/SF activity in a patient or a biological sample, in particular providing antifibrotic, angiogenic and antiapoptotic activities. The compounds and pharmaceutical compositions of the invention have properties of HGF/SF and are useful in the treatment of any disease, disorder or condition in which prophylactic or therapeutic administration of HGF/SF would be useful.

In another aspect, the invention provides methods for the use of any of the compositions or formulations embodied herein for treating or lessening the severity of a disease or condition associated with HGF/SF activity. In certain embodiments, the method is for treating or lessening the severity of a disease or condition selected from fibrotic liver disease, hepatic ischemia-reperfusion injury, cerebral infarction, ischemic heart disease, renal disease or lung (pulmonary) fibrosis. In certain embodiments, the method is for treating or lessening the severity of a disease or condition selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke; cerebrovascular disease; myocardial ischemia; atherosclerosis; renal failure; renal fibrosis or idiopathic pulmonary fibrosis. In certain exemplary embodiments, the method is for the treatment of wounds for acceleration of healing; vascularization of a damaged and/or ischemic organ, transplant or graft; amelioration of ischemia/reperfusion injury in the brain, heart, liver, kidney, and other tissues and organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; and/or diabetes mellitus.

Definitions

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, or alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. "Lower alkenyl" and "lower alkynyl" respectively include corresponding 1-6 carbon moieties.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$— cyclopropyl, cyclobutyl, —CH$_2$-cyclobutyl, cyclopentyl, —CH$_2$-cyclopentyl, cyclohexyl, —CH$_2$— cyclohexyl, cyclohexenylethyl, cyclohexanylethyl, norborbyl moieties and the like, which again, may bear one or more substituents.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "thioalkyl" as used herein refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl include, but are not limited to, methylthio, ethylthio, propylthio, isopropylthio, n-butylthio, and the like.

The term "alkylamino" refers to a group having the structure —NHR' wherein R' is aliphatic or alicyclic, as defined herein. The term "aminoalkyl" refers to a group having the structure NH$_2$R'—, wherein R' is aliphatic or alicyclic, as defined herein. In certain embodiments, the aliphatic or alicyclic group contains 1-20 aliphatic carbon atoms. In certain other embodiments, the aliphatic or alicyclic group contains 1-10 aliphatic carbon atoms. In still other embodiments, the aliphatic or alicyclic group contains 1-6 aliphatic carbon atoms. In yet other embodiments, the aliphatic or alicyclic group contains 1-4 aliphatic carbon atoms. In yet other embodiments, R' is an alkyl, alkenyl, or alkynyl group containing 1-8 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O) N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$) C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl) aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl;

heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, pyrazolyl, imidazolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "halo alkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "C$_{2-6}$alkenylidene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Another example is an N-methyl derivative of a compound, which is susceptible to oxidative metabolism resulting in N-demethylation, particularly on the 1 position of the 3(5)-monosubstituted pyrazole derivatives of the invention. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "tautomerization" refers to the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The term "tautomer" as used herein, refers to the compounds produced by the proton shift. For example, compounds of formula II (and more generally, compounds of formula II where R$^1$ is hydrogen), can exist as a tautomer as shown below:

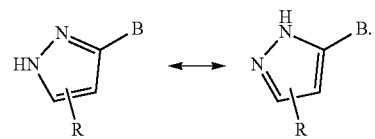

Thus, the present invention encompasses the 3-monosubstituted pyrazole compounds described herein (e.g., compounds of formula I, II, and related formulae II$^A$, II$^B$, II$^C$, etc. . . . ), as well as their tautomeric 5-monosubstituted pyrazole counterparts. Likewise, any compound shown as 5-monosubstituted pyrazole embraces its corresponding 3-monosubstituted tautomer.

The term "C(5)-positional isomer" as used herein refers to 1,5-disubstituted counterparts of the 1,3-disubstituted pyrazole compounds described herein. For example, the invention encompasses compounds of the formula (III$^B$) and its C(5)-positional isomer (III$^{B'}$):

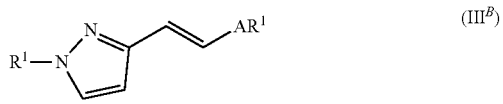

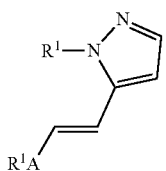

Thus, whether or not explicitly specified, the present invention encompasses the 1,3-disubstituted pyrazole compounds described herein (e.g., compounds of formula I, III, and related formulae III$^A$, III$^B$, III$^C$, III$^D$, etc.), as well as their C(5)-positional pyrazole counterparts. Likewise, any compound shown as 1,5-disubstituted pyrazole embraces its corresponding 1,3-disubstituted positional isomer.

By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As used herein, the term "isolated" when applied to the compounds of the present invention, refers to such compounds that are (i) separated from at least some components with which they are associated in nature or when they are made and/or (ii) produced, prepared or manufactured by the hand of man.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof; or purified versions thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, seminal fluid, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION OF CERTAIN EMBODIMENTS OF THE INVENTION

The present invention generally provides new formulations and compositions comprising compounds that modulate hepatocyte growth factor/scatter factor (HGF/SF) activity for all of the uses embodied herein, as well as new methods for use of the compounds embodied herein including their formulations and compositions. In certain embodiments, the small-molecule compounds of the invention modulate the activity of the HGF/SF receptor, c-Met. In further embodiments, compounds of the invention bind to c-met. In yet other embodiments, certain compounds of the invention mimic the activity of HGF/SF.

Compounds of this invention include those generally set forth above and described specifically herein, and are illustrated in part by the various classes, subgenera and species disclosed herein.

Additionally, the present invention provides pharmaceutically acceptable derivatives of the inventive compounds, and methods of treating a subject using these compounds, pharmaceutical compositions thereof, or either of these in combination with one or more additional therapeutic agents.

1) General Description of Compounds of the Invention

In certain embodiments, compounds of the invention include compounds of the general formula (I) as further defined below:

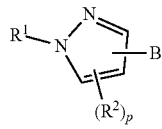
(I)

and tautomers and C(5)-positional isomers thereof;

wherein B is a C(3)- or C(5)-substituent selected from the group consisting of -AL$^1$-A, aryl, heteroaryl and heterocyclic; wherein AL$^1$ is an optionally substituted C$_{2-6}$alkenylene moiety, and A is an optionally substituted alicyclic, heteroalicyclic, aromatic or heteroaromatic moiety;

R$^1$ is hydrogen, —C(=O)(CH$_2$)$_m$R$^{1A}$, —C(=O)OR$^{1A}$, —C(=O)N(R$^{1A}$)$_2$ or —SO$_2$R$^{1A}$; wherein m is an integer from 0-3; each occurrence of R$^{1A}$ is independently hydrogen or an optionally substituted aliphatic, alicyclic, heteroaliphatic, heteroalicyclic, aromatic or heteroaromatic moiety;

p is one or two; and each R$^2$ is independently selected from the group consisting of hydrogen, halogen, hydroxyl, —NO$_2$, —CN, an optionally substituted aliphatic, heteroaliphatic, aromatic, heteroaromatic moiety; —OR$^R$, —S(=O)$_n$R$^d$, —NR$^b$R$^c$, and —C(=O)R$^a$; wherein n is 0-2, R$^R$ is an optionally substituted aliphatic, heteroaliphatic, aromatic or heteroaromatic moiety;

R$^a$, for each occurrence, is independently selected from the group consisting of hydrogen, hydroxy, aliphatic, heteroaliphatic, aryl and heteroaryl;

R$^b$ and R$^c$, for each occurrence, are independently selected from the group consisting of hydrogen; hydroxy; SO$_2$R$^d$; aliphatic, heteroaliphatic, aryl and heteroaryl;

R$^d$, for each occurrence, is independently selected from the group consisting of hydrogen; —N(R')$_2$; aliphatic, aryl and heteroaryl; and R$^e$, for each occurrence, is independently hydrogen or aliphatic.

In certain embodiments, the present invention defines particular classes of compounds which are of special interest. For example, one class of compounds of special interest includes those compounds of formula (I) wherein the nitrogen atom at position 1 is unsubstituted and the compound has the structure (II):

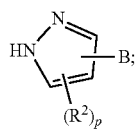
(II)

and tautomers thereof;

wherein p, R$^2$ and B are as defined generally above and in classes and subclasses herein.

Another class of compounds of special interest includes those compounds of formula (II) having the structure (II$^A$):

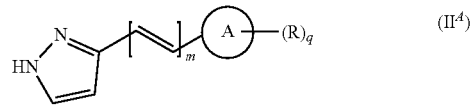
(II$^A$)

and tautomers thereof;

wherein A is as defined generally above and in classes and subclasses herein; m is an integer from 0-3; q is one or two, and each R is independently selected from the group consisting of hydrogen, halogen, hydroxyl, —NO$_2$, —CN, an optionally substituted aliphatic, heteroaliphatic, aromatic, heteroaromatic moiety; —OR$^R$, —S(=O)$_n$R$^d$, —NR$^b$R$^c$, and —C(=O)R$^a$; wherein n is 0-2, R$^R$ is an optionally substituted aliphatic, heteroaliphatic, aromatic or heteroaromatic moiety;

R$^a$, for each occurrence, is independently selected from the group consisting of hydrogen, hydroxy, aliphatic, heteroaliphatic, aryl and heteroaryl;

R$^b$ and R$^c$, for each occurrence, are independently selected from the group consisting of hydrogen; hydroxy; SO$_2$R$^d$; aliphatic, heteroaliphatic, aryl and heteroaryl;

R$^d$, for each occurrence, is independently selected from the group consisting of hydrogen; —N(R$^e$)$_2$; aliphatic, aryl and heteroaryl; and R$^e$, for each occurrence, is independently hydrogen or aliphatic.

In the foregoing formula, the [C=C]$_m$ bond(s) can be the cis or the trans isomer.

Another class of compounds of special interest includes those compounds of formula (II) having the structure (II$^B$):

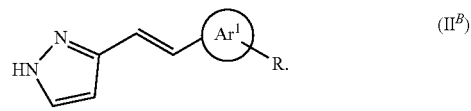
(II$^B$)

and tautomers thereof;

wherein R is as defined generally above and in classes and subclasses herein; and AR$^1$ is an optionally substituted aryl moiety. In the foregoing formula, the C=C bond can be the cis or the trans isomer.

Another class of compounds of special interest includes those compounds of formula (II) having the structure (II$^C$):

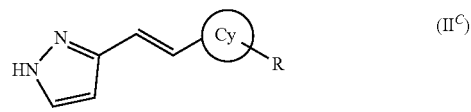
(II$^C$)

and tautomers thereof;

wherein R is as defined generally above and in classes and subclasses herein; and Cy is an optionally substituted heterocyclic moiety. In the foregoing formula, the C=C bond can be the cis or the trans isomer.

Another class of compounds of special interest includes those compounds of formula (I) wherein the nitrogen atom at position bears a substituent R$^1$ and the compound has the structure (III):

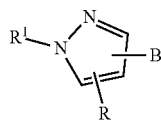

(III)

and C(5)-positional isomers thereof;

wherein B is as defined generally above and in classes and subclasses herein; and $R^1$ is —C(=O)(CH$_2$)$_m$R$^{1A}$, —C(=O)OR$^{1A}$, —C(=O)N(R$^{1A}$)$_2$ or —SO$_2$R$^{1A}$; wherein m is an integer from 0-3; and each occurrence of $R^{1A}$ is independently hydrogen or an optionally substituted aliphatic, alicyclic, heteroaliphatic, heteroalicyclic, aromatic or heteroaromatic moiety.

Another class of compounds of special interest includes those compounds of formula (III) having the structure (III$^A$):

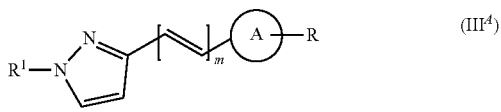

(III$^A$)

and C(5)-positional isomers thereof;

wherein $R^1$, R and A are as defined generally above and in classes and subclasses herein; and m is an integer from 0-3. In the foregoing formula, the [C=C]$_m$ bond(s) can be the cis or the trans isomer.

Another class of compounds of special interest includes those compounds of formula (III) having the structure (III$^B$):

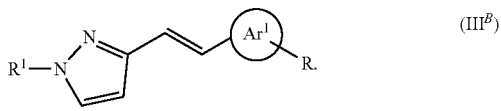

(III$^B$)

and C(5)-positional isomer thereof;

wherein R and $R^1$ are as defined generally above and in classes and subclasses herein; and AR$^1$ is an optionally substituted aryl moiety. In the foregoing formula, the C=C bond(s) can be the cis or the trans isomer.

Another class of compounds of special interest includes those compounds of formula (III) having the structure (III$^C$):

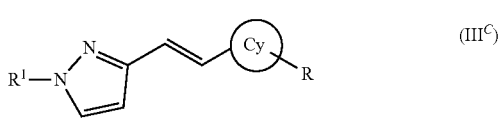

(III$^C$)

and C(5)-positional isomers thereof;

wherein R and $R^1$ are as defined generally above and in classes and subclasses herein; and Cy is an optionally substituted heterocyclic moiety. In the foregoing formula, the C=C bond(s) can be the cis or the trans isomer.

Another class of compounds of special interest includes those compounds of formula (III) having the structure (III$^D$):

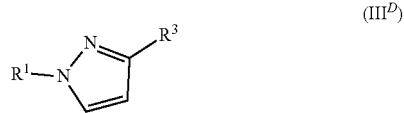

(III$^D$)

and C(5)-positional isomers thereof;

wherein $R^1$ is —SO$_2$R$^{1A}$; —C(=O)(CH$_2$)$_m$R$^{1A}$, —C(=O)OR$^{1A}$ or —C(=O)NHR$^{1A}$, wherein m is an integer from 0-3; and each occurrence of $R^{1A}$ is independently an optionally substituted aliphatic, alicyclic, heteroaliphatic, aryl or heterocyclic moiety; and $R^3$ is a cis or trans —CH=CH-AR$^1$, —CH=CH—Cy, phenoxyphenyl, or a heterocyclic group; wherein AR$^1$ is an optionally substituted aryl moiety and Cy is an optionally substituted heterocyclic moiety.

In certain exemplary embodiments, when $R^1$ is —SO$_2$R$^{1A}$; —C(=O)R$^{1A}$ or —C(=O)NHR$^{1A}$; wherein $R^{1A}$ is alkyl or aryl; then $R^3$ is not an optionally substituted cis or trans —CH=CH-heterocyclic, phenoxyphenyl, or a heterocyclic group.

A number of important subclasses of each of the foregoing classes deserve separate mention; these subclasses include subclasses of the foregoing classes in which:

i) $R^1$ is hydrogen;

ii) $R^1$ is —C(=O)R$^{1A}$, —C(=O)NHR$^{1A}$ or —SO$_2$R$^{1A}$; wherein each occurrence of $R^{1A}$ is independently alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroaryl or -(heteroalkyl)heteroaryl moiety;

iii) $R^1$ is —C(=O)R$^{1A}$, —C(=O)NHR$^{1A}$ or —SO$_2$R$^{1A}$; wherein each occurrence of $R^{1A}$ is independently an alkyl, cycloalkyl, heterocyclic or aryl moiety;

iv) $R^1$ is —SO$_2$R$^{1A}$, —C(=O)(CH$_2$)$_m$R$^{1A}$, —C(=O)OR$^{1A}$ or —C(=O)NHR$^{1A}$, wherein m is an integer from 0-3; and each occurrence of $R^{1A}$ is independently alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroaryl or -(heteroalkyl)heteroaryl moiety;

v) $R^1$ is —SO$_2$R$^{1A}$, —C(=O)(CH$_2$)$_m$R$^{1A}$, —C(=O)OR$^{1A}$ or —C(=O)NHR$^{1A}$, wherein m is an integer from 0-3; and each occurrence of $R^{1A}$ is independently an alkyl, cycloalkyl, heterocyclic or aryl moiety;

vi) $R^1$ is SO$_2$AL$^1$, C(=O)(CH$_2$)$_m$AL$^1$, C(=O)OAL$^1$, C(=O)NHAL$^1$, SO$_2$Aryl, C(=O)(CH$_2$)$_m$Aryl, C(=O)OAryl, C(=O)OHeterocyclic, C(=O)(CH$_2$)$_m$Heterocyclic, or C(=O)NHAryl; wherein m is 0-3; AL$^1$ is an aliphatic or alicyclic moiety; and AL$^1$, the aryl and heterocyclic moiety are independently optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; or COCH$_2$OC$_2$H$_5$OCH$_3$;

vii) compounds of subset vi) above wherein AL$^1$ is alkyl or cycloalkyl;

viii) R$^1$ is C(=O)(CH$_2$)$_m$AL$^1$; C(=O)(CH$_2$)$_m$Aryl or C(=O)Heterocyclic; wherein m-1-3; AL$^1$ is an aliphatic or alicyclic moiety; and AL$^1$, the aryl and heterocyclic moiety are independently optionally substituted with one or more substituents independently selected from hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; or COCH$_2$OC$_2$H$_5$OCH$_3$;

ix) compounds of subset vii) above where AL$^1$ is alkyl or cycloalkyl;

x) R$^1$ is C(=O)O-AL$^1$ or C(=O)O-Aryl; wherein AL$^1$ is an aliphatic or alicyclic moiety; and AL$^1$ and the aryl moiety are optionally substituted with one or more substituents independently selected from hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl;

xi) compounds of subset x) above where AL$^1$ is alkyl or cycloalkyl;

xii) R$^1$ is SO$_2$AL$^1$, C(=O)(CH$_2$)$_m$AL$^1$, C(=O)NHAL$^1$, SO$_2$Aryl, C(=O)(CH$_2$)$_m$Aryl, C(=O)(CH$_2$)$_m$Heterocyclic or C(=O)NHAryl; wherein m is 0-3; AL$^1$ is an aliphatic or alicyclic moiety; and AL$^1$, the aryl and heterocyclic moiety are independently optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; or COCH$_2$OC$_2$H$_5$OCH$_3$;

xiii) compounds of subset xii) above where AL$^1$ is alkyl or cycloalkyl;

xiv) R$^1$ is C(=O)(CH$_2$)$_m$AL$^1$ wherein m is 1-3, C(=O)(CH$_2$)$_m$Aryl, C(=O)(CH$_2$)$_m$Heterocyclic where m is 0-3; AL$^1$ is an aliphatic or alicyclic moiety; and AL$^1$, the aryl and heterocyclic moiety are independently optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; or COCH$_2$OC$_2$H$_5$OCH$_3$;

xv) compounds of subset xiv) above where AL$^1$ is alkyl or cycloalkyl;

xvii) R$^1$ as SO$_2$AL$^1$, C(=O)AL$^1$, C(=O)NHAL$^1$, SO$_2$Aryl, C(=O)Aryl, or C(=O)NHAryl, wherein AL$^1$ is an aliphatic or alicyclic moiety; and AL$^1$ and the aryl moiety are independently optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; or COCH$_2$OC$_2$H$_5$OCH$_3$;

xviii) compounds of subset xvii) above wherein AL$^1$ is alkyl or cycloalkyl;

xix) R$^1$ is C(=O)Aryl optionally substituted with one or more substituents independently selected from the group consisting of hydrogen; CN; carboxy ester; —C(=O)R$^a$, or —S(O)$_n$R$^d$ where n=0-2; C$_{1-6}$alkoxy substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; —NR$^f$R$^g$; C$_{1-6}$ alkyl substituted with one or more substituents independently selected from halogen, hydroxy, C$_{1-5}$ alkoxy, nitro, and N(R$^e$)$_2$, or C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$;

xx) B or R$^3$ is a cis or trans CHCHAryl, CHCHHeterocyclic, phenoxyphenyl, or a heterocyclic group, optionally substituted with one or more substituents independently selected from the group consisting of hydrogen; halogen; hydroxy; nitro; CN; aryl; heteroaryl; —C(=O)$R^a$, —$NR^bR^c$, or —S(O)$_n$$R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$;

xxi) B or $R^3$ is a cis or trans CHCHAryl, optionally substituted with one or more substituents independently selected from the group consisting of hydrogen; halogen; hydroxy; nitro; CN; aryl; heteroaryl; —C(=O)$R^a$, —$NR^bR^c$, or —S(O)$_n$$R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$;

xxii) B or $R^3$ is a cis or trans CHCHheterocyclic, phenoxyphenyl, or a heterocyclic group, optionally substituted with one or more substituents independently selected from the group consisting of hydrogen; halogen; hydroxy; nitro; CN; aryl; heteroaryl; —C(=O)$R^a$, —$NR^bR^c$, or —S(O)$_n$$R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$;

xxiii) R is one or more substituents selected from the group consisting of hydrogen, halogen, hydroxyl, —NO$_2$, —CN, alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroaryl or -(heteroalkyl)heteroaryl moiety; hydrogen, alkyl, heteroalkyl, aryl, heteroaryl, -(alkyl)aryl, -(alkyl)heteroaryl, —O$R^R$, —S(=O)$_n$$R^R$, —N($R^R$)$_2$, —SO$_2$N($R^R$)$_2$, —C(=O)$R^R$, —C(=O)N($R^R$)$_2$, —C(=O)O$R^R$, —N($R^R$)C(=O)$R^R$ or —N($R^R$)SO$_2$$R^R$; wherein n is 0-2, and $R^R$, for each occurrence, is independently hydrogen, lower alkyl, lower heteroalkyl, aryl, heteroaryl, -(alkyl)aryl, or -(alkyl)heteroaryl;

xxiv) R is one or more substituents selected from the group consisting of hydrogen, halogen, hydroxyl, —NO$_2$, —CN, alkoxy, alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroaryl, -(heteroalkyl)heteroaryl moiety, —S(=O)$_n$$R^d$, —$NR^bR^c$, and —C(=O)$R^a$; wherein n is 0-2;

xxv) each R is independently selected from hydrogen; halogen; hydroxy; nitro; CN; aryl; heteroaryl; —C(=O)$R^a$; —$NR^bR^c$; —S(O)$_n$$R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring optionally containing 1-3 heteroatoms selected from the group consisting of N, O, and S; and $C_{1-6}$ alkyl, $C_{2-6}$ alkenyl, $C_{2-6}$ alkynyl, or $C_{3-6}$ cycloalkyl, each independently optionally substituted with one or more substituents independently selected from halogen, hydroxy, $C_{1-5}$ alkoxy, nitro, and N($R^e$)$_2$;

xxvi) each R is independently selected from hydrogen; halogen; hydroxy; nitro; CN; $C_{1-6}$ alkyl; $C_{1-6}$ alkoxy; halo$C_{1-6}$ alkoxy; —C(=O)$R^a$; —C(=O)Oar; —O$R^a$ and —$NR^aR^b$; wherein $R^a$ and $R^b$ are independently lower alkyl or any two adjacent $R^a$ groups, or $R^a$ and $R^b$ groups, taken together, may form a heterocyclic moiety;

xxvii) each R is independently selected from hydrogen; halogen; hydroxy or nitro;

xxviii) $R^a$, for each occurrence, is independently selected from the group consisting of hydrogen, hydroxy, $C_{1-6}$ alkyl, $C_{1-6}$ alkoxy, aryl, heteroaryl, and $NR^bR^c$, wherein $C_{1-6}$ alkyl and $C_{1-6}$ alkoxy are optionally substituted with one or more substituents independently selected from halogen, hydroxy, $C_{1-5}$ alkoxy, nitro, and N($R^e$)$_2$;

xxix) $R^b$ and $R^c$, for each occurrence, are independently selected from the group consisting of hydrogen; hydroxy; SO$_2$$R^d$; $C_{1-6}$ alkyl optionally substituted with one or more substituents independently selected from halogen, hydroxy, $C_{1-5}$ alkoxy, nitro, and N($R^e$)$_2$; $C_{1-6}$ alkoxy optionally substituted with one or more substituents independently selected from halogen, hydroxy, $C_{1-5}$ alkoxy, nitro and N($R^e$)$_2$; aryl optionally substituted with one or more substituents independently selected from halogen, hydroxy, $C_{1-4}$ alkyl, $C_{1-5}$ alkoxy, nitro, and N($R^e$)$_2$; and heteroaryl optionally substituted with one or more substituents independently selected from halogen, hydroxy, $C_{1-4}$ alkyl, $C_{1-5}$ alkoxy, nitro, and N($R^e$)$_2$;

xxx) $R^d$, for each occurrence, is independently selected from the group consisting of hydrogen; N($R^e$)$_2$; $C_{1-6}$ alkyl optionally substituted with one or more substituents independently selected from halogen, hydroxy, $C_{1-5}$ alkoxy, nitro, and N($R^e$)$_2$; aryl and heteroaryl;

xxxi) $R^e$, for each occurrence, is independently hydrogen or $C_{1-6}$ alkyl;

xxxii) $R^f$ and $R^g$, for each occurrence, are independently selected from the group consisting of hydrogen; hydroxy; SO$_2$$R^d$; $C_{1-6}$ alkyl substituted with one or more substituents independently selected from halogen, hydroxy, $C_{1-5}$, alkoxy, nitro, and N($R^e$)$_2$; $C_{1-6}$ alkoxy optionally substituted with one or more substituents independently selected from halogen, hydroxy, $C_{1-5}$ alkoxy, nitro and N($R^e$)$_2$; aryl optionally substituted with one or more substituents independently selected from halogen, hydroxy, $C_{1-4}$ alkyl, $C_{1-5}$ alkoxy, nitro, and N($R^e$)$_2$; and heteroaryl optionally substituted with one or more substituents independently selected from halogen, hydroxy, $C_{1-4}$ alkyl, $C_{1-5}$ alkoxy, nitro, and N($R^e$)$_2$;

xxxiii) $R^2$ is one or more substituents selected from the group consisting of hydrogen, halogen, hydroxyl, —NO$_2$, —CN, alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroaryl or -(heteroalkyl)heteroaryl moiety; hydrogen, alkyl, heteroalkyl, aryl, heteroaryl, -(alkyl)aryl, -(alkyl)heteroaryl, —O$R^R$, —S(=O)$_n$$R^R$, —N($R^R$)$_2$, —SO$_2$N($R^R$)$_2$, —C(=O)$R^R$, —C(=O)N($R^R$)$_2$, —C(=O)O$R^R$, —N($R^R$)C(=O)$R^R$ or —N($R^R$)SO$_2$$R^R$; wherein n is 0-2, and $R^R$, for each occurrence, is independently hydrogen, lower alkyl, lower heteroalkyl, aryl, heteroaryl, -(alkyl)aryl, or -(alkyl)heteroaryl;

xxxiv) $R^2$ is one or more substituents selected from the group consisting of hydrogen, halogen, hydroxyl, —NO$_2$, —CN, alkoxy, alkyl, alkenyl, alkynyl, cycloalkyl, cycloalkenyl, cycloalkynyl, heterocyclic, aryl, heteroaryl, -(alkyl)

aryl, -(heteroalkyl)aryl, -(alkyl)heteroaryl, -(heteroalkyl) heteroaryl moiety, —S(=O)R$^d$, —NR$^b$R$^c$, and —C(=O) R$^a$; wherein n is 0-2;

xxxv) R$^2$ is one or more substituents selected from hydrogen; halogen; hydroxy; nitro; CN; aryl; heteroaryl; —C(=O)R$^a$; —NR$^b$R$^c$; —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring optionally containing 1-3 heteroatoms selected from the group consisting of N, O, and S; and C$_{1-6}$ alkyl, C$_{2-6}$ alkenyl, C$_{2-6}$ alkynyl, or C$_{3-6}$ cycloalkyl, each independently optionally substituted with one or more substituents independently selected from halogen, hydroxy, C$_{1-5}$ alkoxy, nitro, and N(R$^e$)$_2$;

xxxvi) R$^2$ is one or more substituents selected from hydrogen; halogen; hydroxy; nitro; CN; C$_{1-6}$ alkyl; C$_{1-6}$ alkoxy; haloC$_{1-6}$ alkoxy; —C(=O)R$^a$; —C(=O)OR$^a$; —OR$^a$ and —NR$^a$R$^b$; wherein R$^a$ and R$^b$ are independently lower alkyl or any two adjacent R$^a$ groups, or R$^a$ and R$^b$ groups, taken together, may form a heterocyclic moiety;

xxxvii) A is an alicyclic, heteroalicyclic, aromatic or heteroaromatic moiety;

xxxviii) A is an optionally substituted aromatic or non-aromatic 5-6 membered monocyclic ring, optionally containing 1-4 heteroatoms selected from N, O or S; or an optionally substituted aromatic or non-aromatic 8-12 membered bicyclic ring, optionally containing 1-6 heteroatoms selected from N, O or S;

xxxix) A is an aromatic or non-aromatic 5-6 membered monocyclic ring or 8-12 membered bicyclic ring, optionally substituted with one or more substituents selected from hydrogen; halogen; hydroxy; nitro; CN; C$_{1-6}$ alkyl; C$_{1-6}$ alkoxy; haloC$_{1-6}$ alkoxy; —C(=O)R$^a$; —C(=O)OR$^a$; —OR$^a$ and —NR$^a$R$^b$; wherein R$^a$ and R$^b$ are independently lower alkyl or any two adjacent R$^a$ groups, or R$^a$ and R$^b$ groups, taken together, may form a heterocyclic moiety;

xl) A is an aromatic or non-aromatic 5-6 membered monocyclic ring or 8-12 membered bicyclic ring, optionally substituted with one or more substituents selected from hydrogen; Cl; hydroxy; nitro; CN; —OCF$_3$; —C(=O) Omen; —C(=O)Me; —OMe; methyldioxyl; —NMe$_2$ and morpholinyl;

xli) A is optionally substituted aryl;

xlii) A is optionally substituted phenyl or naphthyl;

xliii) A is optionally substituted heteroaryl;

xliv) A has the structure:

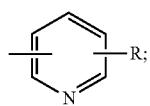

wherein R represents one or more substituents, as defined in subsets xxiii)-xxvii);

xlv) A is an optionally substituted C$_{1-6}$cycloalkyl or C$_{1-6}$cycloalkenyl moiety;

xlvi) A is optionally substituted cyclohexenyl;

xlvii) A is an optionally substituted heterocyclic moiety;

xlviii) A and/or Cy is one of:

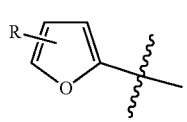 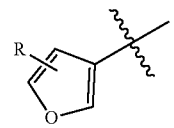 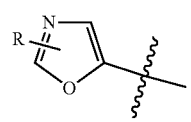

-continued

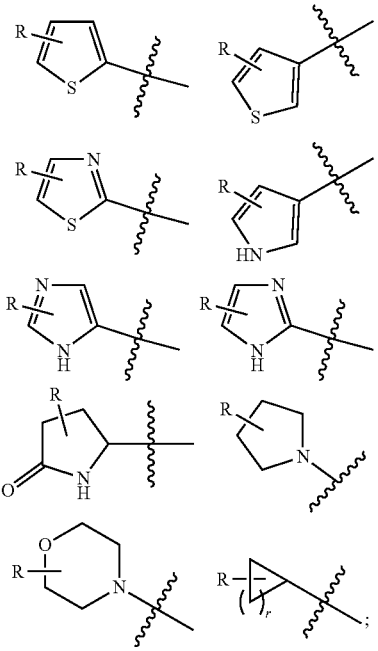

wherein R represents one or more substituents, as defined in subsets xxiii)-xxvii); and r is an integer from 1-6;

xlix) A and/or Cy is an optionally substituted 5-membered heterocyclic moiety having the structure:

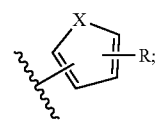

wherein R represents one or more substituents, as defined in subsets xxiii)-xxvii); and X is O, S or NR$^N$; wherein R$^N$ is hydrogen, lower alkyl, aryl, acyl or a nitrogen protecting group;

l) A and/or Cy is an optionally substituted 5-membered heterocyclic moiety having the structure:

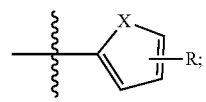

wherein R represents one or more substituents, as defined in subsets xxiii)-xxvii); and X is O, S or NR$^N$; wherein R$^N$ is hydrogen, lower alkyl, aryl, acyl or a nitrogen protecting group;

li) B is a moiety having the structure:

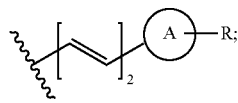

wherein A and R are as defined in classes and subclasses herein;

lii) B is a moiety having one of the structures:

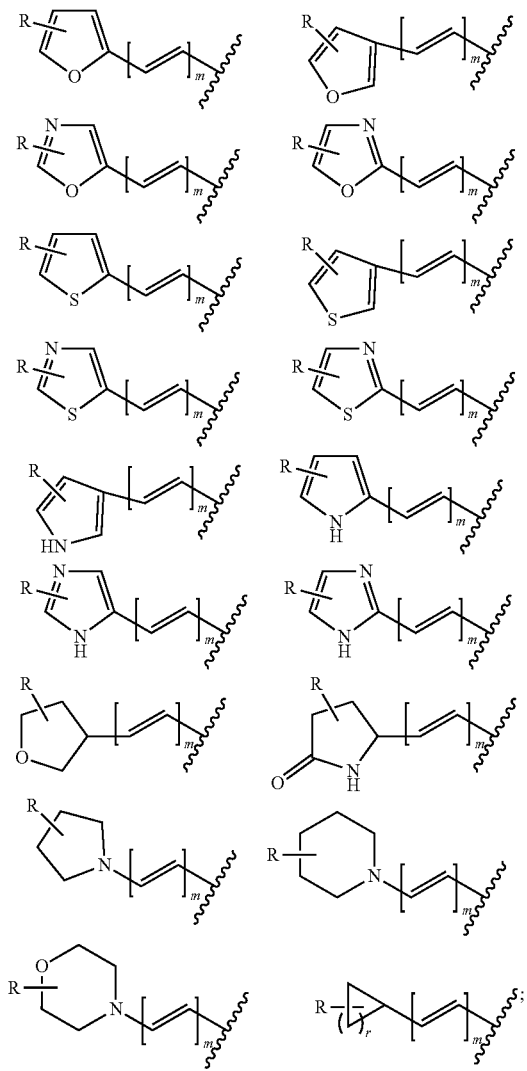

wherein R represents one or more substituents, as defined in subsets xxiii)-xxvii); m is an integer from 1-3; and r is an integer from 1-6; and wherein any of the [C=C]$_m$ bond(s) can be the cis or the trans isomer;

liii) AR is phenyl or naphthyl; and/or liv) AR$^1$ is phenyl or naphthyl.

It will be appreciated that for each of the classes and subclasses described above and herein, any one or more occurrences of aliphatic and/or heteroaliphatic may independently be substituted or unsubstituted, linear or branched, saturated or unsaturated; any one or more occurrences of alicyclic and/or heteroalicyclic may independently be substituted or unsubstituted, saturated or unsaturated; and any one or more occurrences of aryl and/or heteroaryl may independently be substituted or unsubstituted.

The reader will also appreciate that all possible combinations of the variables described in i)-through liv) above (e.g., R, R$^1$, and B, among others) are considered part of the invention. Thus, the invention encompasses any and all compounds of formula I generated by taking any possible permutation of variables R, R$^1$, and B, and other variables/substituents (e.g., A, R$^{1A}$, etc.) as further defined for R, R$^1$, and B, described in i)-through liv) above.

For example, an exemplary combination of variables described in i)-through liv) above includes those compounds of Formula wherein:

B is a C(3)- or C(5)-substituent selected from the group consisting of optionally substituted cis or trans CHCHAryl, CHCHHeterocyclic, phenoxyphenyl and a heterocyclic R$^1$ is C(=O)Aryl optionally substituted with one or more substituents independently selected from the group consisting of hydrogen; CN; carboxy ester; —C(=O)R$^a$, or —S(O)$_n$R$^d$ where n=0-2; alkoxy substituted with one or more substituents, as defined independently selected from halogen and C$_{1-6}$ alkyl; an optionally substituted fused bicyclic 8-12-membered aromatic or alicyclic ring containing 0-3 heteroatoms selected from the group consisting of N, O, and S; —NR$^f$R$^g$; C$_{1-6}$ alkyl substituted with one or more substituents independently selected from halogen, hydroxy, C$_{1-5}$ alkoxy, nitro, and N(R$^e$)$_2$, or C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; and each R is independently selected from hydrogen; halogen; hydroxy; nitro; CN; aryl; heteroaryl; —C(=O)R$^a$; —NR$^b$R$^c$; —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring optionally containing 1-3 heteroatoms selected from the group consisting of N, O, and S; and C$_{1-6}$ alkyl, C$_{2-6}$ alkenyl, C$_{2-6}$ alkynyl, or C$_{3-6}$ cycloalkyl, each independently optionally substituted with one or more substituents independently selected from halogen, hydroxy, C$_{1-5}$ alkoxy, nitro, and N(R$^e$)$_2$;

wherein R$^a$, for each occurrence, is independently selected from the group consisting of hydrogen, hydroxy, C$_{1-6}$ alkyl, C$_{1-6}$ alkoxy, aryl, heteroaryl, and NR$^b$R$^c$, wherein C$_{1-6}$ alkyl and C$_{1-6}$ alkoxy are optionally substituted with one or more substituents independently selected from halogen, hydroxy, C$_{1-5}$ alkoxy, nitro, and N(R$^e$)$_2$;

R$^b$ and R$^c$, for each occurrence, are independently selected from the group consisting of hydrogen; hydroxy; SO$_2$R$^d$; C$_{1-6}$ alkyl optionally substituted with one or more substituents independently selected from halogen, hydroxy, C$_{1-5}$ alkoxy, nitro, and N(R$^e$)$_2$; C$_{1-6}$ alkoxy optionally substituted with one or more substituents independently selected from halogen, hydroxy, C$_{1-5}$ alkoxy, nitro and N(R$^e$)$_2$; aryl optionally substituted with one or more substituents independently selected from halogen, hydroxy, C$_{1-4}$ alkyl, C$_{1-5}$ alkoxy, nitro, and N(R$^e$)$_2$; and heteroaryl optionally substituted with one or more substituents independently selected from halogen, hydroxy, C$_{1-4}$ alkyl, C$_{1-5}$ alkoxy, nitro, and N(R$^e$)$_2$;

R$^d$, for each occurrence, is independently selected from the group consisting of hydrogen; N(R$^e$)$_2$; C$_{1-6}$ alkyl optionally substituted with one or more substituents independently selected from halogen, hydroxy, C$_{1-5}$ alkoxy, nitro, and N(R$^e$)$_2$; aryl and heteroaryl; and R$^e$, for each occurrence, is independently hydrogen or C$_{1-6}$ alkyl.

Other exemplary combinations are illustrated by compounds of the following subgroups I-XII:

I. Compounds Having the Structure:

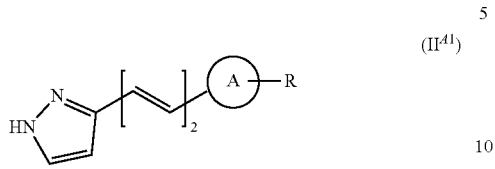

(II$^{A1}$)

tautomers thereof; and pharmaceutically acceptable derivatives thereof;

wherein A and R are as defined generally and in classes and subclasses herein. In certain embodiments, A represents an optionally substituted aromatic or non-aromatic 5-6 membered monocyclic ring, optionally containing 1-4 heteroatoms selected from N, O or S; or an optionally substituted aromatic or non-aromatic 8-12 membered bicyclic ring, optionally containing 1-6 heteroatoms selected from N, O or S. In the foregoing formula, the [C=C]$_2$ bond(s) can be the cis or the trans isomer. In certain other embodiments, R is selected from the group consisting of hydrogen; halogen; hydroxy; nitro; CN; aryl; heteroaryl; —C(=O)R$^a$; —NR$^b$R$^c$; —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring optionally containing 1-3 heteroatoms selected from the group consisting of N, O, and S; and C$_{1-6}$ alkyl, C$_{2-6}$ alkenyl, C$_{2-6}$ alkynyl, or C$_{3-6}$ cycloalkyl, each independently optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl;

wherein each occurrence of R$^a$ is independently selected from the group consisting of hydrogen, hydroxy, C$_{1-6}$ alkyl, C$_{1-6}$ alkoxy, aryl, heteroaryl, and NR$^b$R$^c$, wherein C$_{1-6}$ alkyl and C$_{1-6}$ alkoxy are optionally substituted with one or more substituents independently selected from halogen, hydroxy, C$_{1-5}$ alkoxy, nitro, and N(R$^e$)$_2$;

each occurrence of R$^b$ and R$^c$ is independently selected from the group consisting of hydrogen; hydroxy; SO$_2$R$^d$; C$_{1-6}$ alkyl optionally substituted with one or more substituents independently selected from halogen, hydroxy, C$_{1-5}$ alkoxy, nitro, and N(R$^e$)$_2$; C$_{1-6}$ alkoxy optionally substituted with one or more substituents independently selected from halogen, hydroxy, C$_{1-5}$ alkoxy, nitro and N(R$^e$)$_2$; aryl optionally substituted with one or more substituents independently selected from halogen, hydroxy, C$_{1-4}$ alkyl, C$_{1-5}$ alkoxy, nitro, and N(R$^e$)$_2$; and heteroaryl optionally substituted with one or more substituents independently selected from halogen, hydroxy, C$_{1-4}$ alkyl, C$_{1-5}$ alkoxy, nitro, and N(R$^e$)$_2$;

each occurrence of R$^d$ is independently selected from the group consisting of hydrogen; N(R$^e$)$_2$; C$_{1-6}$ alkyl optionally substituted with one or more substituents independently selected from halogen, hydroxy, C$_{1-5}$ alkoxy, nitro, and N(R$^e$)$_2$; aryl and heteroaryl; and each occurrence of R$^e$ is independently hydrogen or C$_{1-6}$ alkyl.

A non-limiting example of compounds of this subgroup includes:

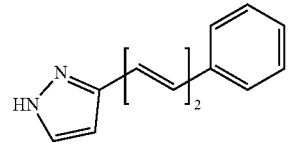

II. Compounds Having the Structure:

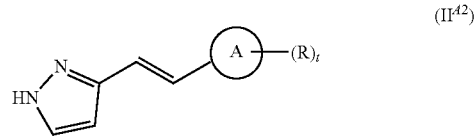

(II$^{A2}$)

tautomers thereof, and pharmaceutically acceptable derivatives thereof;

wherein A and R are as defined generally and in classes and subclasses herein and t is 1-5. The C=C bond can be the cis or the trans isomer.

In certain exemplary embodiments, A is an aromatic or non-aromatic 5-6 membered monocyclic ring, optionally containing 1-4 heteroatoms selected from N, O or S; or an aromatic or non-aromatic 8-12 membered bicyclic ring, optionally containing 1-6 heteroatoms selected from N, O or S;

and each R is independently selected from the group consisting of hydrogen; halogen; hydroxy; nitro; CN; aryl; heteroaryl; —C(=O)R$^a$; —NR$^b$R$^c$; —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring optionally containing 1-3 heteroatoms selected from the group consisting of N, O, and S; and C$_{1-6}$ alkyl, C$_{2-6}$ alkenyl, C$_{2-6}$ alkynyl, or C$_{3-6}$ cycloalkyl, each independently optionally substituted with one or more substituents independently selected from halogen, hydroxy, C$_{1-5}$ alkoxy, nitro, and N(R$^e$)$_2$;

wherein each occurrence of R$^a$ is independently selected from the group consisting of hydrogen, hydroxy, C$_{1-6}$ alkyl, C$_{1-6}$ alkoxy, aryl, heteroaryl, and NR$^b$R$^c$, wherein C$_{1-6}$ alkyl and C$_{1-6}$ alkoxy are optionally substituted with one or more substituents independently selected from halogen, hydroxy, C$_{1-5}$ alkoxy, nitro, and N(R$^e$)$_2$;

each occurrence of R$^b$ and R$^c$ is independently selected from the group consisting of hydrogen; hydroxy; SO$_2$R$^d$; C$_{1-6}$ alkyl optionally substituted with one or more substituents independently selected from halogen, hydroxy, C$_{1-5}$ alkoxy, nitro, and N(R$^e$)$_2$; C$_{1-6}$ alkoxy optionally substituted with one or more substituents independently selected from halogen, hydroxy, C$_{1-5}$ alkoxy, nitro and N(R$^e$)$_2$; aryl optionally substituted with one or more substituents independently selected from halogen, hydroxy, C$_{1-4}$ alkyl, C$_{1-5}$ alkoxy, nitro, and N(R$^e$)$_2$; and heteroaryl optionally substituted with one or more substituents independently selected from halogen, hydroxy, C$_{1-4}$ alkyl, C$_{1-5}$ alkoxy, nitro, and N(R$^e$)$_2$;

each occurrence of R$^d$ is independently selected from the group consisting of hydrogen; N(R$^e$)$_2$; C$_{1-6}$ alkyl optionally substituted with one or more substituents independently selected from halogen, hydroxy, C$_{1-5}$ alkoxy, nitro, and N(R$^e$)$_2$; aryl and heteroaryl; and each occurrence of $R^e$ is independently hydrogen or $C_{1-6}$ alkyl;

or a prodrug, salt, hydrate, or ester thereof.

III. Compounds Having the Structure:

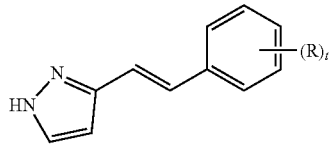
(II$^{B1}$)

tautomers thereof, and pharmaceutically acceptable derivatives thereof;

wherein t and R are as defined generally and in classes and subclasses herein. In certain embodiments, R is as defined for subgroup II above. In the foregoing formula, the C=C bond can be the cis or the trans isomer. Non-limiting examples of compounds this subgroup include:

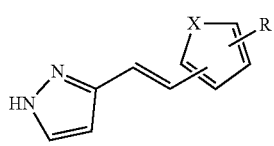
(II$^{C1}$)

IV. Compounds Having the Structure:

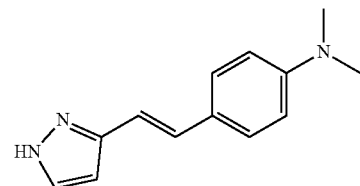

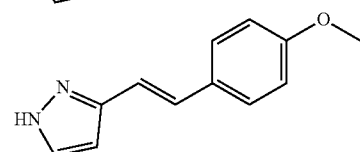

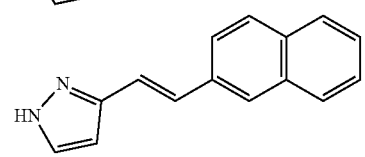

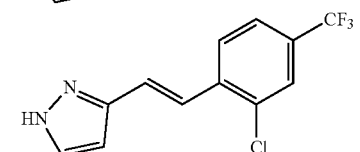

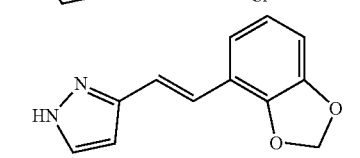

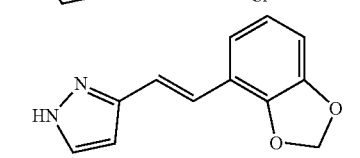

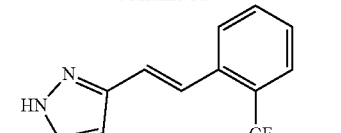

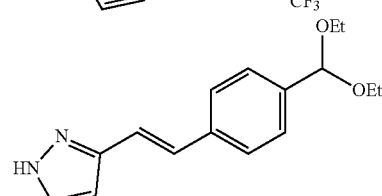

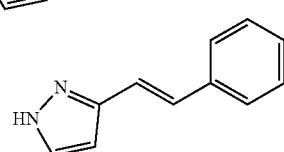

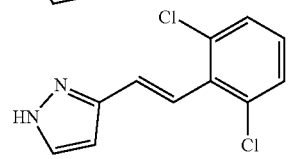

tautomers thereof, and pharmaceutically acceptable derivatives thereof;

wherein R is as defined generally and in classes and subclasses herein; and X is O, S or $NR^N$ wherein $R^N$ is hydrogen, alkyl, heteroalkyl, aryl, heteroaryl, -(alkyl)aryl, -(alkyl)heteroaryl, acyl or a nitrogen protecting group. In the foregoing formula, the C=C bond can be the cis or the trans isomer. In certain embodiments, R is as defined for subgroup II above.

Non-limiting examples of compounds of this subgroup include:

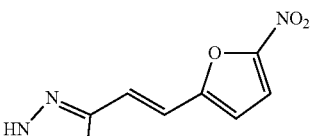

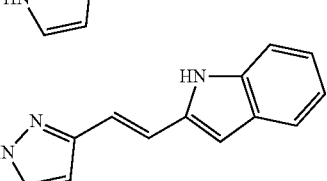

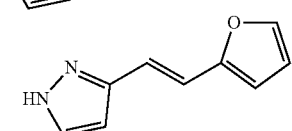

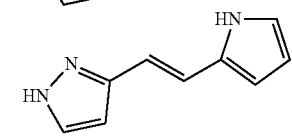

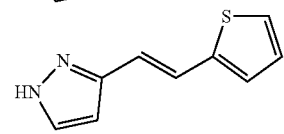

-continued

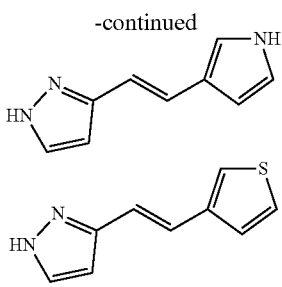

V. Compounds Having the Structure:

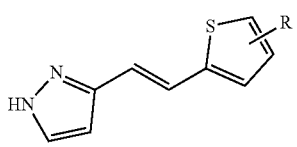
(II$^{C2}$)

tautomers thereof, and pharmaceutically acceptable derivatives thereof;

wherein R is as defined generally and in classes and subclasses herein. In certain embodiments, R is as defined in subgroup II above. In the foregoing formula, the —C═C— bond can be the cis or the trans isomer.

VI. Compounds Having the Structure:

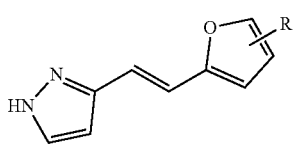
(II$^{C3}$)

tautomers thereof, and pharmaceutically acceptable derivatives thereof;

wherein R is as defined generally and in classes and subclasses herein. In certain embodiments, R is as defined in subgroup II above. In the foregoing formula, the —C═C— bond can be the cis or the trans isomer.

VII. Compounds Having the Structure:

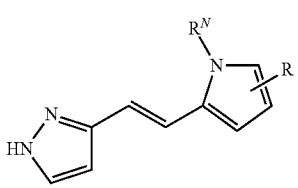
(II$^{C4}$)

tautomers thereof, and pharmaceutically acceptable derivatives thereof;

wherein R is as defined generally and in classes and subclasses herein; and R$^N$ is hydrogen, alkyl, heteroalkyl, aryl, heteroaryl, -(alkyl)aryl, -(alkyl)heteroaryl, acyl or a nitrogen protecting group. In certain embodiments, R is as defined in subgroup II above. In certain other embodiments, R$^N$ is hydrogen. In the foregoing formula, the —C═C— bond can be the cis or the trans isomer.

In another broad aspect of the present invention, the following disubstituted compounds and their C(5)-positional isomers are embraced herein, such compounds exhibiting HGF/SF mimicking/modulating activity, and in particularly activity similar to that of HGF/SF.

VIII. Compounds Having the Structure:

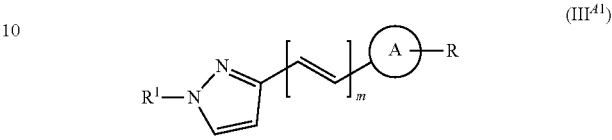
(III$^{41}$)

C(5)-positional isomers thereof; and pharmaceutically acceptable derivatives thereof;

wherein R$^1$ and R are as defined generally and in classes and subclasses herein; m is an integer from 0-3; and A represents an optionally substituted aromatic or non-aromatic 5-6 membered monocyclic ring, optionally containing 1-4 heteroatoms selected from N, O or S; or an optionally substituted aromatic or non-aromatic 8-12 membered bicyclic ring, optionally containing 1-6 heteroatoms selected from N, O or S. In the foregoing formula, the [C═C]$_m$ bond(s) can be the cis or the trans isomer. In certain other embodiments, R$^1$ is SO$_2$AL$^2$, C(═O)(CH$_2$)$_m$AL$^2$, C(═O)OAL$^2$, C(═O)NHAL$^2$, SO$_2$Aryl, C(═O)(CH$_2$)$_m$Aryl, C(═O)OAryl, C(═O)Oheterocyclic, C(═O)(CH$_2$)$_m$Heterocyclic, or C(═O)NHAryl; wherein AL$^2$ is an alkyl or cycloalkyl moiety; and AL$^2$, the aryl and heterocyclic moiety are independently optionally substituted with one or more substituents independently selected from the group consisting of hydrogen; halogen; hydroxy; nitro; CN; aryl; heteroaryl; —C(═O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(═O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; or COCH$_2$OC$_2$H$_5$OCH$_3$. In certain embodiments, R is as defined in subgroup II above.

IX. Compounds Having the Structure:

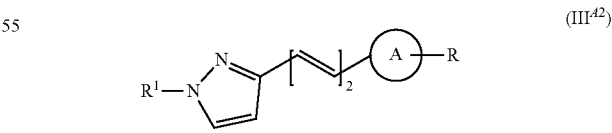
(III$^{42}$)

C(5)-positional isomers thereof; and pharmaceutically acceptable derivatives thereof;

wherein A, R$^1$ and R are as defined generally and in classes and subclasses herein. In the foregoing formula, the [C═C]$_2$ bonds can be the cis or the trans isomer. In certain embodiments, A represents an optionally substituted aromatic or non-aromatic 5-6 membered monocyclic ring, optionally containing 1-4 heteroatoms selected from N, O or S; or an optionally substituted aromatic or non-aromatic 8-12 membered bicyclic ring, optionally containing 1-6 heteroatoms selected from N, O or S. In certain other embodiments, $R^1$ is $SO_2AL^2$, $C(=O)(CH_2)_mAL^2$, $C(=O)OAL^2$, $C(=O)NHAL^2$, $SO_2Aryl$, $C(=O)(CH_2)_mAryl$, $C(=O)OAryl$, $C(=O)Oheterocyclic$, $C(=O)(CH_2)_mHeterocyclic$, or $C(=O)NHAryl$; wherein m is an integer from 0-3; $AL^2$ is an alkyl or cycloalkyl moiety; and $AL^2$, the aryl and heterocyclic moiety are independently optionally substituted with one or more substituents independently selected from the group consisting of hydrogen; halogen; hydroxy; nitro; CN; aryl; heteroaryl; —C(=O)$R^a$, —$NR^bR^c$, or —S(O)$_nR^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and $N(R^e)_2$; and further optionally substituted with 1-3 substituents independently selected from the group consisting of —C(=O)$R^a$, —$NR^bR^c$, —S(O)$_nR^d$ where n=0-2, hydroxy, $C_{1-6}$ alkoxy, halo$C_{1-6}$ alkoxy, aryl, heteroaryl and heterocyclyl; or $COCH_2OC_2H_5OCH_3$. In certain embodiments, R is as defined in subgroup II above.

X. Compounds Having the Structure:

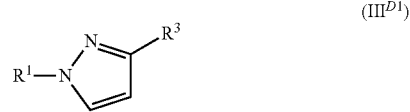

(III$^{D1}$)

C(5)-positional isomers thereof; and pharmaceutically acceptable derivatives thereof;

wherein $R^1$ is $C(=O)(CH_2)_mAL^2$, $C(=O)OAL^2$, $C(=O)(CH_2)_mAryl$, $C(=O)OAryl$, $C(=O)Heteroaryl$ or $C(=O)Heterocyclic$; where m is an integer from 1-3; $AL^2$ is an aliphatic or alicyclic moiety; and $AL^2$, the aryl, heteroaryl and heterocyclic moiety are independently optionally substituted with one or more substituents independently selected from hydrogen; halogen; hydroxy; nitro; CN; aryl; heteroaryl; —C(=O)$R^a$, —$NR^bR^c$, or —S(O)$_nR^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and $N(R^e)_2$; and further optionally substituted with 1-3 substituents independently selected from the group consisting of —C(=O)$R^a$, —$NR^bR^c$, —S(O)$_nR^d$ where n=0-2, hydroxy, $C_{1-6}$ alkoxy, halo$C_{1-6}$ alkoxy, aryl, heteroaryl and heterocyclyl; or $COCH_2OC_2H_5OCH_3$; and $R^3$ is a cis or trans CHCHAryl, CHCHHeterocyclic, phenoxyphenyl, or a heterocyclic group, wherein the aryl, heterocyclic or phenoxyphenyl moiety may be optionally substituted with one or more substituents independently selected from the group consisting of hydrogen; halogen; hydroxy; nitro; CN; aryl; heteroaryl; —C(=O)$R^a$, —$NR^bR^c$, or —S(O)$_nR^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and $N(R^e)_2$; and further optionally substituted with 1-3 substituents independently selected from the group consisting of —C(=O)$R^a$, —$NR^bR^c$, —S(O)$_nR^d$ where n=0-2, hydroxy, $C_{1-6}$ alkoxy, halo$C_{1-6}$ alkoxy, aryl, heteroaryl and heterocyclyl;

wherein $R^a$ is selected from the group consisting of hydrogen, hydroxy, $C_{1-6}$ alkyl, $C_{1-6}$ alkoxy, aryl, heteroaryl, and $NR^bR^c$, wherein $C_{1-6}$ alkyl and $C_{1-6}$ alkoxy are optionally substituted with one or more substituents independently selected from halogen, hydroxy, $C_{1-5}$ alkoxy, nitro, and $N(R^e)_2$;

$R^b$ and $R^c$ are independently selected from the group consisting of hydrogen; hydroxy; $SO_2R^d$; $C_{1-6}$ alkyl optionally substituted with one or more substituents independently selected from halogen, hydroxy, $C_{1-5}$ alkoxy, nitro, and $N(R^e)_2$; $C_{1-6}$ alkoxy optionally substituted with one or more substituents independently selected from halogen, hydroxy, $C_{1-5}$ alkoxy, nitro and $N(R^e)_2$; aryl optionally substituted with one or more substituents independently selected from halogen, hydroxy, $C_{1-4}$ alkyl, $C_{1-5}$ alkoxy, nitro, and $N(R^e)_2$; and heteroaryl optionally substituted with one or more substituents independently selected from halogen, hydroxy, $C_{1-4}$ alkyl, $C_{1-5}$ alkoxy, nitro, and $N(R^e)_2$;

$R^d$ is selected from the group consisting of hydrogen; $N(R^e)_2$; $C_{1-6}$ alkyl optionally substituted with one or more substituents independently selected from halogen, hydroxy, $C_{1-5}$ alkoxy, nitro, and $N(R^e)_2$; aryl and heteroaryl; and $R^e$ is hydrogen or $C_{1-6}$ alkyl.

In certain embodiments, for the compounds of formula (III$^{D1}$) above, $AL^2$ is an alkyl or cycloalkyl moiety.

In certain embodiments, for the compounds of formula (III$^{D1}$) above, $R^3$ is a cis or trans CHCHHeterocyclic, phenoxyphenyl, or a heterocyclic group, optionally substituted with one or more substituents independently selected from the group consisting of hydrogen; halogen; hydroxy; nitro; CN; aryl; heteroaryl; —C(=O)$R^a$, —$NR^bR^c$, or —S(O)$_nR^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and $N(R^e)_2$; and further optionally substituted with 1-3 substituents independently selected from the group consisting of —C(=O)$R^a$, —$NR^bR^c$, —S(O)$_nR^d$ where n=0-2, hydroxy, $C_{1-6}$ alkoxy, halo$C_{1-6}$ alkoxy, aryl, heteroaryl and heterocyclyl;

wherein $R^a$ is selected from the group consisting of hydrogen, hydroxy, $C_{1-6}$ alkyl, $C_{1-6}$ alkoxy, aryl, heteroaryl, and $NR^bR^c$, wherein $C_{1-6}$ alkyl and $C_{1-6}$ alkoxy are optionally substituted with one or more substituents independently selected from halogen, hydroxy, $C_{1-5}$ alkoxy, nitro, and $N(R^e)_2$;

$R^b$ and $R^c$ are independently selected from the group consisting of hydrogen; hydroxy; $SO_2R^d$; $C_{1-6}$ alkyl optionally substituted with one or more substituents independently selected from halogen, hydroxy, $C_{1-5}$ alkoxy, nitro, and $N(R^e)_2$; $C_{1-6}$ alkoxy optionally substituted with one or more substituents independently selected from halogen, hydroxy, $C_{1-5}$ alkoxy, nitro and $N(R^e)_2$; aryl optionally substituted with one or more substituents independently selected from halogen, hydroxy, $C_{1-4}$ alkyl, $C_{1-5}$ alkoxy, nitro, and $N(R^e)_2$; and heteroaryl optionally substituted with one or more substituents independently selected from halogen, hydroxy, $C_{1-4}$ alkyl, $C_{1-5}$ alkoxy, nitro, and $N(R^e)_2$;

$R^d$ is selected from the group consisting of hydrogen; $N(R^e)_2$; $C_{1-6}$ alkyl optionally substituted with one or more substituents independently selected from halogen, hydroxy, $C_{1-5}$ alkoxy, nitro, and $N(R^e)_2$; aryl and heteroaryl; and $R^e$ is hydrogen or $C_{1-6}$ alkyl.

Non-limiting examples of compounds of this subgroup include:

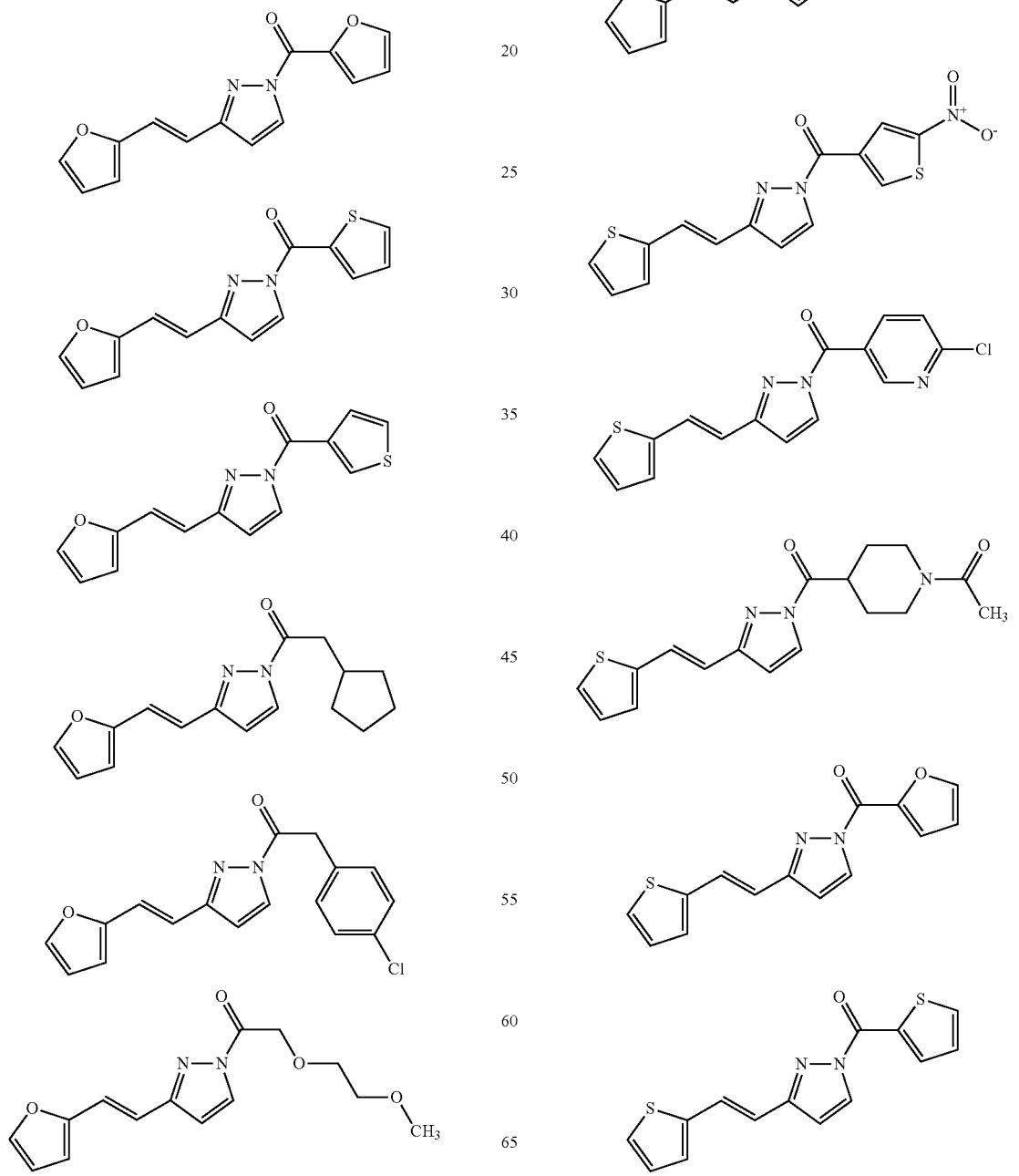

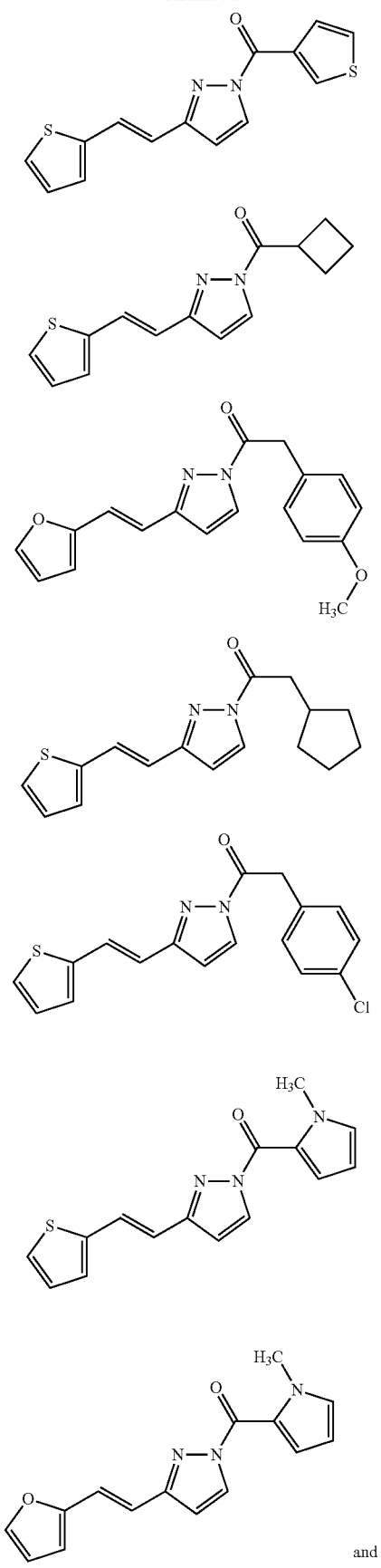

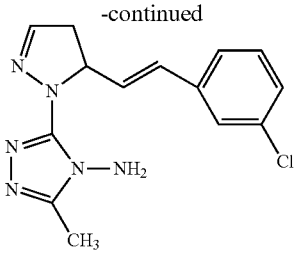

and

As mentioned above and herein throughout, although the compound structures depicted herein are substituted at the 1 and 3 positions, the invention embraces such positional isomers where the 3-substituent is at the 5 position, and any combination thereof.

In another aspect of compounds of Formula (III$^{D1}$), R$^3$ is a cis or trans CHCHAryl, optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl;

wherein R$^a$ is selected from the group consisting of hydrogen, hydroxy, C$_{1-6}$ alkyl, C$_{1-6}$ alkoxy, aryl, heteroaryl, and NR$^b$R$^c$, wherein C$_{1-6}$ alkyl and C$_{1-6}$ alkoxy are optionally substituted with one or more substituents independently selected from halogen, hydroxy, C$_{1-5}$ alkoxy, nitro, and N(R$^e$)$_2$;

R$^b$ and R$^c$ are independently selected from the group consisting of hydrogen; hydroxy; SO$_2$R$^d$; C$_{1-6}$ alkyl optionally substituted with one or more substituents independently selected from halogen, hydroxy, C$_{1-5}$ alkoxy, nitro, and N(R$^e$)$_2$; C$_{1-6}$ alkoxy optionally substituted with one or more substituents independently selected from halogen, hydroxy, C$_{1-5}$ alkoxy, nitro and N(R$^e$)$_2$; aryl optionally substituted with one or more substituents independently selected from halogen, hydroxy, C$_{1-4}$ alkyl, C$_{1-5}$ alkoxy, nitro, and N(R$^e$)$_2$; and heteroaryl optionally substituted with one or more substituents independently selected from halogen, hydroxy, C$_{1-4}$ alkyl, C$_{1-5}$ alkoxy, nitro, and N(R$^e$)$_2$;

R$^d$ is selected from the group consisting of hydrogen; N(R$^e$)$_2$; C$_{1-6}$ alkyl optionally substituted with one or more substituents independently selected from halogen, hydroxy, C$_{1-5}$ alkoxy, nitro, and N(R$^e$)$_2$; aryl and heteroaryl; and R$^e$ is hydrogen or C$_{1-6}$ alkyl.

Non-limiting examples of compounds of this subgroup include:

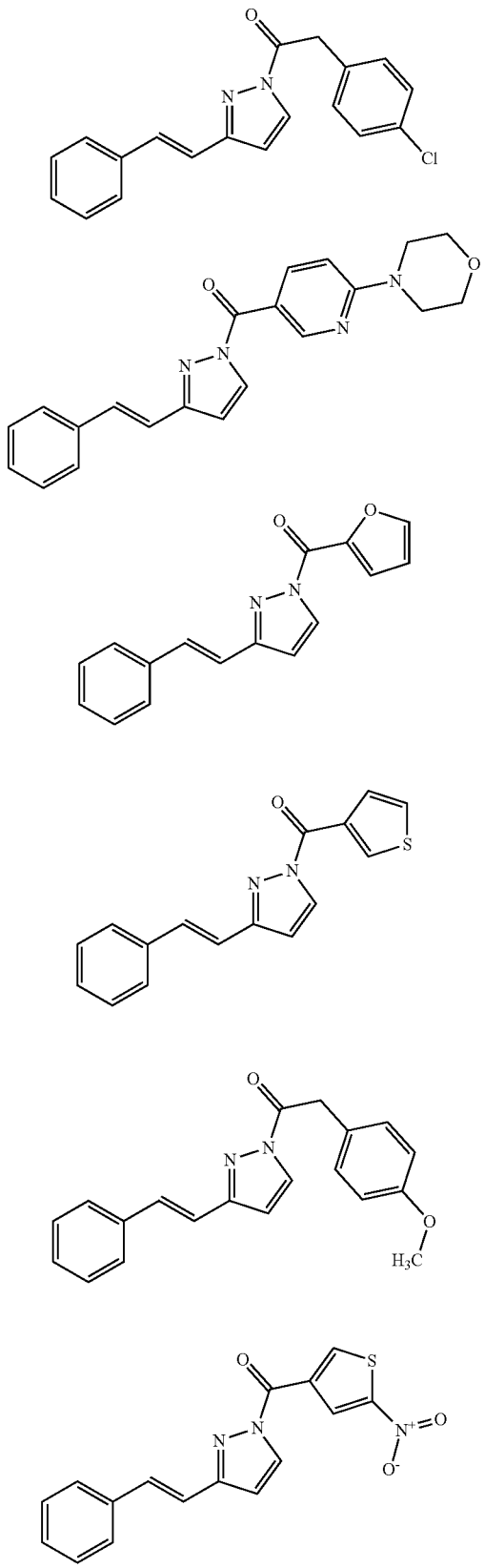

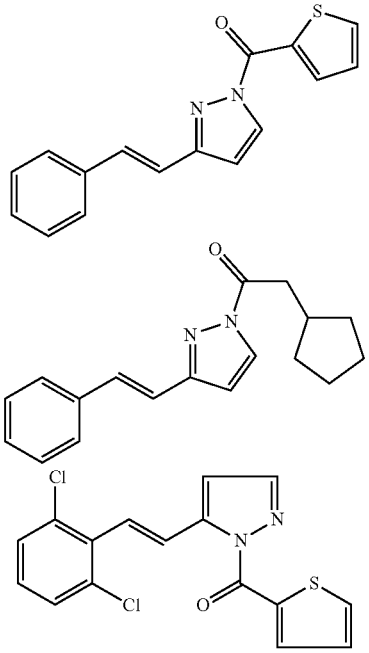

XI. Compounds Having the Structure:

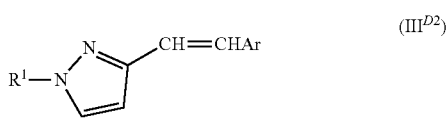

(III$^{D2}$)

C(5)-positional isomers thereof; and pharmaceutically acceptable derivatives thereof;

wherein R$^1$ is SO$_2$AL$^2$, C(=O)(CH$_2$)$_m$AL$^2$, C(=O)OAL$^2$, C(=O)NHAL$^2$, SO$_2$Aryl, C(=O)(CH$_2$)$_m$Aryl, C(=O)OAryl, C(=O)Oheterocyclic, C(=O)(CH$_2$)$_m$Heterocyclic, or C(=O)NHAryl; wherein m is an integer from 1-3; AL$^2$ is an aliphatic or alicyclic moiety; and AL$^2$, the aryl and heterocyclic moiety are independently optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-s}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; or COCH$_2$OC$_2$H$_5$OCH$_3$; and CHCHAr is a cis or trans CH=CHAryl optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$;

wherein R$^a$ is selected from the group consisting of hydrogen, hydroxy, C$_{1-6}$ alkyl, C$_{1-6}$ alkoxy, aryl, heteroaryl, and NR$^b$R$^c$, wherein C$_{1-6}$ alkyl and C$_{1-6}$ alkoxy are optionally substituted with one or more substituents independently selected from halogen, hydroxy, C$_{1-5}$ alkoxy, nitro, and N(R$^e$)$_2$;

R$^b$ and R$^c$ are independently selected from the group consisting of hydrogen; hydroxy; SO$_2$R$^d$; C$_{1-6}$ alkyl optionally substituted with one or more substituents independently selected from halogen, hydroxy, C$_{1-5}$ alkoxy, nitro, and N(R$^e$)$_2$; C$_{1-6}$ alkoxy optionally substituted with one or more substituents independently selected from halogen, hydroxy, C$_{1-5}$ alkoxy, nitro and N(R$^e$)$_2$; aryl optionally substituted with one or more substituents independently selected from halogen, hydroxy, C$_{1-4}$ alkyl, C$_{1-5}$ alkoxy, nitro, and N(R$^e$)$_2$; and heteroaryl optionally substituted with one or more substituents independently selected from halogen, hydroxy, C$_{1-4}$ alkyl, C$_{1-5}$ alkoxy, nitro, and N(R$^e$)$_2$;

R$^d$ is selected from the group consisting of hydrogen; N(R$^e$)$_2$; C$_{1-6}$ alkyl optionally substituted with one or more substituents independently selected from halogen, hydroxy, C$_{1-5}$ alkoxy, nitro, and N(R$^e$)$_2$; aryl and heteroaryl; and R$^e$ is hydrogen or C$_{1-6}$ alkyl.

In certain embodiments, for compounds of Formula (III$^{D2}$), R$^1$ is C(=O)(CH$_2$)$_m$AL$^2$, C(=O)OAL$^2$, C(=O)(CH$_2$)$_m$Aryl, C(=O)OAryl, C(=O)OHeterocyclic or C(=O)(CH$_2$)$_m$Heterocyclic; wherein m is an integer from 1-3; AL$^2$ is an aliphatic or alicyclic moiety; and AL$^2$, the aryl and heterocyclic moiety are independently optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl;

or COCH$_2$OC$_2$H$_5$OCH$_3$.

Non-limiting examples of compound of this subgroup include:

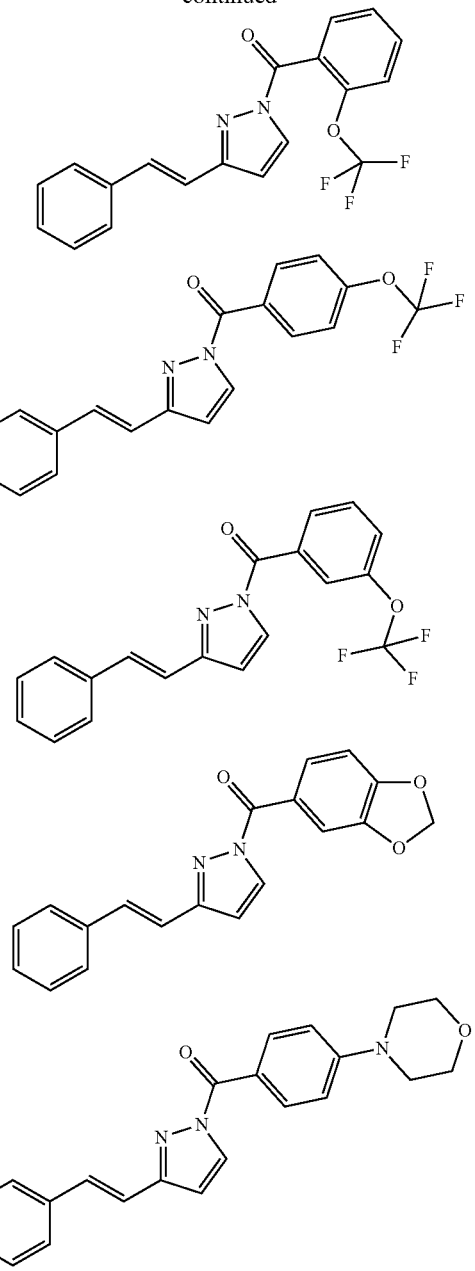

In certain other embodiments, for compounds of Formula (III$^{D2}$), R$^1$ is SO$_2$AL$^2$, C(=O)AL$^2$, C(=O)NHAL$^2$, SO$_2$Aryl, C(=O)Aryl, or C(=O)NHAryl; wherein AL$^2$ is an aliphatic or alicyclic moiety; and AL$^2$ and the aryl moiety are independently optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; or COCH$_2$OC$_2$H$_5$OCH$_3$.

Non-limiting examples of this subgroup include:

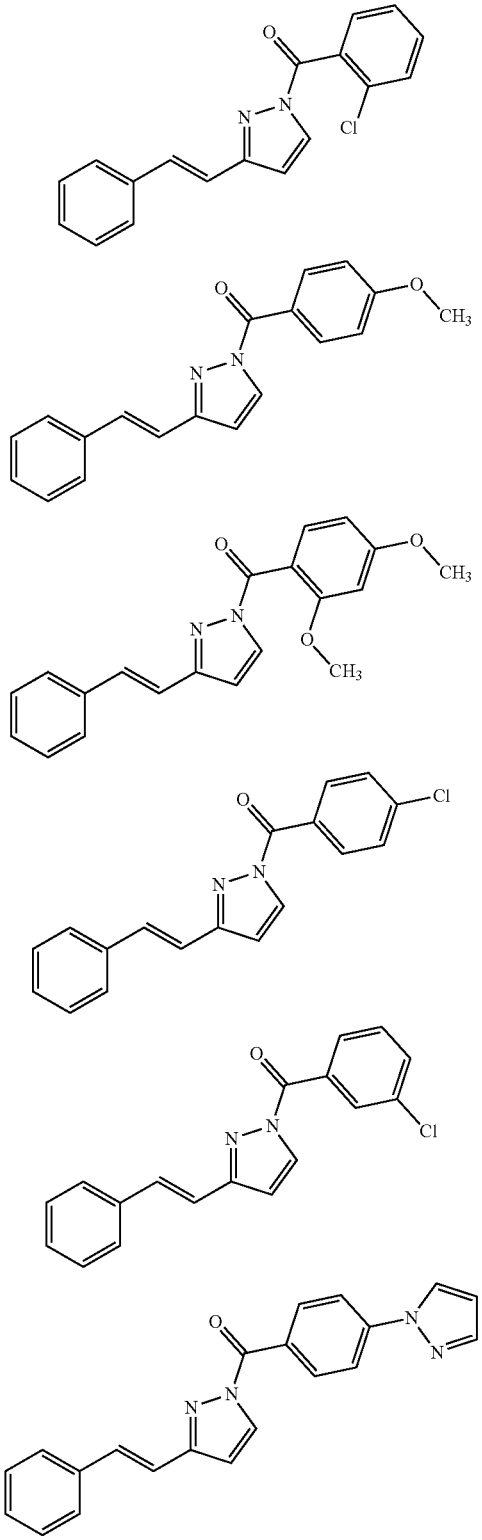

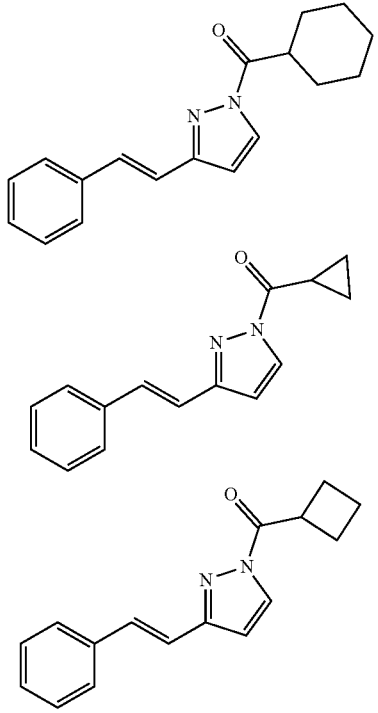

In certain embodiments, for the compounds of subgroup XI above, AL$^2$ is an alkyl or cycloalkyl moiety.

XII. Compounds Having the Structure:

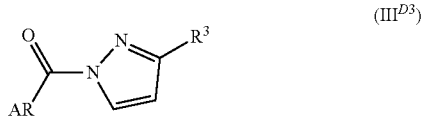

(III$^{D3}$)

C(5)-positional isomer thereof; and pharmaceutically acceptable derivatives thereof;

wherein AR is an optionally fused 3-12 membered aromatic or alicyclic mono- or bicyclic-ring containing 0-3 heteroatoms selected from the group consisting of N, O, and S optionally substituted with one or more substituents independently selected from the group consisting of hydrogen; halogen; hydroxy; nitro; CN; aryl; heteroaryl; heterocycle; carboxy ester; C(=O)R$^a$, NR$^b$R$^c$, or S(O)$_n$R$^d$ where n=0-2; C$_{1-6}$alkoxy substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; —NR$^f$R$^g$; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; and R$^3$ is a cis or trans CHCHheterocyclic, phenoxyphenyl, or a heterocyclic group, optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; $C_{1-6}$ alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and $N(R^e)_2$; and further optionally substituted with 1-3 substituents independently selected from the group consisting of —C(=O)$R^a$, —$NR^bR^c$, —S(O)$R^d$ where n=0-2, hydroxy, $C_{1-6}$ alkoxy, halo$C_{1-6}$ alkoxy, aryl, heteroaryl and heterocyclyl;

wherein $R^a$ is selected from the group consisting of hydrogen, hydroxy, $C_{1-6}$ alkyl, $C_{1-6}$ alkoxy, aryl, heteroaryl, and $NR^bR^c$, wherein $C_{1-6}$ alkyl and $C_{1-6}$ alkoxy are optionally substituted with one or more substituents independently selected from halogen, hydroxy, $C_{1-5}$ alkoxy, nitro, and $N(R^e)_2$;

$R^b$ and $R^c$ are independently selected from the group consisting of hydrogen; hydroxy; $SO_2R^d$; $C_{1-6}$ alkyl optionally substituted with one or more substituents independently selected from halogen, hydroxy, $C_{1-5}$ alkoxy, nitro, and $N(R^e)_2$; $C_{1-6}$ alkoxy optionally substituted with one or more substituents independently selected from halogen, hydroxy, $C_{1-5}$ alkoxy, nitro and $N(R^e)_2$; aryl optionally substituted with one or more substituents independently selected from halogen, hydroxy, $C_{1-4}$ alkyl, $C_{1-5}$ alkoxy, nitro, and $N(R^e)_2$; and heteroaryl optionally substituted with one or more substituents independently selected from halogen, hydroxy, $C_{1-4}$ alkyl, $C_{1-5}$ alkoxy, nitro, and $N(R^e)_2$;

$R^d$ is selected from the group consisting of hydrogen; $N(R^e)_2$; $C_{1-6}$ alkyl optionally substituted with one or more substituents independently selected from halogen, hydroxy, $C_{1-5}$ alkoxy, nitro, and $N(R^e)_2$; aryl and heteroaryl;

$R^e$ is hydrogen or $C_{1-6}$ alkyl; and $R^f$ and $R^g$ are independently selected from the group consisting of hydrogen; hydroxy; $SO_2R^d$; $C_{1-6}$ alkyl substituted with one or more substituents independently selected from halogen, hydroxy, $C_{1-5}$ alkoxy, nitro, and $N(R^e)_2$; $C_{1-6}$ alkoxy optionally substituted with one or more substituents independently selected from halogen, hydroxy, $C_{1-5}$ alkoxy, nitro and $N(R^e)_2$; aryl optionally substituted with one or more substituents independently selected from halogen, hydroxy, $C_{1-4}$ alkyl, $C_{1-5}$ alkoxy, nitro, and $N(R^e)_2$; and heteroaryl optionally substituted with one or more substituents independently selected from halogen, hydroxy, $C_1$ alkyl, $C_{1-5}$ alkoxy, nitro, and $N(R^e)_2$.

In certain embodiments, when AR is aryl substituted with $C_{1-6}$ alkyl, the $C_{1-6}$ alkyl moiety is substituted. In certain exemplary embodiments, the substituents are independently selected from halogen, hydroxy, $C_{1-5}$ alkoxy, nitro and $N(R^e)_2$.

Non-limiting examples of compounds of this subgroup include:

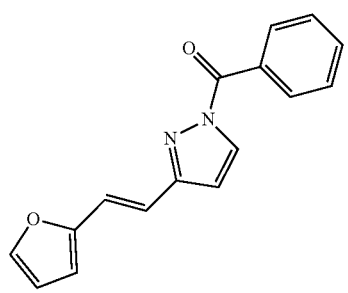

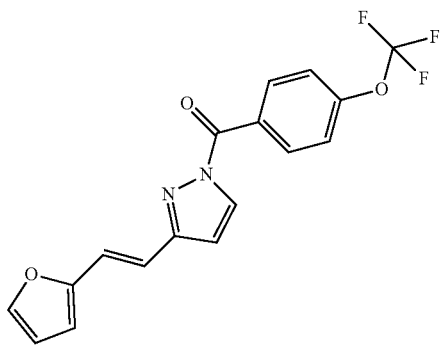

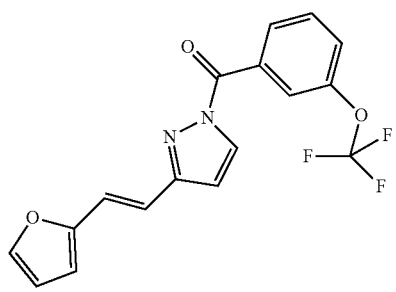

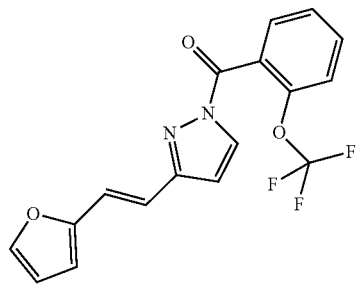

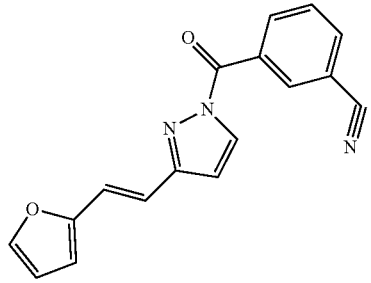

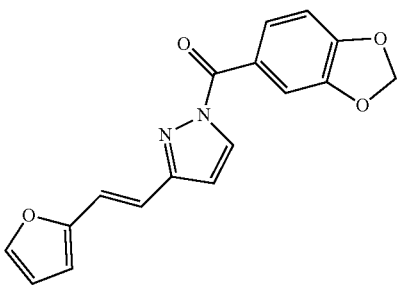

-continued
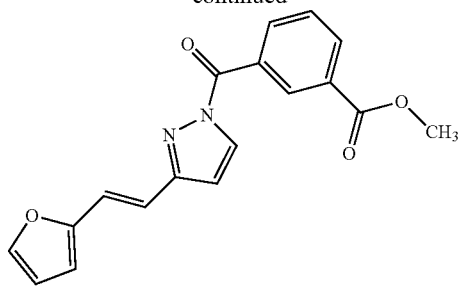
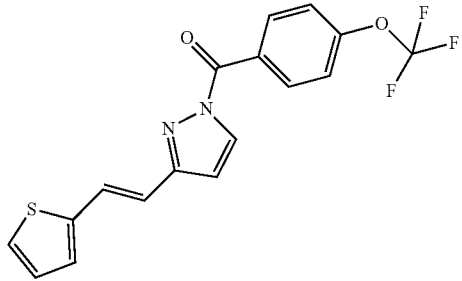
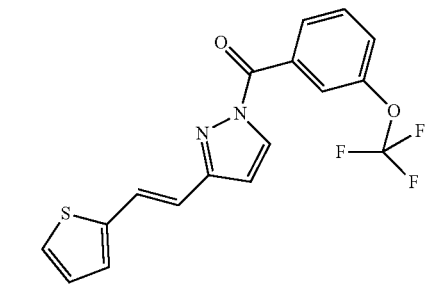
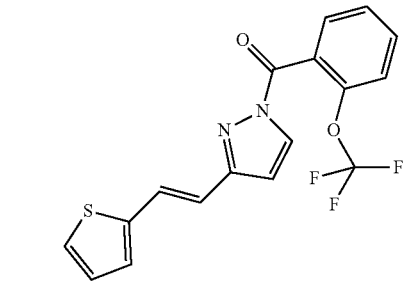
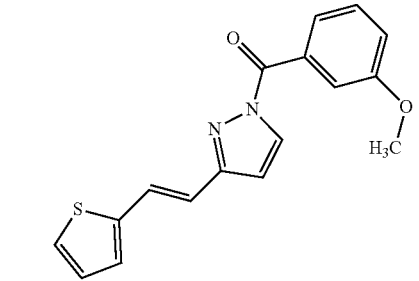
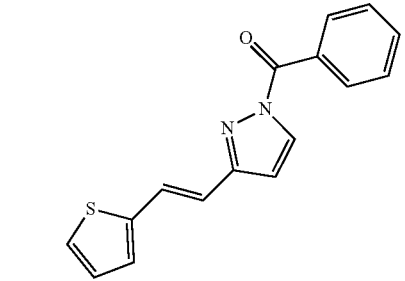
-continued
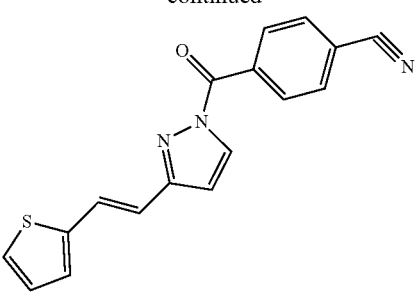
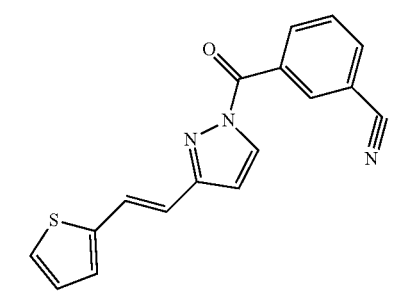
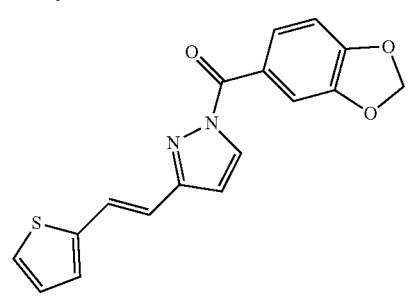
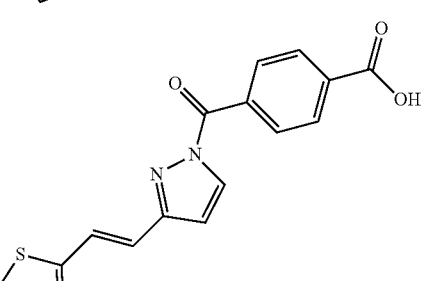
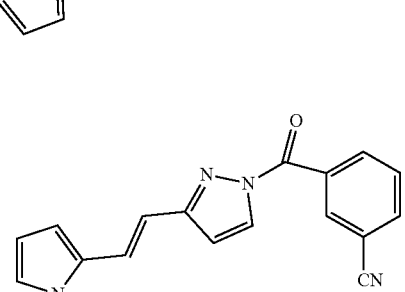
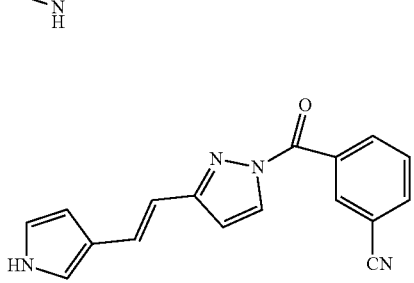

-continued

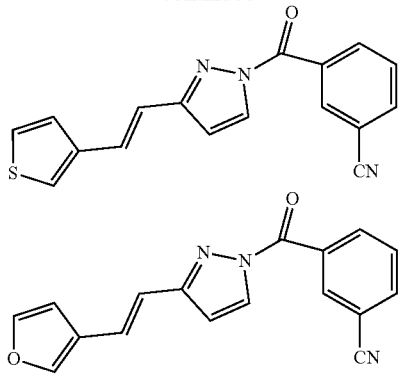

It will be appreciated that each of the compounds described herein and each of the subclasses of compounds described above (I-XII) may be substituted as described generally herein, or may be substituted according to any one or more of the subclasses described above and herein [e.g., i)-liv)].

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I), (II) and (III) under different conditions and may exist as one or a combination of polymorphs of compound of general formula (I), (II) and (III) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. In some embodiments, the present invention provides an amorphous compound of formula (I), (II) and (III). Preparation of amorphous solid forms are known in the art and include lyophilization and spray drying. Thus, the present invention encompasses inventive compounds, their derivatives, their tautomeric forms, their stereoisomers, their C(5)-positional isomer their polymorphs, their pharmaceutically acceptable salts their pharmaceutically acceptable solvates and pharmaceutically acceptable compositions containing them. Tautomeric forms of compounds of the present invention include, for example the 3- and 5-substituted pyrazole tautomers of any of the aforementioned disubstituted compounds of general Formula II and related formulas. Likewise, C(5)-positional isomers of the 1,3-disubstituted pyrazoles of general Formula I and III and related formulas are encompassed within the scope of the present invention. Thus, the invention encompasses 1,5-disubstituted pyrazoles.

2) Pharmaceutical Compositions

As discussed above this invention provides new formulations and compositions of compounds that have biological properties useful for the treatment of any of a number of conditions or diseases in which HGF/SF or the activities thereof have a therapeutically useful role, or in some instances, where antagonism thereof is useful. Such compounds are described in U.S. Pat. Nos. 7,192,976; 7,250, 437; and 7,265,112, all of which are incorporated herein by reference in their entireties.

Accordingly, in another aspect of the present invention, pharmaceutical compositions and formulations are provided which comprise any one or more of the compounds described herein (or a prodrug, pharmaceutically acceptable salt or other pharmaceutically acceptable derivative thereof), and a pharmaceutically acceptable carrier. In certain embodiments, these compositions optionally further comprise one or more additional therapeutic agents. In certain embodiments such one or more agents are antiapoptotic, angiogenic or antifibrotic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder related to HGF/SF activity. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood, or N-demethylation of a compound of the invention where $R^1$ is methyl. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference. By way of example, N-methylated pro-drugs of the 3(5)-monosubstituted pyrazoles of the invention are embraced herein.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In one embodiment, liquid compositions or liquid formulations comprising compounds of the invention are provided that have increased solubility as compared to compounds of the invention dissolved in aqueous buffer such as phosphate-buffered saline. In one embodiment, such liquid compositions with increased solubility are provided by a composition comprising polyethylene glycol, polysorbate or a combination thereof. In one embodiment, the polyethylene glycol is polyethylene glycol 300. In another embodiment the polysorbate is polysorbate 80. In another embodiment the polyethylene glycol is present at about 40% to about 60% (v/v). In another embodiment the polysorbate is present at about 5% to about 15% (v/v). In another embodiment the polyethylene glycol is present at about 50% (v/v). In another embodiment the polysorbate is present at about 10% (v/v). In one formulation, the polyethylene glycol is present at 50% (v/v) together with polysorbate 80 at 10% (v/v). The balance of the solution can be a saline solution, a buffer or a buffered saline solution, such as phosphate-buffered saline. The pH of the solution can be from about pH 5 to about pH 9, and in other embodiments, about from pH 6 to about pH 8. In one embodiment the pH of the buffer is 7.4. In the foregoing embodiments, the compound of the invention is soluble at a concentration higher than in buffer alone, and can be present at about 0.8 to about 10 milligrams per milliliter of solution, or even higher. These formulations offer the preparation of convenient dosing solutions of practical volumes for single dose administration, by any route, in particular a parenteral route. In one embodiment, the route is intravenous, subcutaneous or intraperitoneal. Such compositions with a higher solubility permit achievement of more elevated blood concentrations that provide efficacy when the a threshold Cmax (maximal blood concentration after administration) should be achieved for optimal efficacy.

In certain embodiments, the compounds in the aforementioned compositions and formulations include (E)-3(5)-[2-(2,3-methylenedioxyphenyl)vinyl]-1H-pyrazole, (Z)-3(5)-[2-(2,3-methylenedioxyphenyl)vinyl]-1H-pyrazole, (E)-3(5)-[2-(2-chloro-5-trifluoromethylphenyl)vinyl]-1H-pyrazole, (Z)-3(5)-[2-(2-chloro-5-trifluoromethylphenyl)vinyl]-1H-pyrazole, (E)-3(5)-[2-(2-trifluoromethylphenyl)vinyl]-1H-pyrazole, (Z)-3(5)-[2-(2-trifluoromethylphenyl)vinyl]-1H-pyrazole, (E)-3(5)-[2-(2-furyl)vinyl]-1H-pyrazole, (Z)-3(5)-[2-(2-furyl)vinyl]-1H-pyrazole, (E)-3(5)-[2-(2-thienyl)vinyl]-1H-pyrazole, (Z)-3(5)-[2-(2-thienyl)vinyl]-1H-pyrazole, (E)-3-(2-(5-nitrofuran-2-yl)vinyl)-1H-pyrazole, (Z)-3-(2-(5-nitrofuran-2-yl)vinyl)-1H-pyrazole, (E)-3-styryl-1H-pyrazole, (Z)-3-styryl-1H-pyrazole, (E)-2-(2-(1H-pyrazol-3-yl)vinyl)-1H-indole, (Z)-2-(2-(1H-pyrazol-3-yl)vinyl)-1H-indole, (E)-4-(2-(1H-pyrazol-3-yl)vinyl)-N,N-dimethylaniline, (Z)-4-(2-(1H-pyrazol-3-yl)vinyl)-N,N-dimethylaniline, (E)-3-(4-methoxystyryl)-1H-pyrazole, (Z)-3-(4-methoxystyryl)-1H-pyrazole, (E)-3-(2,6-dichlorostyryl)-1H-pyrazole, (Z)-3-(2,6-dichlorostyryl)-1H-pyrazole, (E)-3-(2-(naphthalen-2-yl)vinyl)-1H-pyrazole, (Z)-3-(2-(naphthalen-2-yl)vinyl)-1H-pyrazole, (E)-3-(2-(1H-pyrrol-2-yl)vinyl)-1H-pyrazole, (Z)-3-(2-(1H-pyrrol-2-yl)vinyl)-1H-pyrazole, (E)-3-(2-(thiophen-3-yl)vinyl)-1H-pyrazole, (Z)-3-(2-(thiophen-3-yl)vinyl)-1H-pyrazole, (E)-3-(2-(1H-pyrrol-3-yl)vinyl)-1H-pyrazole, (Z)-3-(2-(1H-pyrrol-3-yl)vinyl)-1H-pyrazole, (E)-3-(2-(furan-3-yl)vinyl)-1H-pyrazole, and (Z)-3-(2-(furan-3-yl)vinyl)-1H-pyrazole. These are merely exemplary and non-limiting. Other exemplary compounds are described in U.S. Pat. No. 6,610,726.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the polyethylene glycol-polysorbate formulation described above is useful for injectable administration.

Such injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

In other embodiments, solid dosage forms of compounds embodied herein are provided. In some embodiment, such solid dosage forms have improved oral bioavailability. In one embodiment, a formulation is prepared in a solid formulation comprising about 20% (w/w) compound of the invention, about 10-20% (w/w) GELUCIRE® 44/14, about 10-20% (w/w) vitamin E succinate (TPS), 0 to about 60% polyethylene glycol 400, 0 to about 40% Lubrasol, 0 to about 15% Cremophor RH 40 (w/w), and about 1% (w/w) BHT. Formulations containing Cremophor RH 20 were liquid at room temperature but waxy solids at 4 C. The foregoing examples of one or more agents to aid in preparing formulations of inventive compound are merely illustrative and non-limiting. In certain embodiments, the compound is one of the following: (E)-3(5)-[2-(2,3-methylenedioxyphenyl)vinyl]-1H-pyrazole, (Z)-3(5)-[2-(2,3-methylenedioxyphenyl)vinyl]-1H-pyrazole, (E)-3(5)-[2-(2-chloro-5-trifluoromethylphenyl)vinyl]-1H-pyrazole, (Z)-3(5)-[2-(2-chloro-5-trifluoromethylphenyl)vinyl]-1H-pyrazole, (E)-3 (5)-[2-(2-trifluoromethylphenyl)vinyl]-1H-pyrazole, (Z)-3(5)-[2-(2-trifluoromethylphenyl)vinyl]-1H-pyrazole, (E)-3(5)-[2-(2-furyl)vinyl]-1H-pyrazole, (Z)-3(5)-[2-(2-furyl)vinyl]-1H-pyrazole, (E)-3(5)-[2-(2-thienyl)vinyl]-1H-pyrazole, (Z)-3(5)-[2-(2-thienyl)vinyl]-1H-pyrazole, (E)-3-(2-(5-nitrofuran-2-yl)vinyl)-1H-pyrazole, (Z)-3-(2-(5-nitrofuran-2-yl)vinyl)-1H-pyrazole, (E)-3-styryl-1H-pyrazole, (Z)-3-styryl-1H-pyrazole, (E)-2-(2-(1H-pyrazol-3-yl)vinyl)-1H-indole, (Z)-2-(2-(1H-pyrazol-3-yl)vinyl)-1H-indole, (E)-4-(2-(1H-pyrazol-3-yl)vinyl)-N,N-dimethylaniline, (Z)-4-(2-(1H-pyrazol-3-yl)vinyl)-N,N-dimethylaniline, (E)-3-(4-methoxystyryl)-1H-pyrazole, (Z)-3-(4-methoxystyryl)-1H-pyrazole, (E)-3-(2,6-dichlorostyryl)-1H-pyrazole, (Z)-3-(2,6-dichlorostyryl)-1H-pyrazole, (E)-3-(2-(naphthalen-2-yl)vinyl)-1H-pyrazole, (Z)-3-(2-(naphthalen-2-yl)vinyl)-1H-pyrazole, (E)-3-(2-(1H-pyrrol-2-yl)vinyl)-1H-pyrazole, (Z)-

3-(2-(1H-pyrrol-2-yl)vinyl)-1H-pyrazole, (E)-3-(2-(thiophen-3-yl)vinyl)-1H-pyrazole, (Z)-3-(2-(thiophen-3-yl)vinyl)-1H-pyrazole, (E)-3-(2-(1H-pyrrol-3-yl)vinyl)-1H-pyrazole, (Z)-3-(2-(1H-pyrrol-3-yl)vinyl)-1H-pyrazole, (E)-3-(2-(furan-3-yl)vinyl)-1H-pyrazole, and (Z)-3-(2-(furan-3-yl)vinyl)-1H-pyrazole. Other exemplary compounds are described in U.S. Pat. No. 6,610,726.

In other embodiments solid dosage forms are provided. In certain embodiments, such solid dosage forms provide a higher than about a 20% oral bioavailability. As will be shown in the examples below, compounds of the invention can be co-precipitated with one or more agents such as mannitol, a combination of mannitol and lactobionic acid, a combination of mannitol and gluconic acid, a combination of mannitol and methanesulfonic acid, a combination of microcrystalline cellulose and oleic acid or a combination of pregelatinized starch and oleic acid. The foregoing examples of one or more agents to aid in preparing formulations of inventive compound are merely illustrative and non-limiting. Non-limiting examples of inventive compounds in such solid dosage forms include (E)-3(5)-[2-(2,3-methylenedioxyphenyl)vinyl]-1H-pyrazole, (Z)-3(5)-[2-(2,3-methylenedioxyphenyl)vinyl]-1H-pyrazole, (E)-3(5)-[2-(2-chloro-5-trifluoromethylphenyl)vinyl]-1H-pyrazole, (Z)-3(5)-[2-(2-chloro-5-trifluoromethylphenyl)vinyl]-1H-pyrazole, (E)-3(5)-[2-(2-trifluoromethylphenyl)vinyl]-1H-pyrazole, (Z)-3(5)-[2-(2-trifluoromethylphenyl)vinyl]-1H-pyrazole, (E)-3(5)-[2-(2-furyl)vinyl]-1H-pyrazole, (Z)-3(5)-[2-(2-furyl)vinyl]-1H-pyrazole, (E)-3(5)-[2-(2-thienyl)vinyl]-1H-pyrazole, (Z)-3(5)-[2-(2-thienyl)vinyl]-1H-pyrazole, (E)-3-(2-(5-nitrofuran-2-yl)vinyl)-1H-pyrazole, (Z)-3-(2-(5-nitrofuran-2-yl)vinyl)-1H-pyrazole, (E)-3-styryl-1H-pyrazole, (Z)-3-styryl-1H-pyrazole, (E)-2-(2-(1H-pyrazol-3-yl)vinyl)-1H-indole, (Z)-2-(2-(1H-pyrazol-3-yl)vinyl)-1H-indole, (E)-4-(2-(1H-pyrazol-3-yl)vinyl)-N,N-dimethylaniline, (Z)-4-(2-(1H-pyrazol-3-yl)vinyl)-N,N-dimethylaniline, (E)-3-(4-methoxystyryl)-1H-pyrazole, (Z)-3-(4-methoxystyryl)-1H-pyrazole, (E)-3-(2,6-dichlorostyryl)-1H-pyrazole, (Z)-3-(2,6-dichlorostyryl)-1H-pyrazole, (E)-3-(2-(naphthalen-2-yl)vinyl)-1H-pyrazole, (Z)-3-(2-(naphthalen-2-yl)vinyl)-1H-pyrazole, (E)-3-(2-(1H-pyrrol-2-yl)vinyl)-1H-pyrazole, (Z)-3-(2-(1H-pyrrol-2-yl)vinyl)-1H-pyrazole, (E)-3-(2-(thiophen-3-yl)vinyl)-1H-pyrazole, (Z)-3-(2-(thiophen-3-yl)vinyl)-1H-pyrazole, (E)-3-(2-(1H-pyrrol-3-yl)vinyl)-1H-pyrazole, (Z)-3-(2-(1H-pyrrol-3-yl)vinyl)-1H-pyrazole, (E)-3-(2-(furan-3-yl)vinyl)-1H-pyrazole, and (Z)-3-(2-(furan-3-yl)vinyl)-1H-pyrazole. Other exemplary compounds are described in U.S. Pat. No. 6,610,726.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tabulating lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Formulations for intraocular administration are also included. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects). In non-limiting examples, one or more compounds of the invention may be formulated with at least one cytokine, growth factor or other biological, such as an interferon, e.g., alpha interferon, or with at least another small molecule compound. Non-limiting examples of pharmaceutical agents that may be combined therapeutically with compounds of the invention include: antivirals and antifibrotics such as interferon alpha, combination of interferon alpha and ribavirin, Lamivudine, Adefovir dipivoxil and interferon gamma; anticoagulants such as heparin and warfarin; antiplatelets e.g., aspirin, ticlopidine and clopidogrel; other growth factors involved in regeneration, e.g., VEGF and FGF and mimetics of these growth factors; antiapoptotic agents; and motility and morphogenic agents.

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

3) Research Uses, Clinical Uses, Pharmaceutical Uses and Methods of Treatment

Research Uses

According to the present invention, the inventive compounds may be assayed in any of the available assays known in the art for identifying compounds having the ability to modulate HGF/SF activity and in particular to agonize or mimic the activities of HGF/SF. For example, the assay may be cellular or non-cellular, in vivo or in vitro, high- or low-throughput format, etc.

Thus, in one aspect, compounds of this invention which are of particular interest include those with HGF/SF-like activity, which:

exhibit HGF/SF activity;
exhibit the ability to mimic or agonize HGF/SF activities;
stimulate cell proliferation;
exhibit anti-apoptotic activity;
exhibit antifibrotic activity;
exhibit angiogenic activity; and/or
are useful for the treatment of HGF/SF-related conditions, diseases and disorders.

Clinical Uses of Compounds with HGF/SF-Like Activity.

As noted above, effective formulations of inventive compounds described herein are useful for the treatment of the following non-limiting description of diseases and conditions. Moreover, compounds and compositions embodied herein have been found useful for treating such diseases and conditions after their onset or after the acute phase of the disease has manifest or occurred, wherein treatment starting from, or a single dose given from, hours to days after onset is found to be beneficial.

1. Fibrotic Liver Disease: Liver fibrosis is the scarring response of the liver to chronic liver injury; when fibrosis progresses to cirrhosis, morbid complications can develop. In fact, end-stage liver fibrosis or cirrhosis is the seventh leading cause of death in the United States, and afflicts hundreds of millions of people worldwide; deaths from end-stage liver disease in the United States are expected to triple over the next 10-15 years, mainly due to the hepatitis C epidemic1. In addition to the hepatitis C virus, many other forms of chronic liver injury also lead to end-stage liver disease and cirrhosis, including other viruses such as hepatitis B and delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency).

Treatment of liver fibrosis has focused to date on eliminating the primary injury. For extrahepatic obstructions, biliary decompression is the recommended mode of treatment whereas patients with Wilson's disease are treated with zinc acetate. In chronic hepatitis C infection, interferon has been used as antiviral therapies with limited response: ~20% when used alone or ~50% response when used in combination with ribavirin. In addition to the low-level of response, treatment with interferon with or without ribavirin is associated with numerous severe side effects including neutropenia, thrombocytopenia, anemia, depression, generalized fatigue and flu-like symptoms, which are sufficiently significant to necessitate cessation of therapy. Treatments for other chronic liver diseases such as hepatitis B, autoimmune hepatitis and Wilson's disease are also associated with many side effects, while primary biliary cirrhosis, primary sclerosing cholangitis and non-alcoholic fatty liver disease have no effective treatment other than liver transplantation.

The advantage of treating fibrosis rather than only the underlying etiology, is that antifibrotic therapies should be broadly applicable across the full spectrum of chronic liver diseases. While transplantation is currently the most effective cure for liver fibrosis, mounting evidence indicates that not only fibrosis, but even cirrhosis is reversible. Unfortunately patients often present with advanced stages of fibrosis and cirrhosis, when many therapies such as antivirals can no longer be safely used due to their side effect profile. Such patients would benefit enormously from effective antifibrotic therapy, because attenuating or reversing fibrosis may prevent many late stage complications such as infection, ascites, and loss of liver function and preclude the need for liver transplantation. The compounds of the invention are beneficial for the treatment of the foregoing conditions, and generally are antifibrotic and/or antiapoptotic agents for this and other organ or tissues.

2. Hepatic Ischemia-Reperfusion Injury: Currently, transplantation is the most effective therapeutic strategy for liver fibrosis. However, in spite of the significant improvement in clinical outcome during the last decade, liver dysfunction or failure is still a significant clinical problem after transplantation surgery. Ischemia-reperfusion (IR) injury to the liver is a major alloantigen-independent component affecting transplantation outcome, causing up to 10% of early organ failure, and leading to the higher incidence of both acute and chronic rejection. Furthermore, given the dramatic organ shortage for transplantation, surgeons are forced to consider cadaveric or steatotic grafts or other marginal livers, which have a higher susceptibility to reperfusion injury. In addition to transplantation surgery, liver IR injury is manifested in clinical situations such as tissue resections (Pringle maneuver), and hemorrhagic shock.

The damage to the postischemic liver represents a continuum of processes that culminate in hepatocellular injury. Ischemia activates Kupffer cells, which are the main sources of vascular reactive oxygen species (ROS) formation during the initial reperfusion period. In addition to Kupffer cell-induced oxidant stress, with increasing length of the ischemic episode, intracellular generation of ROS by xanthine oxidase and in particular mitochondria may also contribute to liver dysfunction and cell injury during reperfusion. Endogenous antioxidant compounds, such as superoxide dismutase, catalase, glutathione, alphatocopherol, and beta-carotene, may all limit the effects of oxidant injury but these systems can quickly become overwhelmed by large quantities of ROS. Work by Lemasters and colleagues, has indicated that in addition to formation of ROS, intracellular calcium dyshomeostasis is a key contributor to liver IR injury. Cell death of hepatocyte and endothelial cells in this setting is characterized by swelling of cells and their organelles, release of cell contents, eosinophilia, karyolysis, and induction of inflammation, characteristic of oncotic necrosis. More recent reports indicate that liver cells also die by apoptosis, which is morphologically characterized by cell shrinkage, formation of apoptotic bodies with intact cell organelles and absence of an inflammatory response.

Indeed, minimizing the adverse effects of IR injury could significantly increase the number of patients that may successfully undergo liver transplantation. Pharmacologic interventions that reduce cell death and/or enhance organ regeneration represent a therapeutic approach to improve clinical outcome in liver transplantation, liver surgery with vascular exclusion and trauma and can therefore reduce recipient/patient morbidity and mortality. The compounds of the invention are beneficial for the treatment of the foregoing conditions.

3. Cerebral Infarction. Stroke and cerebrovascular disease are a leading cause of morbidity and mortality in the US: at least 600,000 Americans develop strokes each year, and about 160,000 of these are fatal. Research on the pathophysiological basis of stroke has produced new paradigms for prevention and treatment, but translation of these approaches into improved clinical outcomes has proved to be painfully slow. Preventive strategies focus primarily on reducing or controlling risk factors such as diabetes, hypertension, cardiovascular disease, and lifestyle; in patients with severe stenosis, carotid endarterectomy may be indicated. Cerebral angioplasty is used investigationally, but the high restenosis rates observed following coronary angioplasty suggest this approach may pose unacceptable risk for many patients. Therapeutic strategies focus primarily on acute treatment to reduce injury in the ischemic penumbra, the region of reversibly damaged tissue surrounding an infarct. Thrombolytic therapy has been shown to improve perfusion to the ischemic penumbra, but it must be administered within three hours of the onset of infarction. Several neuroprotective agents that block specific tissue responses to ischemia are promising, but none have yet been approved for clinical use. While these therapeutic approaches limit damage in the ischemic penumbra, they do not address the underlying problem of inadequate blood supply due to occluded arteries. An alternative strategy is to induce formation of collateral blood vessels in the ischemic region;

this occurs naturally in chronic ischemic conditions, but stimulation of vascularization via therapeutic angiogenesis has potential therapeutic benefit.

Recent advances in imaging have confirmed the pathophysiological basis of the clinical observations of evolving stroke. Analysis of impaired cerebral blood flow (CBF) in the region of an arterial occlusion supports the hypothesis that a central region of very low CBF, the ischemic core, is irreversibly damaged, but damage in surrounding or intermixed zones where CBF is of less severely reduced, the ischemic penumbra, can be limited by timely reperfusion. Plate recently reviewed the evidence suggesting that therapeutic angiogenesis may be useful for treatment or prevention of stroke. First, analysis of cerebral vasculature in stroke patients showed a strong correlation between blood vessel density and survival and a higher density of microvessels in the ischemic hemisphere compared to the contralateral region. Second, studies in experimental models of cerebral ischemia indicate expression of angiogenic growth factors such as vascular endothelial growth factor (VEGF) or HGF/SF is induced rapidly in ischemic brain tissue. Third, administration of VEGF or HGF/SF can reduce neuronal damage and infarct volume in animal models. Similar evidence provided the rationale for developing therapeutic angiogenesis for treating peripheral and myocardial ischemia, which has been shown to produce clinical improvements in early studies in humans. The compounds of the invention are beneficial for the treatment of the foregoing conditions.

4. Ischemic heart disease is a leading cause of morbidity and mortality in the US, afflicting millions of Americans each year at a cost expected to exceed $300 billion/year. Numerous pharmacological and interventional approaches are being developed to improve treatment of ischemic heart disease including reduction of modifiable risk factors, improved revascularization procedures, and therapies to halt progression and/or induce regression of atherosclerosis. One of the most exciting areas of research for the treatment of myocardial ischemia is therapeutic angiogenesis. Recent studies support the concept that administration of angiogenic growth factors, either by gene transfer or as a recombinant protein, augments nutrient perfusion through neovascularization. The newly developed, supplemental collateral blood vessels constitute endogenous bypass conduits around occluded native arteries, improving perfusion to ischemic tissue. Some of the best-studied cytokines with angiogenic activity are vascular endothelial growth factor (VEGF), basic fibroblast growth factor (bFGF) and hepatocyte growth factor/scatter factor (HGF/SF). The compounds of the invention are beneficial for the treatment of the foregoing conditions.

5. Renal Disease. Chronic renal dysfunction is a progressive, degenerative disorder that ultimately results in acute renal failure and requires dialysis as an intervention, and renal transplantation as the only potential cure. Initiating conditions of renal dysfunction include ischemia, diabetes, underlying cardiovascular disease, or renal toxicity associated with certain chemotherapeutics, antibiotics, and radiocontrast agents. Most end-stage pathological changes include extensive fibrinogenesis, epithelial atrophy, and inflammatory cell infiltration into the kidneys.

Acute renal failure is often a complication of diseases including diabetes or renal ischemia, procedures such as heminephrectomy, or as a side effect of therapeutics administered to treat disease. The widely prescribed anti-tumor drug cis-diamminedichloroplatinum (cisplatin), for example, has side effects that include a high incidence of nephrotoxicity and renal dysfunction, mainly in the form of renal tubular damage that leads to impaired glomerular filtration. Administration of gentamicin, an aminoglycoside antibiotic, or cyclosporin A, a potent immunosuppressive compound, causes similar nephrotoxicity. The serious side effects of these effective drugs restrict their use. The development of agents that protect renal function and enhance renal regeneration after administration of nephrotoxic drugs will be of substantial benefit to numerous patients, especially those with malignant tumors, and may allow the maximal therapeutic potentials of these drugs to be realized. The compounds of the invention are beneficial for the treatment of the renal diseases mentioned above.

6. Lung (Pulmonary) Fibrosis. Idiopathic pulmonary fibrosis (IPF) accounts for a majority of chronic interstitial lung diseases, and has an estimated incidence rate of 10.7 cases for 100,000 per year, with an estimated mortality of 50-70%. IPF is characterized by an abnormal deposition of collagen in the lung with an unknown etiology. Although the precise sequence of the pathogenic sequelae is unknown, disease progression involves epithelial injury and activation, formation of distinctive subepithelial fibroblast/myofibroblast foci, and excessive extracellular matrix accumulation. The development of this pathological process is preceded by an inflammatory response, often dominated by macrophages and lymphocytes, which is mediated by the local release of chemoattractant factors and upregulation of cell-surface adhesion molecules. Lung injury leads to vasodilatation and leakage of plasma proteins into interstitial and alveolar spaces, as well as activation of the coagulation cascade and deposition of fibrin. Fibroblasts migrate into this provisional fibrin matrix where they synthesize extracellular matrix molecules. In non-pathogenic conditions, excess fibrin is usually degraded by plasmin, a proteinase that also has a role in the activation of matrix metalloproteinases (MMPs). Activated MMPs degrade extracellular matrix and participate in fibrin removal, resulting in the clearance of the alveolar spaces and the ultimate restoration of injured tissues. In pathological conditions, however, these processes can lead to progressive and irreversible changes in lung architecture, resulting in progressive respiratory insufficiency and an almost universally terminal outcome in a relatively short period of time. Fibrosis is the final common pathway of a variety of lung disorders, and in this context, the diagnosis of pulmonary fibrosis implies the recognition of an advanced stage in the evolution of a complex process of abnormal repair. While many studies have focused on inflammatory mechanisms for initiating the fibrotic response, the synthesis and degradation the extracellular matrix represent the central event of the disease. It is this process that presents a very attractive site of therapeutic intervention.

The course of IPF is characterized by progressive respiratory insufficiency, leading to death within 3 to 8 years from the onset of symptoms. Management of interstitial lung disease in general, and in particular idiopathic pulmonary fibrosis, is difficult, unpredictable and unsatisfactory. Attempts have been made to use antiinflammatory therapy to reverse inflammation, relief, stop disease progression and prolong survival. Corticosteroids are the most frequently used antiinflammatory agents and have been the mainstay of therapy for IPF for more than four decades, but the efficacy of this approach is unproven, and toxicities are substantial. No studies have compared differing dosages or duration of corticosteroid treatment in matched patients. Interpretation of therapy efficacy is obscured by several factors including heterogeneous patient populations, inclusion of patients with histologic entities other than usual interstitial pneumonia, lack of objective, validated endpoints, and different criteria for "response." Cytotoxic drugs such as Azathioprine and cyclophosphamide have also been used in combination with low dose oral corticosteroids. The results of such treatments vary from no improvement to significant prolongation of survival. Overall, currently available treatments for lung fibrosis are sub-optimal. Potential new therapies have emerged from the use of animal models of pulmonary fibrosis and recent advances in the cellular and molecular biology of inflammatory reactions. Such therapies involve the use of cytokines, oxidants and growth factors that are elaborated during the fibrotic reaction. Despite the use of newer strategies for treatment, the overall prognosis for patients with interstitial lung disease has had little quantifiable change, and the population survival remains unchanged for the last 30 years. Interferon gamma (IFN) may be effective in the treatment of IPF in some patients but its role is controversial. Literature indicated that IFN-gamma may be involved in small airway disease in silicosis lung. Others showed that IFN gamma mediates, bleomycin-induced pulmonary inflammation and fibrosis. Recently, hepatocyte growth factor (HGF), also known as scatter factor (SF) has emerged as a attractive target for the development of antifibrotic agents. The compounds of the invention are beneficial for the treatment of the foregoing condition, among other fibrotic diseases.

Exemplary Assays

Efficacy of the compounds of the invention on the aforementioned disorders and diseases or the potential to be of benefit for the prophylaxis or treatment thereof may be demonstrated in various studies, ranging from biochemical effects evaluated in vitro and effects on cells in culture, to in-vivo models of disease, wherein direct clinical manifestations of the disease can be observed and measured, or wherein early structural and/or functional events occur that are established to be involved in the initiation or progression of the disease. The positive effects of the compounds of the invention have been demonstrated in a variety of such assays and models, for a number of diseases and disorders. One skilled in the art can readily determine following the guidance described herein whether a compound of the invention is an HGF/SF mimic and is useful therapeutically in the same manner as HGF/SF, or is an antagonist and is useful where the activities of HGF/SF are not desired or are to be inhibited.

1. In Vitro Stimulation of Proliferation and Scatter a. Endothelial cell proliferation. Proliferation of human umbilical vein endothelial cells and monkey bronchial epithelial cells ([$^3$H]-thymidine incorporation) by compounds of the invention produce a response similar to that of HGF/SF.

b. Renal cell scatter. The ability to scatter cultured MDCK cells is highly specific for compounds with HGF/SF activity. Compounds of the invention scatter MDCK cells in a manner similar to HGF/SF.

2. Cellular Signaling a. Phosphorylation of c-met. In both human umbilical vein endothelial cells (HUVECs) and MDCK cells the instant compounds induce phosphorylation of c-met in a dose-dependent manner similar to HGF/SF. The assay is performed by immunoprecipitation of phosphorylated c-met followed by SDS-PAGE and chemiluminescence detection, standardized to total c-met.

b. Intracellular signaling induced by compounds of the invention and HGF/SF. In HUVECs the compounds induce phosphorylation of extracellular receptor kinase (ERK) (as determined by immunoprecipitation followed by SDS-PAGE and chemiluminescence) similar to HGF/SF. In addition, the phosphoinositide 3-kinase inhibitor wortmannin and an Akt inhibitor prevents compound- and HGF/SF-induced endothelial cell proliferation, suggesting that both the instant compounds and HGF/SF exert biological effects through the same intracellular signaling pathways.

c. HGF and compounds of the invention stimulate nitric oxide production in endothelial cells. HUVECs are incubated with either vehicle, HGF/SF, instant compounds, or SNAP for 24 hours, loaded with the nitric oxide-sensitive fluorescence indicator DAF2-DA and imaged under a laser scanning confocal microscope. HGF/SF, instant compounds and SNAP all cause a significant increase in fluorescence indicating robust production of nitric oxide.

3. Anti-Apoptotic Activity a. HGF/SF and instant compounds have significant anti-apoptotic activity in cultured cell lines. Like HGF/SF, the compounds are able to significantly block adriamycin-induced apoptosis in MDCK cells. Pretreatment with either HGF/SF or compound significantly improves the cell viability of both HUVEC and MDCK cell lines.

b. Protection from apoptosis in NIH-3T3 cells transfected with c-met receptor. NIH-3T3 cells transfected with the gene for the c-met receptor confers the ability for both HGF/SF and compounds of the invention to protect the cells from adriamycin-induced apoptosis (MTT assay). There is no protection from apoptosis by compounds in non-transfected cells lacking the c-met receptor, demonstrating the requirement of c-met for the cyto-protective actions of HGF/SF and instant compounds.

4. Angiogenesis a. Aortic ring assay. Thoracic artery rings from rats are embedded in Matrigel and grown for 5 days in the presence or absence of HGF/SF or compounds of the invention. Treatment with compounds of the invention causes an increased outgrowth from the rings similar to that seen with HGF/SF.

b. In vivo Matrigel assay. Matrigel mixed with a compound of the invention or vehicle is injected into the abdominal subcutaneous tissue of C57BL/6 mice. When harvested 10 days later, the compound is found to induce blood vessel formation into the Matrigel plugs, demonstrating that the compound can exert its angiogenic effects in vivo.

c. Mouse hindlimb ischemia model. In a mouse hindlimb ischemia model treatment with a compound of the invention produces greater recovery of hindlimb blow flow (as measured by laser Doppler imaging). Improved flux is associated with an increased number of capillaries in the ischemic muscle.

d. Hindlimb ischemia in non-obese diabetic (NOD) mice. In female NOD mice subjected to hindlimb ischemia, hindlimb blood flow (measured using a Laser Doppler imager) demonstrates recovery by administration of a compound of the invention.

e. Angiogenesis in full-thickness cutaneous wounds. In full thickness cutaneous wounds in pigs significant increases are observed in capillary numbers after treatment with a compound of the invention, or Ad5-HGF/SF (an adenoviral vector expressing the gene for HGF/SF).

5. Hepatic Disease a. Antifibrotic Activity in Hepatic Stellate Cells. Serum starved (activated) LX2 cells (an immortalized human hepatic stellate cell line) that are treated with HGF/SF or a compound of the invention show a decrease in collagen I mRNA expression, as well as expression of other fibrotic marker genes, related to significant antifibrotic activity.

b. Liver Disease endpoints. The rat model of thioacetamide (TAA)-induced liver fibrosis and the rat bile duct ligation model of fibrosis showed improvements by the compounds of the invention, in a panel of functional and histological tests: gross morphology, mass, portal pressure, presence of ascites, enzymes (AST, ALT), collagen content, interstitial fibrosis and alpha-smooth muscle actin and MMP-2. Delayed treatment from the time of induction of disease shows significant benefit.

6. Protection Against Renal Dysfunction a. Clinical model: arterial occlusion. In a mouse model of transient unilateral renal artery occlusion, male ICR mice were anesthetized and the left renal artery occluded with a microvascular clamp. After 30 minutes, the clamp was removed and the kidney allowed to reperfuse. Ten minutes into reperfusion the nonischemic contralateral kidney was excised. Animals were treated daily with vehicle or compound of the invention (1 mg/kg, i.p.) until the day of sacrifice. Serum creatinine, BUN and urine protein levels, measured at 1, 4 and 7 days postischemia were used to determine the ability of compounds of the invention to restore function to injured kidneys. In order to create a more severe renal injury, animals were subjected to 45 minutes of ischemia. In other models, permanent ligation/nephrectomy is carried out. Immediate as well as delayed treatment with embodied compounds is beneficial.

b. Protection against $HgCl_2$-induced renal injury. In a study mice were injected with a high dose of $HgCl_2$ (7 mg/kg, s.c.) and divided into treatment groups. Animals in the first group received vehicle or a compound of the invention (1 mg/kg, i.p.) on the day of toxin injection and daily thereafter for 3 days, and were euthanized on day 4. Blood samples collected prior to $HgCl_2$ injection, on day 2 and on day 4 were analyzed for serum creatinine. In the second group, treatment with vehicle or compound began on the day following toxin injection (i.e., 24 h delayed treatment) and daily thereafter until day 6. Mice were euthanized on day 7. Blood samples collected prior to $HgCl_2$ injection, on day 4 and day 7 were analyzed for serum creatinine and BUN. Serum creatinine, BUN, and development of tubular necrosis were measured to indicate positive clinical activity.

c. Protection against urethral obstruction. The effects of the compounds of invention on renal injury secondary to ureteral obstruction were examined in a mouse model of transient unilateral renal artery occlusion. Kidneys from mice subjected to unilateral ureteral obstruction for 2 weeks were examined for histological evidence of injury and protection by compound treatment. Immunohistochemical staining was performed for fibronectin, proliferating cell nuclear antigen, and TUNEL (for an assessment of apoptosis). Trichrome staining was also performed to assess the extent of collagen formation as an indication of interstitial fibrosis.

7. Cerebral Infarction/Stroke a. Neuroprotective Effects in Brain Tissue. Cerebral infarction was induced in rats by middle cerebral artery occlusion (MCAO) for 24 hr. Test compound or vehicle was administered by i.p. at 2 mg/kg at −24, 0, and 8 hr. Sections of the brain were then examined for cell death by staining with a tetrazolium compound (2,3,5-Triphenyl-2H-tetrazolium chloride, or TTC). Normal rat brains exhibit a red staining due to TTC reduction whereas areas containing dead cells are white.

8. Myocardial Infarction a. Ability of the compounds of the invention to inhibit apoptosis in a rat model of myocardial infarction (as mentioned above). Hearts from rats subjected to left coronary artery ligation are treated with compound (or vehicle control) by direct injection and 24 hours later sectioned and TUNEL stained. There is a significant reduction in the number of apoptotic nuclei in rats treated with compound.

b. Clinical model. In a rat ischemia model, myocardial infarction was induced by anterior descending artery occlusion. The infarction was evident by an increase in positive TUNEL staining, indicating DNA fragmentation in late-stage apoptosis. Treatment with compounds of the invention greatly reduced the extent of TUNEL staining.

c. Clinical model with delayed treatment. Treatment delayed for 24 hours after myocardial ischemia reduces infarct size.

9. Transplantation and Organ Preservation a. The viability of organs and tissues harvested and transported for transplant is currently optimally maintained by bathing and transport in storage solutions such as the University of Wisconsin (UW) cold storage solution (100 mM $KH_2PO_4$, 5 mM $MgSO_4$ 100 mM potassium lactobionate, 1 mM allopurinol, 3 mM glutathione, 5 mM adenosine, 30 mM raffinose, 50 g/liter of hydroxyethyl starch, 40 units/liter of insulin, 16 mg/liter of dexamethasone, 200,000 units/liter of penicillin, pH 7.4; 320-330 mOsM) (Ploeg R J, Goossens D, Vreugdenhil P, McAnulty J F, Southard J H, Belzer F O. Successful 72-hour cold storage kidney preservation with U W solution. Transplant Proc. 1988 February; 20(1 Suppl 1):935-8.). To further enhance the viability of transplanted organs and tissues, inhibit apoptosis and promote vascularization thereof, one or more compounds of the invention may in included in this or any other storage solution, as well as perfused into the donor or donor organ prior to harvesting, and administered to the recipient systemically and/or locally into the transplanted organ or transplant site.

10. Lung Fibrosis

In order to assess the effects of C6 on pulmonary fibrosis we used a well-established mouse model of bleomycin-induced lung injury. Male C57BL/6 mice (20-30 g, n=10/group) were treated with bleomycin (0.06 U/20 gram body weight) or saline via intratracheal administration. Bleomycin-treated mice were divided into 2 groups. Compounds of the invention (1 mg/kg, i.p.) or vehicle was administered daily until sacrifice on day 12. Right lung samples from the mice were then harvested for analysis. Tissues were sectioned and stained with modified Masson's Trichrome and analyzed for interstitial fibrosis. The Ashcroft scale was used to obtain a numerical fibrotic score with each specimen being scored independently by two histopathologists, and the mean of their individual scores considered as the fibrotic score.

11. Diabetes Mellitus a. Compounds of the invention reduces hyperglycemia in diabetic mice. Normal CD-1 mice were induced to develop hyperglycemia (diabetes) by i.v. injection with 100 mg/kg streptozotocin (STZ) followed by measurement of blood glucose in a week. The animals were treated with test compound at 2 mg/kg or vehicle daily starting the same day of STZ injection. Glucose samples were taken from the tail vein at day 7 with Ascensia ELITE blood glucose test strips (Bayer), and the blood glucose concentration was determined by glucose meters (Bayer). STZ induced diabetes, as shown by a significant increase in blood glucose levels compared to that in normal mice. Compounds of the invention reduced blood glucose levels.

12. Muscular dystrophy. In a genetic murine muscular dystrophy model, two months of intraperitoneal administration of a compound embodied herein reduced the elevation in creatine kinase, indicating a beneficial effect on the disease.

13. Amyotrophic lateral sclerosis. In SODG93A mouse model of ALS, daily compound administration starting at age 94 days (when neurofilament degeneration typically occurs) through day 122 significantly improved hindlimb pathology score vs. In addition, a stride test showed that treated animals showed improvement. Survival of the treated animals was also significantly (p<0.05) extended vs. vehicle-treated animals.

As detailed in the exemplification herein, in assays to determine the ability of compounds to stimulate cell growth among other HGF/SF-like activities measured in vitro, certain inventive compounds exhibited $ED_{50}$ values ≤50 µM. In certain other embodiments, inventive compounds exhibit $ED_{50}$ values ≤40 µM. In certain other embodiments, inventive compounds exhibit $ED_{50}$ values ≤30 µM. In certain other embodiments, inventive compounds exhibit $ED_{50}$ values ≤20 µM. In certain other embodiments, inventive compounds exhibit $ED_{50}$ values ≤10 M. In certain other embodiments, inventive compounds exhibit $ED_{50}$ values ≤7.5 M. In certain embodiments, inventive compounds exhibit $ED_{50}$ values ≤5 µM. In certain other embodiments, inventive compounds exhibit $ED_{50}$ values ≤2.5 µM. In certain embodiments, inventive compounds exhibit $ED_{50}$ values ≤1 µM. In certain other embodiments, inventive compounds exhibit $ED_{50}$ values ≤750 nM. In certain other embodiments, inventive compounds exhibit $ED_{50}$ values ≤500 nM. In certain other embodiments, inventive compounds exhibit $ED_{50}$ values ≤250 nM. In certain other embodiments, inventive compounds exhibit $ED_{50}$ values ≤100 nM. In other embodiments, exemplary compounds exhibited $ED_{50}$ values ≤75 nM. In other embodiments, exemplary compounds exhibited $ED_{50}$ values ≤50 nM. In other embodiments, exemplary compounds exhibited $ED_{50}$ values ≤40 nM. In other embodiments, exemplary compounds exhibited $ED_{50}$ values ≤30 nM. In other embodiments, exemplary compounds exhibited $ED_{50}$ values ≤20 nM. In other embodiments, exemplary compounds exhibited $ED_{50}$ values ≤10 nM. In other embodiments, exemplary compounds exhibited $ED_{50}$ values ≤5 nM.

Pharmaceutical Uses and Methods of Treatment

As discussed above, compositions and formulations comprising compounds as described herein exhibit activity generally as modulators of HGF/SF activity. More specifically, compounds of the invention demonstrate the ability to agonize HGF/SF activity. Thus, in certain embodiments, compositions of the invention are useful for the treatment of any of a number of conditions or diseases in which HGF/SF or the activities thereof have a therapeutically useful role, in particular antifibrotic, angiogenic and antiapoptotic activities. Thus, compounds of the invention are useful for the treatment of any condition, disease or disorder in which HGF/SF would have a beneficial role.

Accordingly, in another aspect of the invention, methods for the treatment of HGF/SF activity related disorders are provided comprising administering a therapeutically effective amount of a composition or formulation comprising a compound of formula (I), (II) or (III) as described herein, to a subject in need thereof. In certain embodiments, a method for the treatment of HGF/SF activity related disorders is provided comprising administering a therapeutically effective amount of an inventive composition or formulation, or a pharmaceutical composition comprising an inventive compound to a subject in need thereof, in such amounts and for such time as is necessary to achieve the desired result.

In certain embodiments, the method involves the administration of a therapeutically effective amount of the compound or a pharmaceutically acceptable derivative thereof to a subject (including, but not limited to a human or animal) in need of it. Subjects for which the benefits of the compounds of the invention are intended for administration include, in addition to humans, livestock, domesticated, zoo and companion animals.

As discussed above this invention provides novel compounds that have biological properties useful for modulating, and preferably mimicking or agonizing, HGF/SF activity. In certain embodiments, the inventive compounds are useful for the treatment of wounds for acceleration of healing (wound healing may be accelerated by promoting cellular proliferation, particularly of vascular cells), normalization of myocardial perfusion as a consequence of chronic cardiac ischemia or myocardial infarction, development or augmentation of collateral vessel development after vascular occlusion or to ischemic tissues or organs, fibrotic diseases, hepatic disease including fibrosis and cirrhosis, lung fibrosis, renal failure, renal fibrosis, cerebral infarction (stroke), diabetes mellitus, and vascularization of grafted or transplanted tissues or organs. Renal conditions for which compounds of the invention may prove useful include: radiocontrast nephropathy; fibrosis secondary to renal obstruction; indication for renal trauma and transplantation; renal failure secondary to chronic diabetes and/or hypertension.

Thus, as described above, in another aspect of the invention, a method for the treatment of disorders related to HGF/SF activity is provided comprising administering a therapeutically effective amount of a composition comprising a compound of formula (I), (II) or (III) as described herein, to a subject in need thereof. In certain embodiments of special interest the inventive method is used for the treatment of, in the case of HGF/SF agonists or mimics, hepatic disease, stroke, myocardial infarction and other ischemic or fibrotic diseases; and in the case of HGF/SF antagonists, cancer or other dysproliferative diseases. In certain embodiments, compounds of Formula II are HGF/SF agonists or mimics. In another aspect, agonists may be used to preserve organs and tissues identified for transplantation, and may be infused into the donor, perfused into the harvested organs and tissues or provided as a bath, and administered to the recipient. It will be appreciated that the compounds and compositions, according to the method of the present invention, may be administered using any amount and any route of administration effective for the treatment of conditions or diseases in which HGF/SF or the activities thereof have a therapeutically useful role. Thus, the expression "effective amount" as used herein, refers to a sufficient amount of agent to modulate HGF/SF activity (e.g., mimic HGF/SF activity), and to exhibit a therapeutic effect. The exact amount required will vary from subject to subject, depending on the species, age, and general condition of the subject, the severity of the infection, the particular therapeutic agent, its mode and/or route of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In another embodiment, compounds of the invention as well as compositions and formulations thereof are therapeutically beneficial when administered at a time after the onset of the acute disease or acute condition or time of injury. In certain instances administration at least 3 hours after onset is beneficial. In other embodiments administration at least 24 hours after onset is beneficial. In certain other embodiments administration at least 1-3 weeks after onset is beneficial. In other embodiments methods are provided for treating an acute disease or condition wherein compound is administered at a time after the onset or induction of the disease or condition. In other embodiments, temporal separation of the induction, onset, recurrence or recrudescence of a disease or injury, and the optimal effective response to an HGF mimetic, provides guidance to the timing of administration of a compound of the invention or a composition of formulation thereof.

In another embodiment, the timing of single or multiple administrations of a compound of the invention is coordinated with the expression of the HGF receptor, c-Met. In another embodiment, c-Met expression is delayed from the time of onset of the disease or condition, for several hours to up to 24-48 hours afterwards. In another embodiment, the kinetics of c-Met receptor expression and the pharmacokinetics of inventive compound are coordinated such that peak or near peak circulating levels of inventive compound are present at the peak or near expression of c-Met. In one embodiment, the expression of c-Met following acute myocardial infarction is 24-48 hours.

In particular, benefit in treating chronic diseases is found using inventive compounds and compositions. As will be seen in the examples below, diseases such as myocardial infarction, heart failure and renal failure can be treated with inventive compounds starting after the initial onset or induction of the disease or injury, from hours to days or even weeks later in particular for chronic diseases, and exhibit a beneficial effect on the course of the disease. This, in one embodiment, a large therapeutic window of opportunity exists for successful treatment of injuries, conditions and diseases with the compounds and compositions thereof embodied herein.

In one embodiment, myocardial infarction is treated with a compound or composition of the invention starting about 3 hours after the appearance of symptoms. In another embodiment, myocardial infarction is treated with a compound of composition of the invention starting about 6 hours after the appearance of symptoms. In another embodiment, myocardial infarction is treated with a compound of composition of the invention starting about 12 hours after the appearance of symptoms. In another embodiment, myocardial infarction is treated with a compound of composition of the invention starting about 24 hours after the appearance of symptoms. In another embodiment, myocardial infarction is treated with a compound of composition of the invention starting about 48 hours after the appearance of symptoms. In another embodiment, treatment starting from the delayed time point can continue on a regular bases thereafter, such as starting at 48 hours after myocardial infarction and continuing daily. Such delayed treatment is shown to intervene in the cardiac remodeling process following a heart attack, and ameliorate chronic heart failure.

In one embodiment, renal failure is treated with a compound or composition of the invention starting about 24 hours after the appearance of symptoms. In another embodiment, renal failure is treated with a compound of composition of the invention starting about 48 hours after the appearance of symptoms. In another embodiment, renal failure is treated with a compound of composition of the invention starting about 72 hours after the appearance of symptoms. In another embodiment, renal failure is treated with a compound of composition of the invention starting about 96 hours after the appearance of symptoms. In another embodiment, renal failure is treated with a compound of composition of the invention starting about 24 hours after the appearance of symptoms, and again at 48 hours. In another embodiment, renal failure is treated with a compound of composition of the invention starting about 24 hours after the appearance of symptoms, then again at 48 hours and 72 hours. In another embodiment, renal failure is treated with a compound of composition of the invention starting about 24 hours after the appearance of symptoms, then again at 48 hours, 72 hours and 96 hours. In another embodiment, treatment starting from the delayed time point can continue on a regular bases thereafter, such as starting at 24 hours after myocardial infarction and continuing daily. Such delayed treatment is shown to intervene in the development of renal failure.

In another embodiment, compounds embodied herein as well as their compositions and formulations are useful for treating amyotrophic lateral sclerosis (ALS or Lou Gehrig's disease). As will be shown in the examples below, compounds embodied herein were found to interfere with disease progressing in the SOD$^{G93A}$ mouse model of ALS. Using a hindlimb clinical observation score, compound treatment significantly improved the pathology score vs. the vehicle-treated cohort. In addition, a stride test showed that treated animals showed improvement. Survival of the treated animals was also significantly extended vs. vehicle-treated animals.

In another embodiment, compounds embodied herein as well as their compositions and formulations are useful for treating muscular dystrophy. As shown in a genetic model of the disease, compound administration reduced creatine kinase levels indicating amelioration of the disease.

In another embodiment, delayed, oral administration of formulations of compounds embodied herein were found to be beneficial in chronic kidney disease (CKD), using a 5/6 left nephrectomy and excision of the right kidney. Oral administration of compound was found to be therapeutic in CKD, attenuating mortality, reducing proteinuria and kidney collagen content. In another study, daily oral treatment starting 2 weeks after surgery and continued for 10 weeks showed increased survival (80%) vs. untreated animals (45%), and a dose-responsive reduction in kidney collagen content.

In another embodiment, oral administration of compounds embodies herein attenuated the appearance of proteinuria in metabolic syndrome. Using three-month old obese male ZSF1 rats, 10 days of treatment resulted in a significantly reduced 24-hour proteinuria Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, subcutaneously, intradermally, intraocularly, topically (as by powders, ointments, or drops), buccally, as an oral or nasal spray, or the like, depending on the severity of the disease or disorder being treated. In certain embodiments, the compounds of the invention may be administered at dosage levels of about 0.001 mg/kg to about 50 mg/kg, preferably from about 0.1 mg/kg to about 10 mg/kg for parenteral administration, or preferably from about 1 mg/kg to about 50 mg/kg, more preferably from about 10 mg/kg to about 50 mg/kg for oral administration, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Moreover, pharmaceutical compositions comprising one or more compounds of the invention may also contain other compounds or agents for which co-administration with the compound(s) of the invention is therapeutically advantageous. As many pharmaceutical agents are used in the treatment of the diseases and disorders for which the compounds of the invention are also beneficial, any may be formulated together for administration. Synergistic formulations are also embraced herein, where the combination of at least one compound of the invention and at least one other compounds act more beneficially than when each is given alone. Non-limiting examples of pharmaceutical agents that may be combined therapeutically with compounds of the invention include (non-limiting examples of diseases or conditions treated with such combination are indicated in parentheses): antivirals and antifibrotics, such as interferon alpha (hepatitis B, and hepatitis C), combination of interferon alpha and ribavirin (hepatitis C), Lamivudine (hepatitis B), Adefovir dipivoxil (hepatitis B), interferon gamma (idiopathic pulmonary fibrosis, liver fibrosis, and fibrosis in other organs); anticoagulants, e.g., heparin and warfarin (ischemic stroke); antiplatelets e.g., aspirin, ticlopidine and clopidogrel (ischemic stroke); other growth factors involved in regeneration, e.g., VEGF and FGF and mimetics of these growth factors; antiapoptotic agents; and motility and morphogenic agents.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a well-established literature of small molecule chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

1) Synthesis of Exemplary Compounds:

Unless otherwise indicated, starting materials are either commercially available or readily accessibly through laboratory synthesis by anyone reasonably familiar with the art. Described generally below, are procedures and general guidance for the synthesis of compounds as described generally and in subclasses and species herein. In addition, synthetic guidance can be found in Kinoshita, M. et al. Bull. Chem. Soc. Jpn. 1987, 60, 2151-2162; Natchev, I. A. Tetrahedron 1988, 44, 1511-1522; Almirante, N. et al. Tetrahedron Lett. 1998, 39, 3287; and Bellassoued and Majidi, J. Org. Chem. 1993, 58, 2517-2522; the entire contents of which are hereby incorporated by reference.

Mono-Substituted Pyrazoles (C(3) and C(5) Tautomers)

The skilled practitioner will recognize that C(3)- and C(5)-substituted 1H-pyrazole tautomers typically exist as mixtures which rapidly interconvert in solution. Because of this rapid proton transfer, 3- and 5-substituted pyrazole tautomers do not normally have separate existence. The tautomers may, however, exist in solution predominantly in one form. See, for example, T. L. Gilchrist, "Heterocyclic Chemistry" 2nd Edition, Longman Scientific and Technical, 1992; p 287; which is incorporated herein by reference.

Thus, the synthetic guidance provided herein is relevant to both 3- and 5-substituted pyrazole tautomers.

In certain exemplary embodiments, compounds of formula (II) where $R^3$ is —CH═CH—R may be prepared as follows:

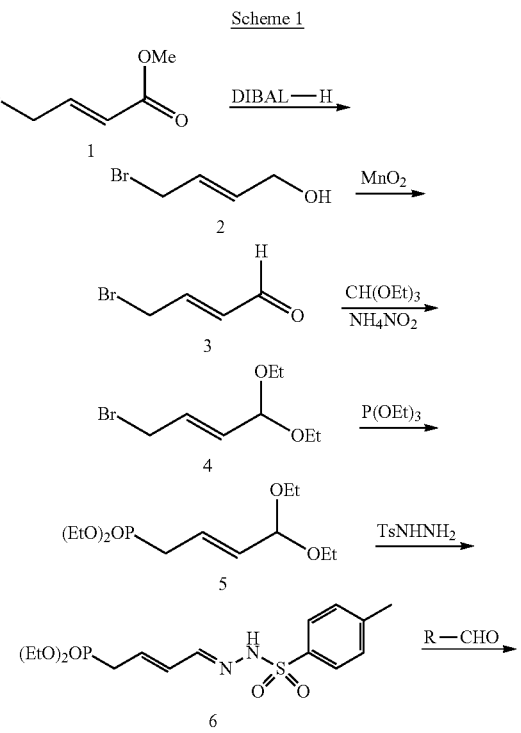

Scheme 1

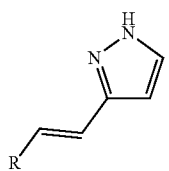

For example, the preparation of 4-bromocrotonaldehyde (3) may be achieved using a modification of a literature method (Kinoshita, M. et al. *Bull. Chem. Soc. Jpn.* 1987, 60, 2151-2162). Conversion of 3 to 4 may be carried out using the method described in the literature (Natchev, I. A. *Tetrahedron* 1988, 44, 1511-1522), involving treatment of aldehydes 3 with triethylorthoformate in the presence of ammonium nitrate. The crude product may be purified by distillation. Conversion of 4 to 5 may be conducted as described by Natchev. As above, the product may be purified by distillation. Conversion of 5 to the final desired reagent 6 may be accomplished using known methods (See, for example, Almirante, N. et al. *Tetrahedron Lett.* 1998, 39, 3287).

An alternate procedure with easier purification methods and higher yields is described by Bellassoued and Majidi (*J. Org. Chem.* 1993, 58, 2517-2522), illustrated in Scheme 2. Treatment of an aldehyde with reagent 7 in the presence of 0.1 equiv. ZnBr gave the vinylogous aldehydes (acrylaldehydes), in yields ranging from 65% to 95%. Reagent 7 is commercially available.

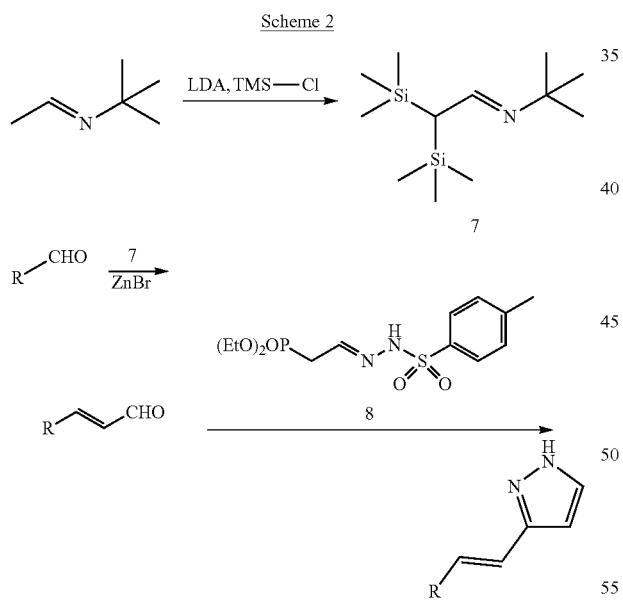

In certain embodiments, new analogues were prepared using a two-step synthetic method beginning with aryl aldehydes (R—CHO, Scheme 2). Vinylogation of the aryl aldehydes was achieved via treatment with α,α-bis(trimethylsilyl)-t-butylacetaldimine (7) in the presence of ZnBr$_2$, as described in the literature (Bellassoued, M.; Majidi, A. *J. Org. Chem.* 1993, 58, 2517), to afford the 3-arylacrylaldehydes R—CH=CH—CHO. The 3-arylacrylaldehydes were converted to the final products via treatment with diethoxyphosphorylacetaldehyde tosylhydrazone (8), as described in the literature (Almirante, N.; Cerri, A.; Fedrizzi, G.; Marazzi, G.; Santagostino, M. *Tetrahedron Lett.* 1998, 39, 3287).

It will be appreciated that the two-step reaction sequence illustrated in Scheme 2 is general in nature, and one skilled in the art will recognize that the method could be used to prepare analogues in which R represents virtually any type of aryl, alkyl, heteroaryl, or heterocyclic functional group. The following represent non-limiting examples of the synthetic method, and are illustrated in FIG. 1 below.

Example 1.
3-(2,3-methylenedioxyphenyl)acrylaldehyde

To a solution of 2,3-methylenedioxybenzaldehyde (150 mg) in 5 mL THF was added 22 mg of ZnBr$_2$. With stirring, 250 mg of α,α-bis(trimethylsilyl)-t-butylacetaldimine (7) was added, and stirring was continued overnight. The solution was cooled to 10° C., then hydrolyzed by the addition of a solution of ZnCl$_2$ (22 mg) in diethyl ether/water (5 mL each), followed by stirring at room temperature for 1 h. The solids were removed by filtration through Celite and the filtrate extracted with diethyl ether (2×). The combined ether extracts were washed with water and brine, dried over magnesium sulfate, filtered and concentrated to provide the title compound as a brown oil (150 mg): $^1$H NMR (CDCl$_3$) δ 6.09 (s, 2H), 6.14 (s, 1H), 6.86-6.98 (m, 4H), 7.43 (d, 1H, J=9.6 Hz), 9.69 (d, 1H, J=4.5 Hz).

Example 2. 3(5)-[2-(2,3-methylenedioxyphenyl)vinyl]-1H-pyrazole

To a solution of diethoxyphosphorylacetaldehyde tosylhydrazone (8, 450 mg) in 6 mL of THF was added 92 mg of 60% NaH in portions, and the solution was stirred for 15 min. The solution was cooled to 0° C., and then a solution of the product from Example 1 in THF was added dropwise. The reaction was then stirred at room temperature for 1 h, then at reflux for 1 h. The reaction mixture was partitioned between 5% NaH$_2$PO$_4$ and ethyl acetate. The organic layer was separated, washed with water and brine, dried over magnesium sulfate, filtered and concentrated to provide the crude title product as a yellow oil. Purification via semi-preparative HPLC afforded a pure sample as a yellow solid: $^1$H NMR (CDCl$_3$) δ 6.11 (s, 2H), 6.69 (d, 1H, J=1.2 Hz), 6.91 (t, 1H, J=4.6 Hz), 7.02 (d, 1H, J=10 Hz), 7.22 (d, 1H, J=4.8 Hz), 7.30 (d, 1H, J=10 Hz), 7.64 (s, 1H), 7.64 (s, 1H).

Example 3.
3-(2-chloro-5-trifluoromethylphenyl)acrylaldehyde

To a solution of 2-chloro-5-trifluoromethylbenzaldehyde (300 mg) in 5 mL THF was added 40 mg of ZnBr$_2$. With stirring, 360 mg of α,α-bis(trimethylsilyl)-t-butylacetaldimine (7) was added, and stirring was continued overnight. The solution was cooled to 10° C., then hydrolyzed by the addition of a solution of ZnCl$_2$ (40 mg) in diethyl ether/water (3 mL each), followed by stirring at room temperature for 1 h. The solids were removed by filtration through Celite and the filtrate extracted with diethyl ether (2×). The combined ether extracts were washed with water and brine, dried over magnesium sulfate, filtered and concentrated to provide the title compound as a light brown oil (220 mg): $^1$H NMR (CDCl$_3$) δ 6.09 (s, 2H), 6.14 (s, 1H), 6.86-6.98 (m, 4H), 7.43 (d, 1H, J=9.6 Hz), 9.69 (d, 1H, J=4.5 Hz).

Example 4. 3(5)-[2-(2-chloro-5-trifluoromethylphenyl)vinyl]-1H-pyrazole

To a solution of diethoxyphosphorylacetaldehyde tosylhydrazone (8, 400 mg) in 5 mL of THF was added 92 mg of 60% NaH in portions, and the solution was stirred for 15 min. The solution was cooled to 0° C., and then a solution of the product from Example 3 in THF was added dropwise. The reaction was then stirred at room temperature for 1 h, then at reflux for 1 h. The reaction mixture was partitioned between 5% NaH$_2$PO$_4$ and ethyl acetate. The organic layer was separated, washed with water and brine, dried over magnesium sulfate, filtered and concentrated to provide the title product as a yellow solid: $^1$H NMR (CDCl$_3$) δ 6.61 (d, 1H, J=1.5 Hz), 7.20 (d, 1H, J=9.9 Hz), 7.44 (dd, 1H, J=5.1, 1.2 Hz), 7.47 (d, 1H, J=9.9 Hz), 7.51 (d, 1H, J=5.1 Hz), 7.60 (d, 1H, J=1.5 Hz), 7.91 (d, 1H, J=1.2 Hz).

Example 5. 3-(2-trifluoromethylphenyl)acrylaldehyde

To a solution of 2-trifluoromethylbenzaldehyde (260 mg) in 5 mL THF was added 200 mg of ZnBr$_2$. With stirring, 400 mg of α,α-bis(trimethylsilyl)-t-butylacetaldimine (7) was added, and stirring was continued overnight. The solution was cooled to 10° C., then hydrolyzed by the addition of a solution of ZnCl$_2$ (200 mg) in diethyl ether/water (3 mL each), followed by stirring at room temperature for 1 h. The solids were removed by filtration through Celite and the filtrate extracted with diethyl ether (2×). The combined ether extracts were washed with water and brine, dried over magnesium sulfate, filtered and concentrated to provide the crude title compound as an oil. The product was purified via silica gel column chromatography to afford a white powder (130 mg): $^1$H NMR (CDCl$_3$) δ 6.70 (dd, 1H, J=9.6, 4.5 Hz), 7.55 (t, 1H, J=4.5 Hz), 7.63 (t, 1H, J=4.5 Hz), 7.76 (d, 2H, J=4.8 Hz), 7.88 (br d, 1H, J=9.6 Hz), 9.77 (d, 1H, J=4.8 Hz).

Example 6. 3(5)-[2-(2-trifluoromethylphenyl)vinyl]-1H-pyrazole

To a solution of diethoxyphosphorylacetaldehyde tosylhydrazone (8, 250 mg) in 5 mL of THF was added 60 mg of 60% NaH in portions, and the solution was stirred for 15 min. The solution was cooled to 0° C., and then a solution of the product from Example 5 (150 mg) in THF was added dropwise. The reaction was then stirred at room temperature for 1 h, then at reflux for 1 h. The reaction mixture was partitioned between 5% NaH$_2$PO$_4$ and ethyl acetate. The organic layer was separated, washed with water and brine, dried over magnesium sulfate, filtered and concentrated to provide the title product as a white solid (76 mg): $^1$H NMR (CDCl$_3$) δ 6.58 (d, 1H, J=1.5 Hz), 7.12 (d, 1H, J=9.6 Hz), 7.37 (t, 1H, J=4.5 Hz), 7.45 (dd, 1H, J=9.6, 1.2 Hz), 7.54 (t, 1H, J=4.5 Hz), 7.59 (d, 1H, J=1.5 Hz), 7.67 (d, 1H, J=4.8 Hz), 7.78 (d, 1H, J=4.8 Hz).

Example 7. 3(5)-[2-(2-thienyl)vinyl]-1H-pyrazole

To a solution of diethoxyphosphorylacetaldehyde tosylhydrazone (4, 75 g) in 400 mL of THF was added 11.6 g of 60% NaH in portions, and the solution was stirred for 15 min. The solution was cooled to 0° C., and then a solution of 3-(2-thienyl)acrylaldehyde (prepared from 2-thienaldehyde and acetaldehyde as described in Heskin, H., Miller, R. E.; Nord, F. F. *J. Org. Chem.* 1951, 16, 199) in 100 mL THF was added dropwise. The reaction was then stirred at room temperature for 1 h, then at reflux for 1 h. The reaction mixture was partitioned between 5% NaH$_2$PO$_4$ and ethyl acetate. The organic layer was separated, washed with water and brine, dried over magnesium sulfate, filtered and concentrated to provide the crude title product as a brown oil. Purification via silica gel column chromatography afforded 8.3 g of a yellow powder. Trituration with dichloromethane/hexane afforded 4.4 g of yellow powder having >98% purity: $^1$H NMR (CDCl$_3$) δ 6.47 (d, 1H, J=1.5 Hz), 6.93 (d, 1H, J=9.9 Hz), 6.99 (dd, 1H, J=3.9, 2.1 Hz), 7.06 (d, 1H, J=2.1 Hz), 7.20 (d, 1H, J=3.9 Hz), 7.22 (d, 1H, J=9.9 Hz), 7.57 (d, 1H, J=1.5 Hz).

Figure 1

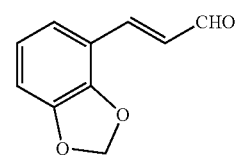

Example 1

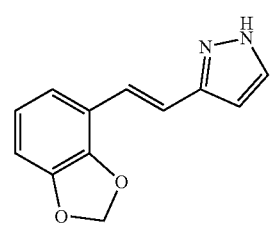

Example 2

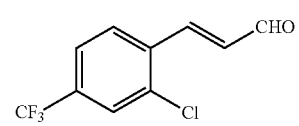

Example 3

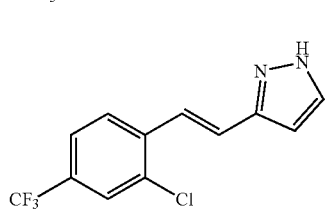

Example 4

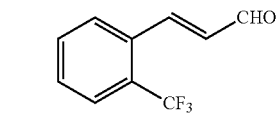

Example 5

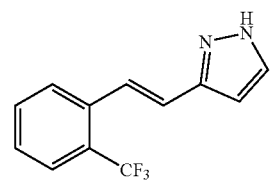

Example 6

Scheme 3 shows some exemplary reactants and the corresponding intermediate and product. Following flash column chromatography, the desired intermediates were obtained in 60-95% yields. Conversion to the final analogues using reagent 8 gave compounds falling within the scope of compounds of Formula II.

Scheme 3

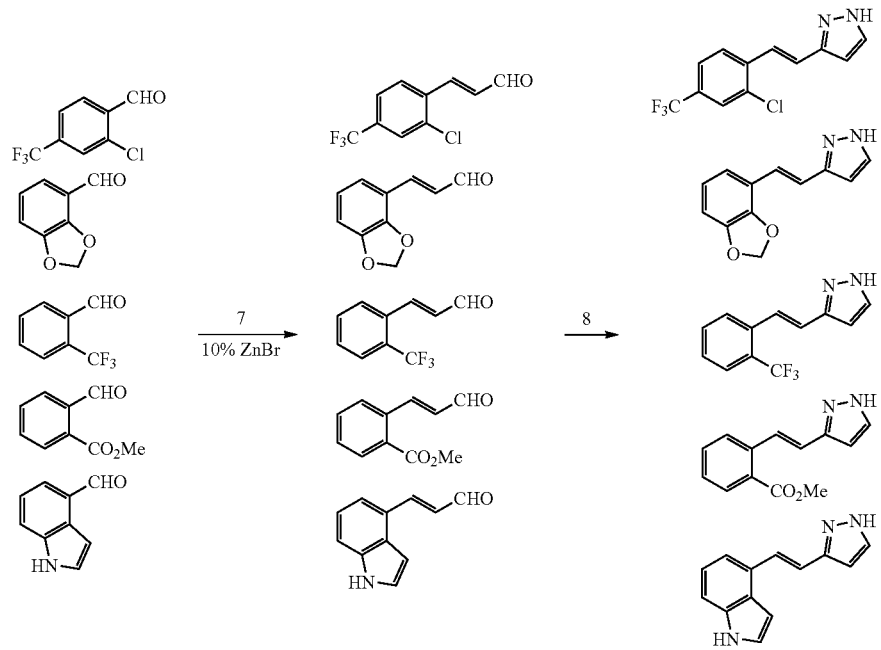

Using the aforementioned methods, the compounds described below, among others, were prepared.

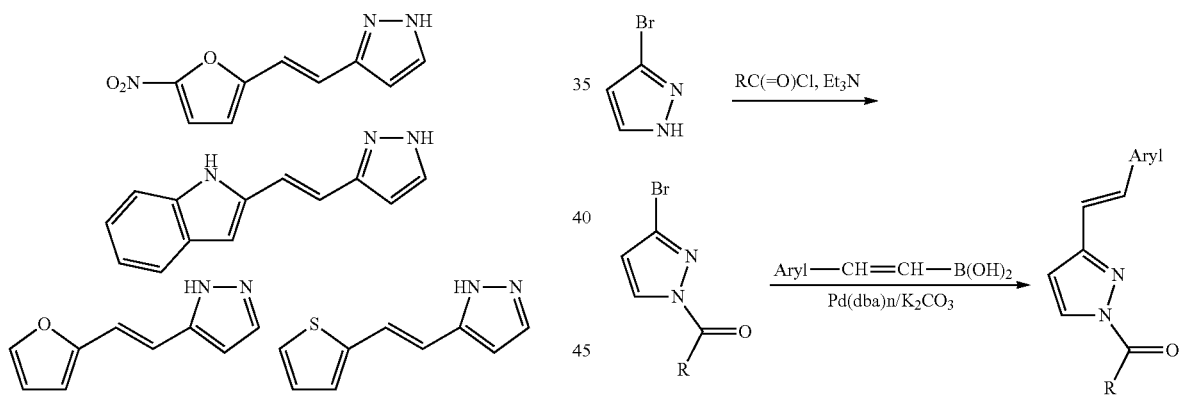

1,3- and 1,5-Disubstituted Pyrazoles (C(3) and C(5)-Positional Isomers)

In certain other embodiments, compounds of general Formula III of the invention may be synthesized by any of several methods. In certain embodiments, in Method A, illustrated below, 3-bromopyrazole (commercially available) will undergo alkylation or acylation by reaction with an acyl chloride or alkyl halide in a suitable polar aprotic solvent such as dichloromethane and base such triethylamine to form the intermediate compound. Coupling reaction with a boronic acid, using a palladium catalyst, base such as $K_2CO_3$ or $CsCO_3$, and warming in an aprotic solvent such as benzene, toluene, or xylene will provide the target pyrazoles. Alternatively, 3-bromopyrazole may be coupled with vinyl compounds in the presence of a catalyst prepared in situ from 2.5% $Pd(AcO)_2$ with 5% mono-sulfonated triphenylphosphine (TPPTS) in an aqueous solvent such as water and ethanol. (Ref. Genet, J. P., Blart, E.; Savignac, M., Synlett, 1992, 715-717).

As discussed above, 1H-pyrazole-type compounds such as 3-Bromo-1H-pyrazole, typically exist as a mixture of tautomers. Therefore, acylation of 3-Bromo-1H-pyrazole with $RC(=O)Cl$ leads to a mixture of C(3)- and C(5)-positional isomers, as depicted below:

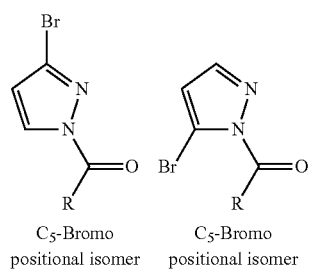

C₅-Bromo positional isomer     C₅-Bromo positional isomer

Therefore, method A allows the preparation of both C(3)- and C(5)-positional isomers of compounds of the invention, e.g.:

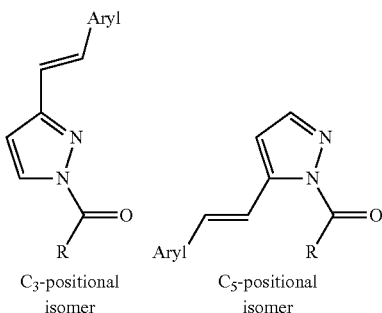

C3-positional isomer    C5-positional isomer

For example, using Method A, above, for the preparation of a related compound (4-chlorophenyl)[3-(2-(2-thienyl)vinyl)-1H-pyrazol-1-yl]methanone described in U.S. Pat. No. 6,610,726, incorporated herein by reference in its entirety, one may react 3-bromopyrazole with 4-chlorobenzoyl chloride (commercially available, for example, from Aldrich Chemical Co., Milwaukee, Wis.) to provide the first intermediate in Method A. Then reaction of this material with epsilon-2-(thienylethenyl)boronic acid (commercially available, for example, from Combi-Blocks Inc., San Diego, Calif.) forms the desired product. Compounds corresponding to those described in Formulae III$^{D1}$, III$^{D2}$ and III$^{D3}$ herein may be likewise prepared from the corresponding benzoyl chlorides as well as many different types of boronic acid analogs that are commercially available or readily synthesized.

For example, the following procedures were used to prepare 1,3- (and 1,5-) disubstituted pyrazole compounds of general Formula (III).

Example 8. 3(5)-[2-(phenyl)vinyl]-1-(4-chlorobenzoyl)-1H-pyrazole

To a solution of the product from Example 7 (3.2 g) in 60 mL dichloromethane was added 5.7 g Na$_2$CO$_3$ powder, and the solution was then cooled to 0° C. 4-Chlorobenzoyl chloride (3.2 g) was added dropwise, the ice bath was removed, and the reaction was allowed to stir at room temperature overnight. The solids were removed by filtration, the filter pad was rinsed with dichloromethane, and the combined filtrates were concentration to a small volume. Hexane was added to the concentrated solution, resulting in precipitation of the desired product as a yellow powder, which was collected via vacuum filtration, rinsed with hexane, and air dried (4.7 g): $^1$H NMR (CDCl$_3$) δ 6.72 (d, 1H, J=1.8 Hz), 6.97 (d, 1H, J=9.9 Hz), 7.03 (dd, 1H, J=3.0, 2.1 Hz), 7.14 (d, 1H, J=2.1 Hz), 7.27 (d, 1H, J=2.1 Hz), 7.33 (d, 1H, J=9.9 Hz), 7.49-7.52 (m, 3H), 8.08 (dt, 1H, J=5.4, 1.5 Hz), 8.17 (dt, 2H, J=5.4, 1.5 Hz), 8.39 (dd, 1H, J=1.5, 0.6 Hz).

In Method B, depicted below, cinnamaldehydes undergo reaction with hydrazides to form hydrazone intermediates. The dianion of the corresponding hydrazones undergo reaction with esters, amides, acid anhydrides, acid chlorides and alkyl carbonates to form target pyrazoles. (ref. Tetrahedron Lett. 1983, 24(31), 3239-3242).

Method B

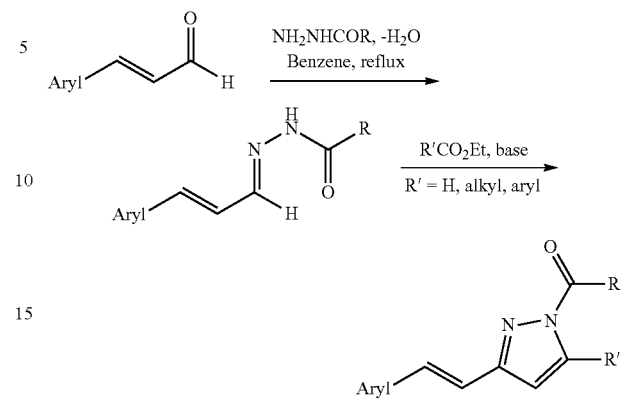

Using the aforementioned methods, the compounds described below, among others, were prepared.

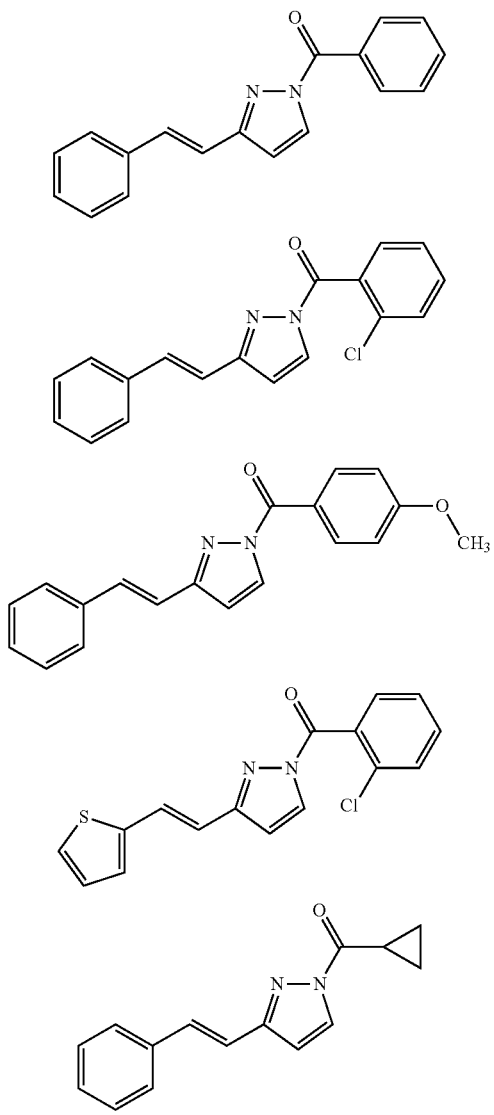

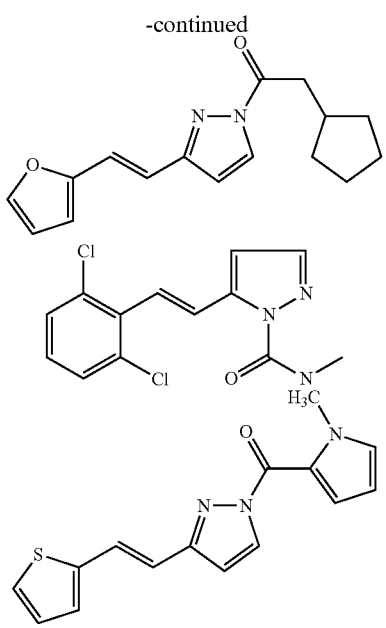

The foregoing are merely exemplary of synthetic routes to the compound of the invention. The foregoing compounds, compositions and methods of the invention are illustrated by the following examples, which are merely exemplary of aspects of the invention and are not limiting.

2) Biological Activity:

1. Assessment of HGF/SF-Like Activity:

The following assay was performed to assess the HGF/SF-like activity of the compounds of the invention. Endothelial cells (HUVECs) were seeded in 48 well plates at a density of 10,000 to 20,000 cells per well in the normal growth medium (EGM-2-Clonetics) containing 2% fetal bovine serum, FGF, VEGF, IGF, ascorbic acid, EGF, GA, heparin and hydrocortisone. The cells were grown normally in the growth medium for 24 hr at 37° C. and 5% $CO_2$. The cells were then rinsed with RPMI-1% BSA and starved for 1-2 hrs. The stock solutions of the compounds of the invention were made at a concentration of 10 mg/ml in DMSO and diluted in RPMI-1% BSA at a final concentrations of 0.01 micromolar to 25 micromolar. The cells were then washed and treated with the compounds and incubated for another 24 hr at 37° C. Then $^3$H thymidine (0.5 microgram/ml in RPMI-BSA) was added to the cells and incubated at 37° C. for 4 to 5 hours. The unincorporated thymidine was removed by washing the cells four times with 1×PBS. Then the cells were lysed with 0.5M NaOH for 30 min and the radioactivity counted in the beta counter. A similar proliferation assay using monkey bronchial epithelial cells (4MBR-5) was also employed.

The following compounds demonstrated activity in the aforementioned assay.

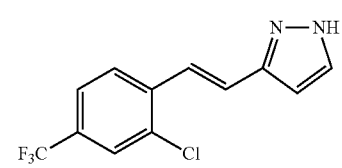

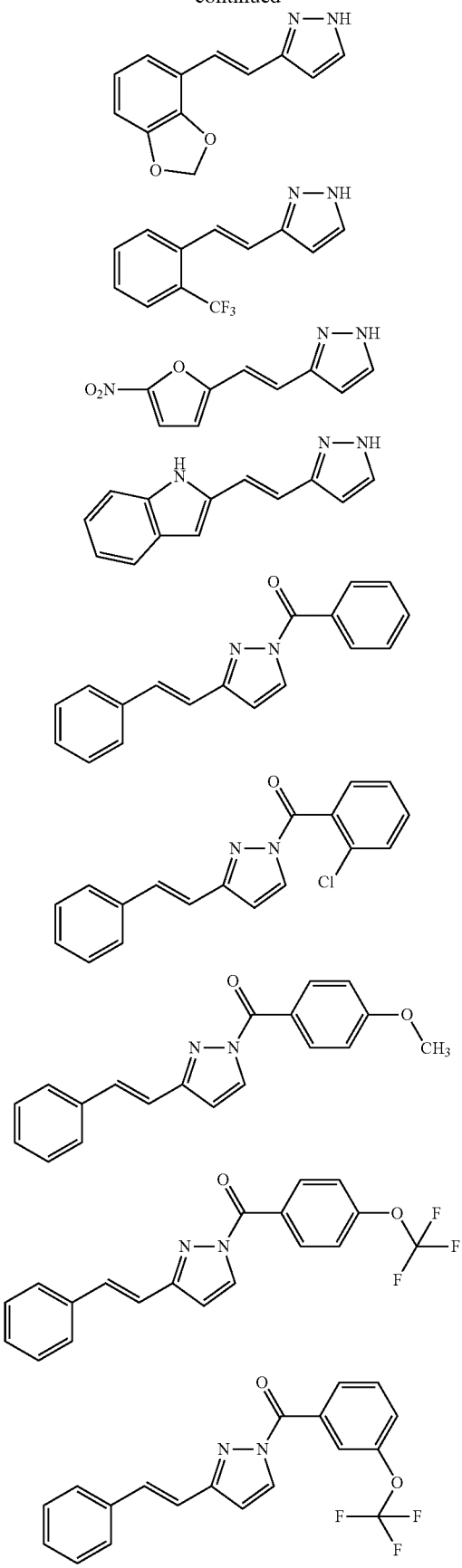

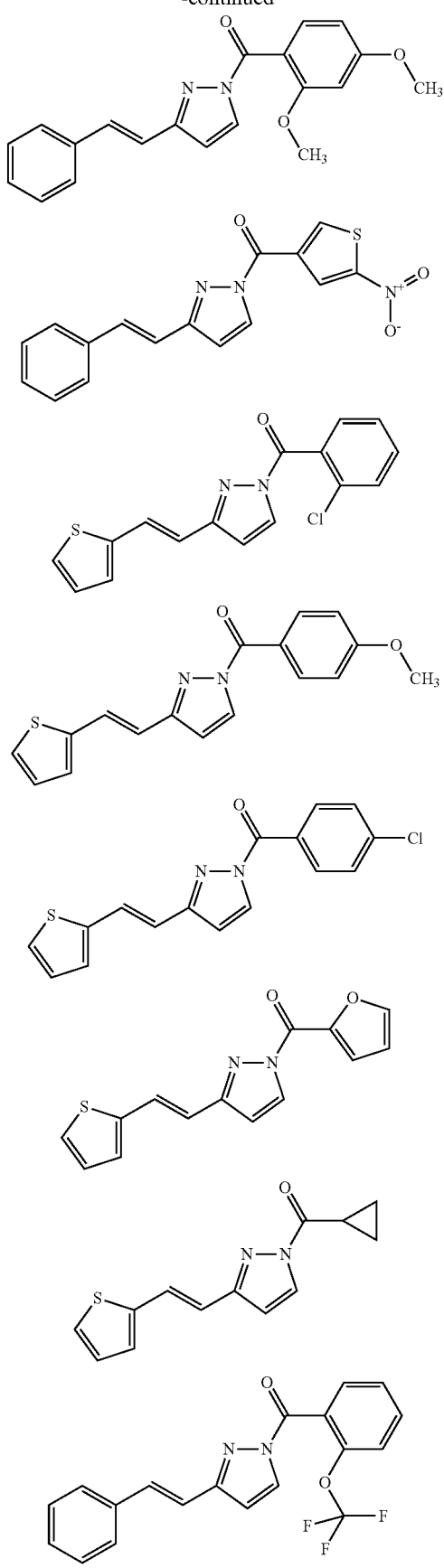
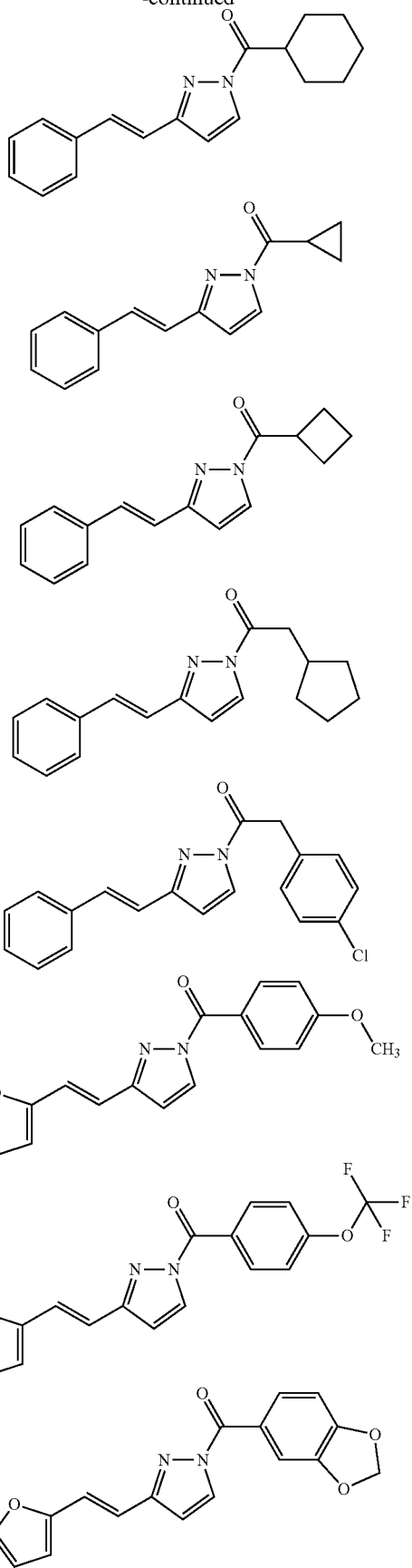

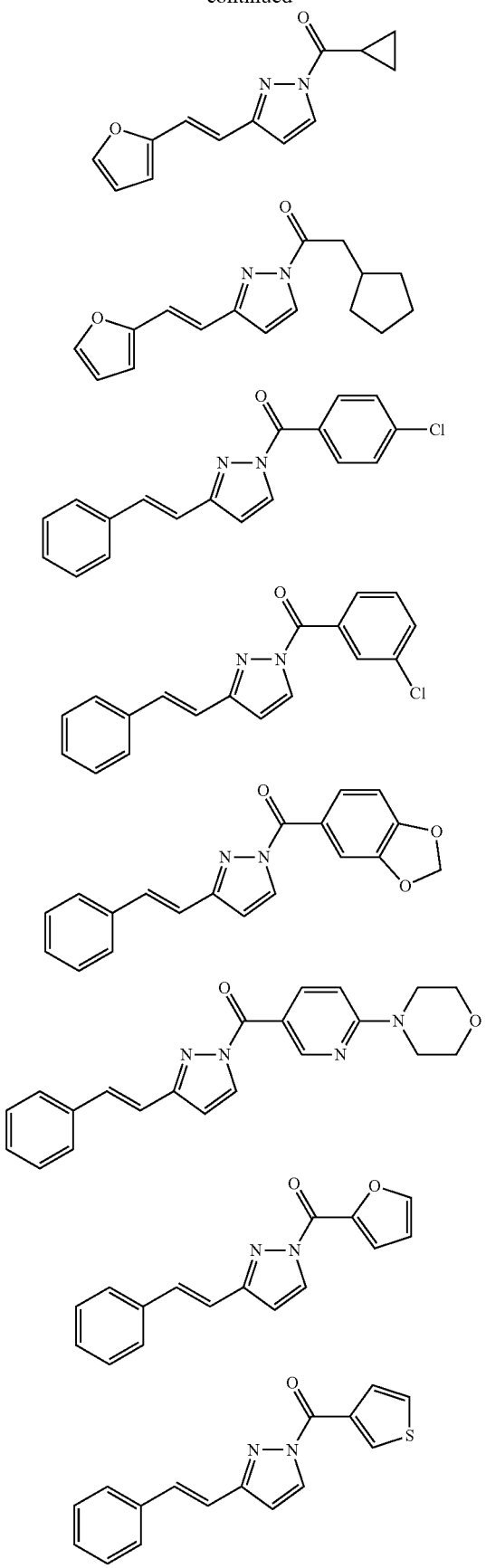
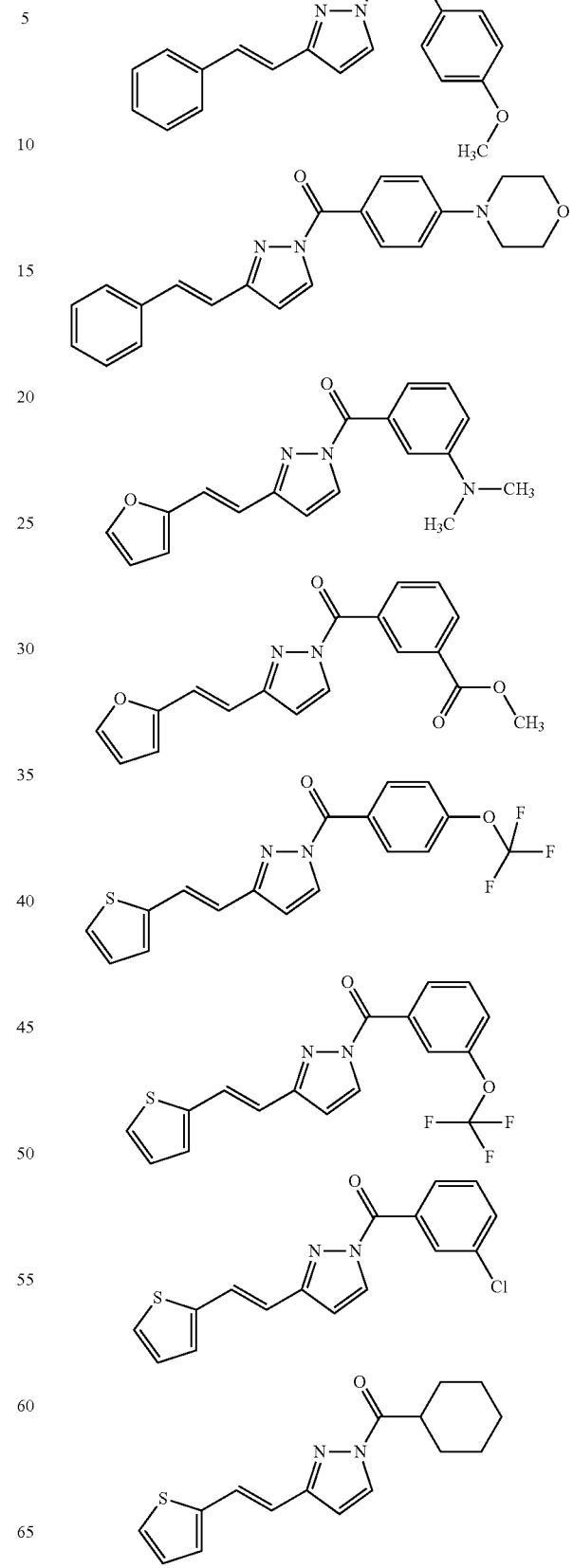

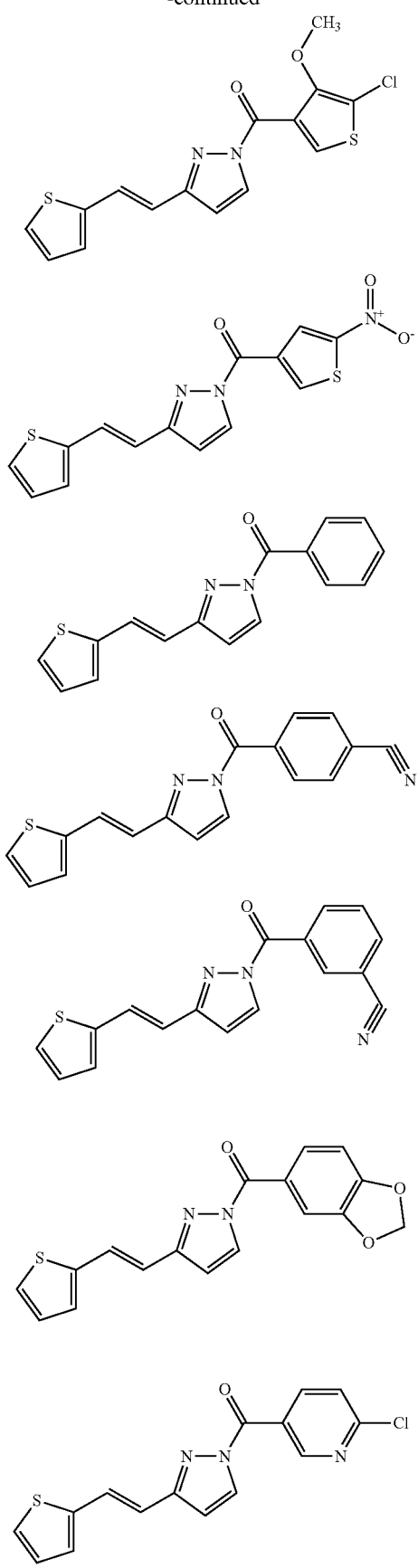
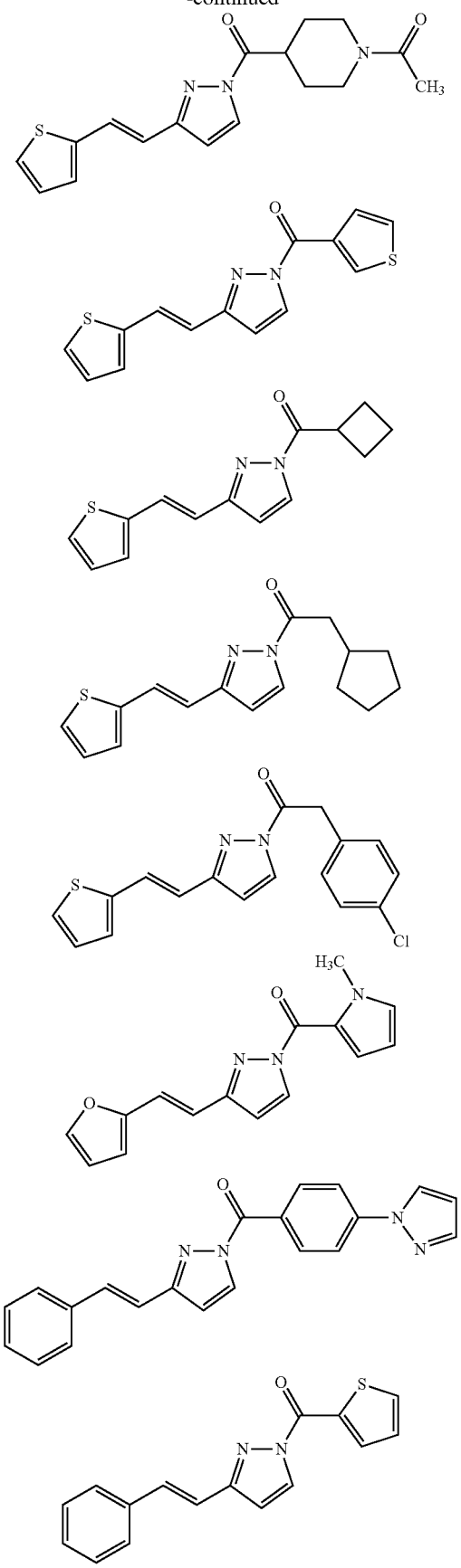

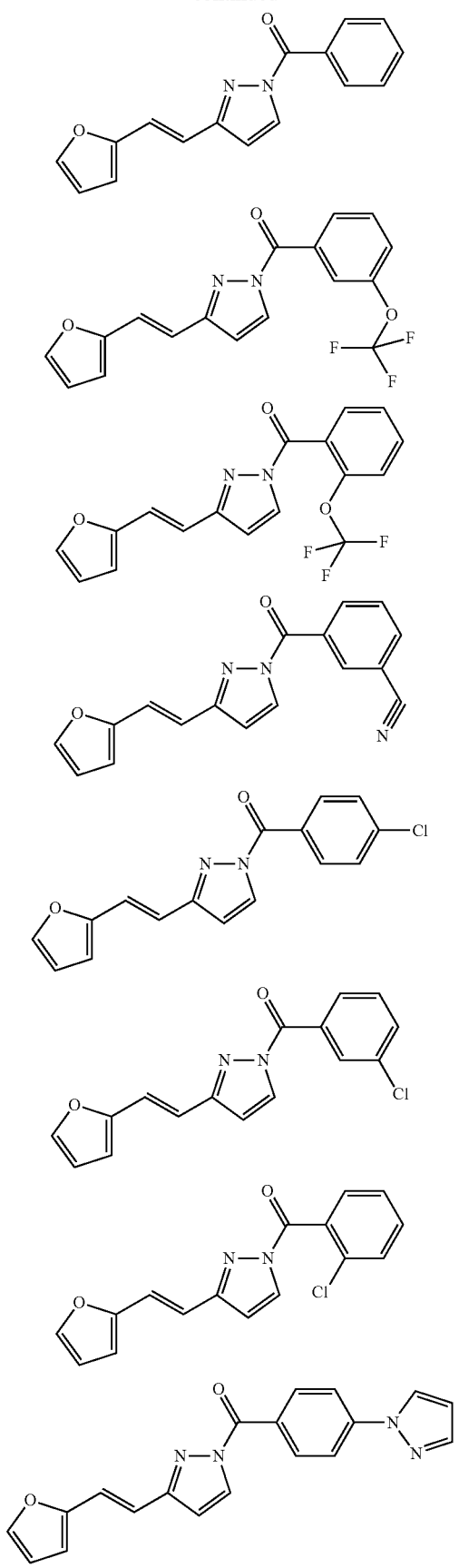
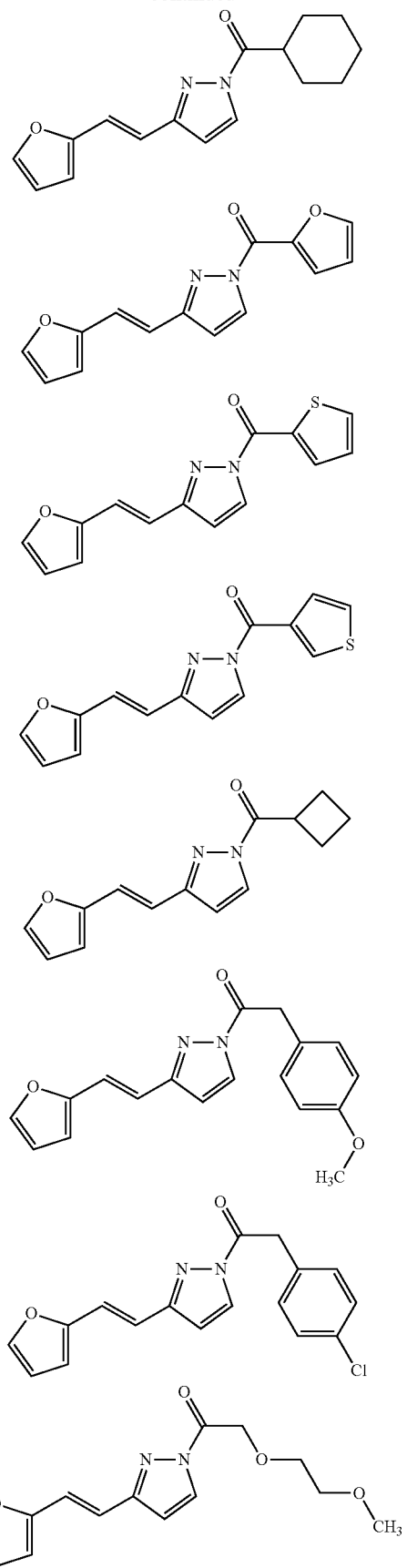

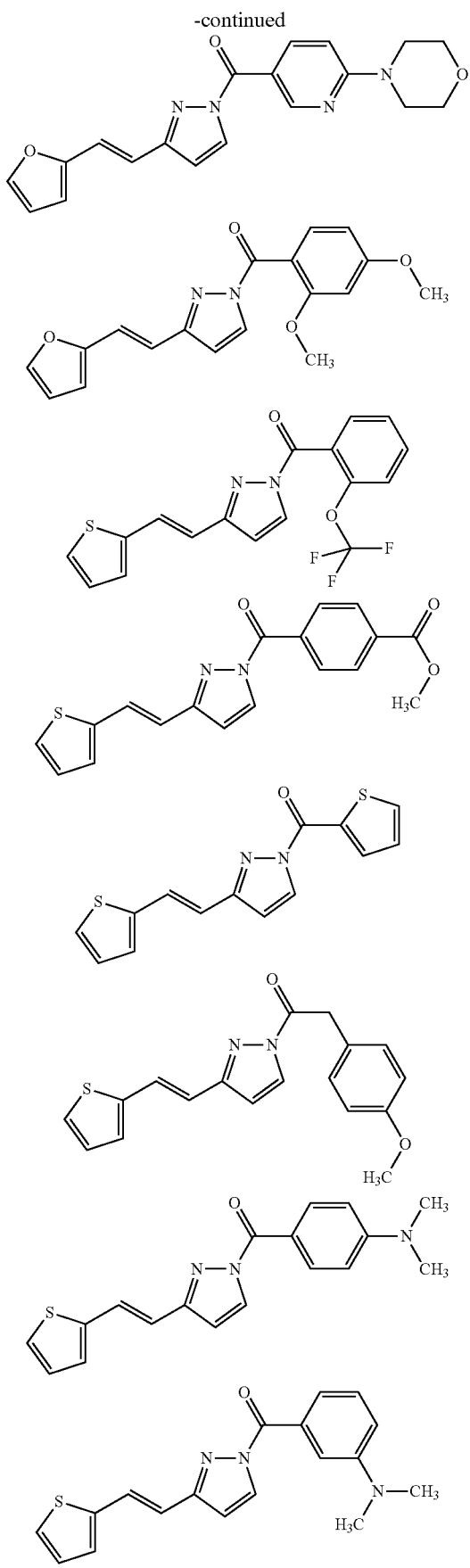

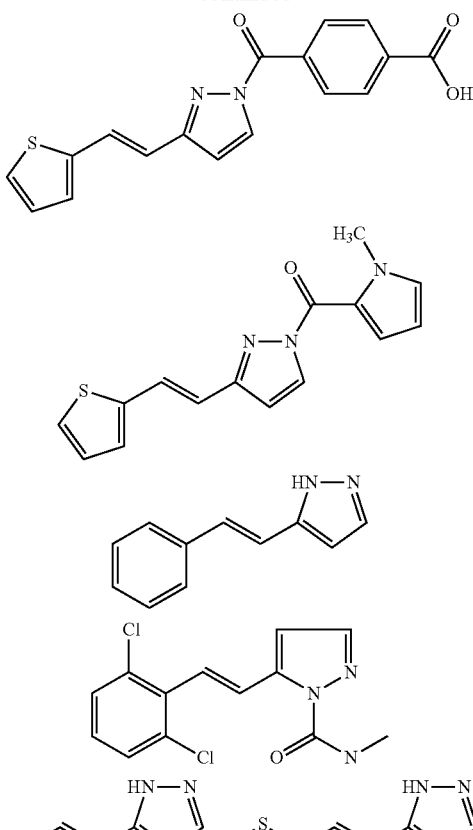

Effectiveness of the aforementioned compounds in various conditions and diseases is described in U.S. Pat. Nos. 7,192,976; 7,250,437; and 7,265,112, all of which are incorporated herein by reference.

2. Expanded Therapeutic Window—Acute Myocardial Infarction.

In the left anterior descending artery (LAD) ligation model of acute myocardial infarction in the normothermic rat, a compound of the invention was found to reduce infarct size and the number of apoptotic cells measured 48 hours after LAD ligation, when compound is administered at the time of infarct or as much as three hours after ligation. In the 3 hour delayed treatment study, infarct size of untreated vs. compound treated rats (single IV dose, 2 mg/kg) was 60% vs. 25%, respectively, and % apoptotic cells 80% vs. 25%, respectively. In another experiment, a delay of 24 hours before starting treatment also reduced infarct size.

3. Expanded Therapeutic Window—Post-Infarct Ventricular Remodeling and Heart Failure.

Animals surviving the LAD ligation model undergo cardiac remodeling during the post-infarct period, and show an increase in ED chamber volume, and a decrease in fractional shortening and ejection fraction. When compound of the invention is administered starting 48 hours after LAD ligation and continuing daily for 9 weeks (2 mg/kg, IP), benefits to the three cardiac function parameters is noted, according to the following table.

|  | Vehicle | Treated | No LAD ligation |
|---|---|---|---|
| ED chamber volume (cm³) | 0.8 | 0.55 | 0.45 |
| Fractional shortening (%) | 15 | 25 | 35 |
| Ejection fraction (%) | 30 | 45 | 65 |

4. Delayed Treatment in Renal Ischemia.

The effect of delayed treatment with a compound of the invention in a normothermic renal ischemia model was investigated. Male Sprague-Dawley rats were subjected to 60 minutes of renal ischemia, then randomized into a vehicle group (n=11) and a treatment group (n=14). Administration of 2 mg/kg compound, IV, was started 24 hours after reperfusion and then again at 48, 72 and 96 hours after reperfusion. Mortality and renal function were assessed every 24 hours. At 96 hours, survival in the treated group was 50%, vs. 11% in the vehicle group. Serum creatinine and BUN at 48 hours post reperfusion and beyond were significantly decreased in the treatment group compared to vehicle.

5. Model of Amyotrophic Lateral Sclerosis (ALS).

The SOD$^{G93A}$ mouse model of ALS was used to evaluate the effect of a compound of the invention on progressive pathology of ALS. Eight-week old mice were administered compound at a dose of 2 mg/kg, IP (n=10) daily starting at age 94 days, when neurofilament degeneration typically occurs, through day 122. Using a hindlimb clinical observation score described in Gurney et al., 1994, Science 264:1772-5, compound treatment significantly improved the pathology score vs. the vehicle-treated cohort (n=10), p=0.016. In addition, a stride test showed that treated animals showed improvement. Survival of the treated animals was also significantly (p<0.05) extended vs. vehicle-treated animals.

6. Oral Administration in Chronic Kidney Disease (CKD).

The effects of delayed, orally administered compound were examined in a standard and well-characterized mammalian model of CKD. Adult male Sprague-Dawley rats were subjected to ⅚ nephrectomy via ligation of 2 of the 3 branches of the left renal artery and excision of the right kidney. Three days after ablation, blood samples were obtained and serum creatinine (SCr) determined. Rats with SCr values between 0.8 and 1.2 mg/dL (baseline SCr for rats is 0.2 mg/dL), indicating adequate and sustained renal ablation, were entered into the study. One week following surgery, animals were randomized to vehicle (n=15) or compound (45 mg/kg, PO, QD, n=15). Six weeks following surgery (i.e. 5 weeks into treatment) animals were sacrificed. Urine and kidney samples were obtained for evaluation of proteinuria, histopathology and pharmacodynamic markers of compound action. Oral administration of compound was found to be therapeutic in CKD, attenuating mortality, reducing proteinuria and kidney collagen content (hydroxyproline and Sirius red staining). In another study, daily oral treatment of 15 or 45 mg/kg (n=15; vehicle n=15) was started 2 weeks after surgery and continued for 10 weeks. At 10 weeks, evaluation showed similar survival in both treatment groups (80%) vs. untreated animals (45%), and a dose-responsive reduction in kidney collagen content.

7. Oral Administration Attenuated Proteinuria in Metabolic Syndrome.

Three-month old obese male ZSF1 rats were randomized to vehicle or compound (45 mg/kg, oral, daily, n=5/group). Prior to randomization these rats exhibited severe spontaneous hyperglycemia (~450 mg/dL) and hypercholesterolemia (ca. 1500 mg/dL). After 10 days of treatment, 24-hour proteinuria was significantly reduced.

8. Delayed Treatment in Liver Fibrosis.

Adult male SD rats were administered thioacetamide (TAA, 200 mg/kg, ip), thrice/week for 4-8 weeks until the appearance of hepatic fibrosis. Treatment with inventive compound (ip, PO) concomitant with or subsequent to TAA administration attenuates progression of hepatic fibrosis-reducing liver profibrotic genes and liver collagen content. The following protocols were studied all of which were found to be benefited from treatment: 1) liver fibrosis induced with TAA during weeks 1-8, IV compound treatment during weeks 9-12, 2) liver fibrosis induced with TAA during weeks 1-6, IV compound treatment weeks 4-8, 3) liver fibrosis induced with TAA during weeks 1-8, oral compound treatment weeks 9-12, and 4) liver fibrosis induced with TAA during weeks 1-4, oral compound treatment weeks 5-9.

9. Muscular Dystrophy.

In a genetic murine muscular dystrophy model, administration of a compound embodied herein for 2 months, daily via intraperitoneal injection reduced levels of creatine kinase, a hallmark of the disease.

10. Parenteral Formulations of Compounds of the Invention.

A parenteral formulation providing increased solubility of a compound of the invention for, e.g., intravenous or intraperitoneal administration, was prepared using 10% polysorbate 80 (v/v), 50% polyethylene glycol 300 (v/v) and 40% (v/v) phosphate-buffered saline. This formulation provided increased solubility such that doses can be delivered in a manageable volume. The solubility of compound increases from about 0.02-1 mg/mL in water to about 0.8 to 10 mg/mL in this formulation.

In one embodiment, a formulation is provided comprising 0.5% (w/v) 3(5)-[2-(2,3-methylenedioxyphenyl)vinyl]-1H-pyrazole in 10% polysorbate 80 (v/v), 50% polyethylene glycol 300 (v/v) and 40% (v/v) phosphate-buffered saline.

In another embodiment, a formulation is provided comprising 0.5% (w/v) 3(5)-[2-(2-chloro-5-trifluoromethylphenyl)vinyl]-1H-pyrazole in 10% polysorbate 80 (v/v), 50% polyethylene glycol 300 (v/v) and 40% (v/v) phosphate-buffered saline.

In one embodiment, a formulation is provided comprising 0.5% (w/v) 3(5)-[2-(2-trifluoromethylphenyl)vinyl]-1H-pyrazole in 10% polysorbate 80 (v/v), 50% polyethylene glycol 300 (v/v) and 40% (v/v) phosphate-buffered saline.

In one embodiment, a formulation is provided comprising 0.5% (w/v) 3(5)-[2-(2-furyl)vinyl]-1H-pyrazole in 10% polysorbate 80 (v/v), 50% polyethylene glycol 300 (v/v) and 40% (v/v) phosphate-buffered saline.

In one embodiment, a formulation is provided comprising 0.5% (w/v) 3(5)-[2-(2-thienyl)vinyl]-1H-pyrazole in 10% polysorbate 80 (v/v), 50% polyethylene glycol 300 (v/v) and 40% (v/v) phosphate-buffered saline.

In one embodiment, a formulation is provided comprising 0.5% (w/v) 3(5)-[2-(phenyl)vinyl]-1-(4-chlorobenzoyl)-1H-pyrazole in 10% polysorbate 80 (v/v), 50% polyethylene glycol 300 (v/v) and 40% (v/v) phosphate-buffered saline.

Other compounds in the same or similar formulations can include (E)-3(5)-[2-(2,3-methylenedioxyphenyl)vinyl]-1H-pyrazole, (Z)-3(5)-[2-(2,3-methylenedioxyphenyl)vinyl]-1H-pyrazole, (E)-3(5)-[2-(2-chloro-5-trifluoromethylphenyl)vinyl]-1H-pyrazole, (Z)-3(5)-[2-(2-chloro-5-trifluoromethylphenyl)vinyl]-1H-pyrazole, (E)-3(5)-[2-(2- trifluoromethylphenyl)vinyl]-1H-pyrazole, (Z)-3(5)-[2-(2-trifluoromethylphenyl)vinyl]-1H-pyrazole, (E)-3(5)-[2-(2-furyl)vinyl]-1H-pyrazole, (Z)-3(5)-[2-(2-furyl)vinyl]-1H-pyrazole, (E)-3 (5)-[2-(2-thienyl)vinyl]-1H-pyrazole, (Z)-3 (5)-[2-(2-thienyl)vinyl]-1H-pyrazole, (E)-3-(2-(5-nitrofuran-2-yl)vinyl)-1H-pyrazole, (Z)-3-(2-(5-nitrofuran-2-yl)vinyl)-1H-pyrazole, (E)-3-styryl-1H-pyrazole, (Z)-3-styryl-1H-pyrazole, (E)-2-(2-(1H-pyrazol-3-yl)vinyl)-1H-indole, (Z)-2-(2-(1H-pyrazol-3-yl)vinyl)-1H-indole, (E)-4-(2-(1H-pyrazol-3-yl)vinyl)-N,N-dimethylaniline, (Z)-4-(2-(1H-pyrazol-3-yl)vinyl)-N,N-dimethylaniline, (E)-3-(4-methoxystyryl)-1H-pyrazole, (Z)-3-(4-methoxystyryl)-1H-pyrazole, (E)-3-(2,6-dichiorostyryl)-1H-pyrazole, (Z)-3-(2,6-dichlorostyryl)-1H-pyrazole, (E)-3-(2-(naphthalen-2-yl)vinyl)-1H-pyrazole, (Z)-3-(2-(naphthalen-2-yl)vinyl)-1H-pyrazole, (E)-3-(2-(1H-pyrrol-2-yl)vinyl)-1H-pyrazole, (Z)-3-(2-(1H-pyrrol-2-yl)vinyl)-1H-pyrazole, (E)-3-(2-(thiophen-3-yl)vinyl)-1H-pyrazole, (Z)-3-(2-(thiophen-3-yl)vinyl)-1H-pyrazole, (E)-3-(2-(1H-pyrrol-3-yl)vinyl)-1H-pyrazole, (Z)-3-(2-(1H-pyrrol-3-yl)vinyl)-1H-pyrazole, (E)-3-(2-(furan-3-yl)vinyl)-1H-pyrazole, (Z)-3-(2-(furan-3-yl)vinyl)-1H-pyrazole, 3(5)-[2-(phenyl)vinyl]-1-(4-chlorobenzoyl)-1H-pyrazole, (E)-furan-2-yl(3-styryl-1H-pyrazol-1-yl)methanone, (E)-(3-(2,6-dichiorostyryl)-1H-pyrazol-1-yl)(thiophen-2-yl)methanone, (E)-2-(4-methoxyphenyl)-1-(3-styryl-1H-pyrazol-1-yl)ethanone, (E)-cyclopropyl(3-styryl-1H-pyrazol-1-yl)methanone, (E)-(6-morpholinopyridin-3-yl)(3-styryl-1H-pyrazol-1-yl)methanone, (E)-(3-(2-(furan-2-yl)vinyl)-1H-pyrazol-1-yl)(4-(trifluoromethoxy)phenyl)methanone, (E)-(3-(2-(furan-2-yl)vinyl)-1H-pyrazol-1-yl)(3-(trifluoromethoxy)phenyl)methanone, (E)-(3-(2-(furan-2-yl)vinyl)-1H-pyrazol-1-yl)(2-(trifluoromethoxy)phenyl)methanone, (E)-(3-(2-(furan-2-yl)vinyl)-1H-pyrazol-1-yl)(phenyl)methanone, (E)-benzo[d][1,3]dioxol-5-yl(3-(2-(furan-2-yl)vinyl)-1H-pyrazol-1-yl)methanone, (E)-(3-(2-(thiophen-2-yl)vinyl)-1H-pyrazol-1-yl)(4-(trifluoromethoxy)phenyl)methanone, (E)-3-(3-(2-(furan-2-yl)vinyl)-1H-pyrazole-1-carbonyl)benzonitrile, (E)-methyl 4-(3-(2-(thiophen-2-yl)vinyl)-1H-pyrazole-1-carbonyl)benzoate, (E)-(3-(2-(thiophen-2-yl)vinyl)-1H-pyrazol-1-yl)(3-(trifluoromethoxy)phenyl)methanone, (E)-phenyl(3-(2-(thiophen-2-yl)vinyl)-1H-pyrazol-1-yl)methanone, (E)-benzo[d][1,3]dioxol-5-yl(3-(2-(thiophen-2-yl)vinyl)-1H-pyrazol-1-yl)methanone, (E)-3-(3-(2-(thiophen-2-yl)vinyl)-1H-pyrazole-1-carbonyl)benzonitrile, (E)-4-(3-(2-(thiophen-2-yl)vinyl)-1H-pyrazole-1-carbonyl)benzonitrile, (E)-4-(3-(2-(thiophen-2-yl)vinyl)-1H-pyrazole-1-carbonyl)benzoic acid, (E)-cyclohexyl(3-(2-(thiophen-2-yl)vinyl)-1H-pyrazol-1-yl)methanone, (E)-1-(4-(3-(2-(thiophen-2-yl)vinyl)-1H-pyrazole-1-carbonyl)piperidin-1-yl)ethanone, (E)-(3-(2-(fu ran-2-yl)vinyl)-1H-pyrazol-1-yl)(1-methyl-1H-pyrrol-2-yl)methanone, (E)-2-cyclopentyl-1-(3-(2-(thiophen-2-yl)vinyl)-1H-pyrazol-1-yl)ethanone, (E)-2-(4-chlorophenyl)-1-(3-(2-(thiophen-2-yl)vinyl)-1H-pyrazol-1-yl)ethanone, (E)-(6-chloropyridin-3-yl)(3-(2-(thiophen-2-yl)vinyl)-1H-pyrazol-1-yl)methanone, (E)-3-(3-(2-(1H-pyrrol-2-yl)vinyl)-1H-pyrazol-1-yl)benzonitrile, (E)-3-(3-(2-(furan-3-yl)vinyl)-1H-pyrazole-1-carbonyl)benzonitrile, (E)-3-(3-(2-(1H-pyrrol-3-yl)vinyl)-1H-pyrazole-1-carbonyl)benzonitrile, or (E)-3-(3-(2-(thiophen-3-yl)vinyl)-1H-pyrazole-1-carbonyl)benzonitrile.

11. Solid Dosage Forms of the Invention.

New solid dosage forms of the compounds of the invention are provided. In one embodiment, a formulation is prepared in a solid formulation comprising about 20% (w/w) compound of the invention, about 10-20% (w/w) GELUCIRE® 44/14, about 10-20% (w/w) vitamin E TPS, 0 to about 60% polyethylene glycol 400, 0 to about 40% Lubasol, 0 to about 15% Cremophor RH 40 (w/w), and about 1% (w/w) BHT. Formulations containing Cremophor RH 20 were liquid at room temperature but waxy solids at 4 C. The foregoing examples of one or more agents to aid in preparing formulations of inventive compound are merely illustrative and non-limiting. Any of the foregoing branded excipients can be substituted with the equivalent generic component. For example, Cremophor RH 20 can be replaced with ethoxylated castor oil; GELUCIRE 44/14 with lauroyl macrogol glyceride.

Other formulations are shown in the Table below.

| Ingredients | Formulation A | Formulation B | Formulation C | Formulation D | Formulation E |
| --- | --- | --- | --- | --- | --- |
| Compound | 100 | 100 | 100 | 100 | 100 |
| Gelucire 44/14 | 100 | 100 | 50 | 120 | 50 |
| Vitamin E TPS | 100 | 50 | 50 | 0 | 50 |
| PEG 400 | 195 | 0 | 295 | 195 | 300 |
| Lubrizol | 0 | 195 | 0 | 0 | 0 |
| Cremophor RH 40 | 0 | 50 | 0 | 75 | 0 |
| BHT | 5 | 5 | 10 | 10 | 0 |

In certain embodiments, the compound is one of the following: (E)-3(5)-[2-(2,3-methylenedioxyphenyl)vinyl]-1H-pyrazole, (Z)-3(5)-[2-(2,3-methylenedioxyphenyl)vinyl]-1H-pyrazole, (E)-3(5)-[2-(2-chloro-5-trifluoromethylphenyl)vinyl]-1H-pyrazole, (Z)-3(5)-[2-(2-chloro-5-trifluoromethylphenyl)vinyl]-1H-pyrazole, (E)-3 (5)-[2-(2-trifluoromethylphenyl)vinyl]-1H-pyrazole, (Z)-3 (5)-[2-(2-trifluoromethylphenyl)vinyl]-1H-pyrazole, (E)-3 (5)-[2-(2-furyl)vinyl]-1H-pyrazole, (Z)-3(5)-[2-(2-furyl)vinyl]-1H-pyrazole, (E)-3(5)-[2-(2-thienyl)vinyl]-1H-pyrazole, (Z)-3(5)-[2-(2-thienyl)vinyl]-1H-pyrazole, (E)-3-(2-(5-nitrofuran-2-yl)vinyl)-1H-pyrazole, (Z)-3-(2-(5-nitrofuran-2-yl)vinyl)-1H-pyrazole, (E)-3-styryl-1H-pyrazole, (Z)-3-styryl-1H-pyrazole, (E)-2-(2-(1H-pyrazol-3-yl)vinyl)-1H-indole, (Z)-2-(2-(1H-pyrazol-3-yl)vinyl)-1H-indole, (E)-4-(2-(1H-pyrazol-3-yl)vinyl)-N,N-dimethylaniline, (Z)-4-(2-(1H-pyrazol-3-yl)vinyl)-N,N-dimethylaniline, (E)-3-(4-methoxystyryl)-1H-pyrazole, (Z)-3-(4-methoxystyryl)-1H-pyrazole, (E)-3-(2,6-dichlorostyryl)-1H-pyrazole, (Z)-3-(2,6-dichlorostyryl)-1H-pyrazole, (E)-3-(2-(naphthalen-2-yl)vinyl)-1H-pyrazole, (Z)-3-(2-(naphthalen-2-yl)vinyl)-1H-pyrazole, (E)-3-(2-(1H-pyrrol-2-yl)vinyl)-1H-pyrazole, (Z)-3-(2-(1H-pyrrol-2-yl)vinyl)-1H-pyrazole, (E)-3-(2-(thiophen-3-yl)vinyl)-1H-pyrazole, (Z)-3-(2-(thiophen-3-yl)vinyl)-1H-pyrazole, (E)-3-(2-(1H-pyrrol-3-yl)vinyl)-1H-pyrazole, (Z)-3-(2-(1H-pyrrol-3-yl)vinyl)-1H-pyrazole, (E)-3-(2-(furan-3-yl)vinyl)-1H-pyrazole, (Z)-3-(2-(furan-3-yl)vinyl)-1H-pyrazole, 3(5)-[2-(phenyl)vinyl]-1-(4-chlorobenzoyl)-1H-pyrazole, (E)-furan-2-yl(3-styryl-1H-pyrazol-1-yl)methanone, (E)-(3-(2, 6-dichlorostyryl)-1H-pyrazol-1-yl)(thiophen-2-yl)methanone, (E)-2-(4-methoxyphenyl)-1-(3-styryl-1H-pyrazol-1-yl)ethanone, (E)-cyclopropyl(3-styryl-1H-pyrazol-1-yl)methanone, (E)-(6-morpholinopyridin-3-yl)(3-styryl-1H-pyrazol-1-yl)methanone, (E)-(3-(2-(furan-2-yl)vinyl)-1H-pyrazol-1-yl)(4-(trifluoromethoxy)phenyl)methanone, (E)-(3-(2-(furan-2-yl)vinyl)-1H-pyrazol-1-yl)(3-(trifluoromethyl)phenyl)methanone, (E)-(3-(2-(furan-2-yl)vinyl)-1H-pyrazol-1-yl)(2-(trifluoromethoxy)phenyl)methanone, (E)-(3-(2-(furan-2-yl)vinyl)-1H-pyrazol-1-yl)(phenyl)methanone, (E)-benzo[d][1,3]dioxol-5-yl(3-(2-(furan-2-yl)vinyl)-1H-pyrazol-1-yl)methanone, (E)-(3-(2-(thiophen-2-yl)vinyl)-1H-pyrazol-1-yl)(4-(trifluoromethoxy)phenyl)methanone, (E)-3-(3-(2-(furan-2-yl)vinyl)-1H-pyrazole-1-carbonyl)benzonitrile, (E)-methyl 4-(3-(2-(thiophen-2-yl)vinyl)-1H-pyrazole-1-carbonyl)benzoate, (E)-(3-(2-(thiophen-2-yl)vinyl)-1H-pyrazol-1-yl)(3-(trifluoromethoxy)phenyl)methanone, (E)-phenyl(3-(2-(thiophen-2-yl)vinyl)-1H-pyrazol-1-yl)methanone, (E)-benzo[d][1,3]dioxol-5-yl(3-(2-(thiophen-2-yl)vinyl)-1H-pyrazol-1-yl)methanone, (E)-3-(3-(2-(thiophen-2-yl)vinyl)-1H-pyrazole-1-carbonyl)benzonitrile, (E)-4-(3-(2-(thiophen-2-yl)vinyl)-1H-pyrazole-1-carbonyl)benzonitrile, (E)-4-(3-(2-(thiophen-2-yl)vinyl)-1H-pyrazole-1-carbonyl)benzoic acid, (E)-cyclohexyl(3-(2-(thiophen-2-yl)vinyl)-1H-pyrazol-1-yl)methanone, (E)-1-(4-(3-(2-(thiophen-2-yl)vinyl)-1H-pyrazole-1-carbonyl)piperidin-1-yl)ethanone, (E)-(3-(2-(furan-2-yl)vinyl)-1H-pyrazol-1-yl)(1-methyl-1H-pyrrol-2-yl)methanone, (E)-2-cyclopentyl-1-(3-(2-(thiophen-2-yl)vinyl)-1H-pyrazol-1-yl)ethanone, (E)-2-(4-chlorophenyl)-1-(3-(2-(thiophen-2-yl)vinyl)-1H-pyrazol-1-yl)ethanone, (E)-(6-chloropyridin-3-yl)(3-(2-(thiophen-2-yl)vinyl)-1H-pyrazol-1-yl)methanone, (E)-3-(3-(2-(1H-pyrrol-2-yl)vinyl)-1H-pyrazol-1-yl)benzonitrile, (E)-3-(3-(2-(furan-3-yl)vinyl)-1H-pyrazole-1-carbonyl)benzonitrile, (E)-3-(3-(2-(1H-pyrrol-3-yl)vinyl)-1H-pyrazole-1-carbonyl)benzonitrile, or (E)-3-(3-(2-(thiophen-3-yl)vinyl)-1H-pyrazole-1-carbonyl)benzonitrile.

12. Solid Dosage Forms.

Solid dosage forms of compounds embodied herein prepared by co-precipitation with manifold provide oral dosage forms with higher oral bioavailability. In one formulation (A), the following steps were followed.

Step 1 Prepare a solution containing 100 mg compound per mL of ethanol
Step 2 Prepare a solution containing 200 mg mannitol per mL of water
Step 3 Mix 10 mL of the compound solution with 25 mL mannitol solution
Step 4 Remove the solvent by lyophilization or roto-evaporation.

The Formulation Contains:
Compound of the invention, 167 mg
Mannitol, 833 mg
Total 1000 mg In another embodiment, mannitol and lactobionic acid are used in exemplary Formulation B.

Step 1 Prepare a solution containing 100 mg compound per mL of ethanol
Step 2 Prepare a solution containing 200 mg mannitol and 40 mg lactobionic acid per mL of water
Step 3 Mix 10 mL of the compound solution with 25 mL mannitol/lactobionic acid solution
Step 4 Remove the solvent by lyophilization or roto-evaporation.

Formulation B Contains:
Compound 143 mg
Lactobionic acid 143 mg
Mannitol 714 mg
Total 1000 mg In another embodiment, a solid dosage form (exemplary Formulation C) is prepared with compound by co-precipitation with mannitol and gluconic acid:

Step 1 Prepare a solution containing 100 mg compound per mL of ethanol
Step 2 Prepare a solution containing 200 mg mannitol and 20 mg gluconic acid per mL of water
Step 3 Mix 10 mL of the compound solution with 25 mL mannitol/gluconic acid solution
Step 4 Remove the solvent by lyophilization or roto-evaporation.

Formulation C Contains:
Compound 154 mg
Gluconic acid 77 mg
Mannitol 769 mg
Total 1000

In another embodiment, a formulation is prepared with mannitol and methanesulfonic acid. To prepare exemplary Formulation D Step 1 Prepare a solution containing 100 mg compound per mL of ethanol
Step 2 Prepare a solution containing 200 mg mannitol and 20 mg methanesulfonic per mL of water
Step 3 Mix 10 mL of the compound solution with 25 mL mannitol/methanesulfonic acid solution
Step 4 Remove the solvent by lyophilization or roto-evaporation.

Formulation D Contains:
Compound 154 mg
Methanesulfonic acid 77 mg
Mannitol 769 mg
Total 1000

In yet another embodiment, a solid formulation is prepared using crystalline cellulose and oleic acid (exemplary Formulation E):

Step 1 Prepare a solution containing 100 mg compound and 160 mg oleic acid per mL of ethanol
Step 2 To 10 mL of compound/oleic acid solution, add 5.0 g of microcrystalline cellulose
Step 3 Remove the solvent by lyophilization or roto-evaporation.

Formulation E Contains:
Compound 132 mg
Oleic Acid 211 mg
Microcrystalline cellulose 658 mg
Total 1000

In a further formulation, pregelatinized starch 1500 and oleic acid are used (exemplary Formulation F):

Step 1 Prepare a solution containing 100 mg compound and 160 mg oleic per mL of ethanol
Step 2 To 10 mL of compound/oleic acid solution, add 5.0 g of pregelatinized starch 1500
Step 3 Remove the solvent by lyophilization or roto-evaporation.

Formulation F Contains:
Compound 132 mg
Oleic Acid 211 mg
Pregelatinized starch 1500 658 mg
Total 1000

Compounds useful in the aforementioned solid formulations include but are not limited to (E)-3(5)-[2-(2,3-methylenedioxyphenyl)vinyl]-1H-pyrazole, (Z)-3(5)-[2-(2,3-methylenedioxyphenyl)vinyl]-1H-pyrazole, (E)-3(5)-[2-(2-chloro-5-trifluoromethylphenyl)vinyl]-1H-pyrazole, (Z)-3

(5)-[2-(2-chloro-5-trifluoromethylphenyl)vinyl]-1H-pyrazole, (E)-3(5)-[2-(2-trifluoromethylphenyl)vinyl]-1H-pyrazole, (Z)-3(5)-[2-(2-trifluoromethylphenyl)vinyl]-1H-pyrazole, (E)-3(5)-[2-(2-furyl)vinyl]-1H-pyrazole, (Z)-3(5)-[2-(2-furyl)vinyl]-1H-pyrazole, (E)-3(5)-[2-(2-thienyl)vinyl]-1H-pyrazole, (Z)-3(5)-[2-(2-thienyl)vinyl]-1H-pyrazole, (E)-3-(2-(5-nitrofuran-2-yl)vinyl)-1H-pyrazole, (Z)-3-(2-(5-nitrofuran-2-yl)vinyl)-1H-pyrazole, (E)-3-styryl-1H-pyrazole, (Z)-3-styryl-1H-pyrazole, (E)-2-(2-(1H-pyrazol-3-yl)vinyl)-1H-indole, (Z)-2-(2-(1H-pyrazol-3-yl)vinyl)-1H-indole, (E)-4-(2-(1H-pyrazol-3-yl)vinyl)-N,N-dimethylaniline, (Z)-4-(2-(1H-pyrazol-3-yl)vinyl)-N,N-dimethylaniline, (E)-3-(4-methoxystyryl)-1H-pyrazole, (Z)-3-(4-methoxystyryl)-1H-pyrazole, (E)-3-(2,6-dichlorostyryl)-1H-pyrazole, (Z)-3-(2,6-dichiorostyryl)-1H-pyrazole, (E)-3-(2-(naphthalen-2-yl)vinyl)-1H-pyrazole, (Z)-3-(2-(naphthalen-2-yl)vinyl)-1H-pyrazole, (E)-3-(2-(1H-pyrrol-2-yl)vinyl)-1H-pyrazole, (Z)-3-(2-(1H-pyrrol-2-yl)vinyl)-1H-pyrazole, (E)-3-(2-(thiophen-3-yl)vinyl)-1H-pyrazole, (Z)-3-(2-(thiophen-3-yl)vinyl)-1H-pyrazole, (E)-3-(2-(1H-pyrrol-3-yl)vinyl)-1H-pyrazole, (Z)-3-(2-(1H-pyrrol-3-yl)vinyl)-1H-pyrazole, (E)-3-(2-(furan-3-yl)vinyl)-1H-pyrazole, (Z)-3-(2-(furan-3-yl)vinyl)-1H-pyrazole, 3(5)-[2-(phenyl)vinyl]-1-(4-chlorobenzoyl)-1H-pyrazole, (E)-furan-2-yl(3-styryl-1H-pyrazol-1-yl)methanone, (E)-(3-(2,6-dichiorostyryl)-1H-pyrazol-1-yl)(thiophen-2-yl) methanone, (E)-2-(4-methoxyphenyl)-1-(3-styryl-1H-pyrazol-1-yl)ethanone, (E)-cyclopropyl(3-styryl-1H-pyrazol-1-yl)methanone, (E)-(6-morpholinopyridin-3-yl)(3-styryl-1H-pyrazol-1-yl)methanone, (E)-(3-(2-(furan-2-yl) vinyl)-1H-pyrazol-1-yl)(4-(trifluoromethoxy)phenyl) methanone, (E)-(3-(2-(furan-2-yl)vinyl)-1H-pyrazol-1-yl) (3-(trifluoromethoxy)phenyl)methanone, (E)-(3-(2-(furan-2-yl)vinyl)-1H-pyrazol-1-yl)(2-(trifluoromethoxy)phenyl) methanone, (E)-(3-(2-(furan-2-yl)vinyl)-1H-pyrazol-1-yl) (phenyl)methanone, (E)-benzo[d][1,3]dioxol-5-yl(3-(2-(furan-2-yl)vinyl)-1H-pyrazol-1-yl)methanone, (E)-(3-(2-(thiophen-2-yl)vinyl)-1H-pyrazol-1-yl)(4-(trifluoromethoxy)phenyl)methanone, (E)-3-(3-(2-(furan-2-yl)vinyl)-1H-pyrazole-1-carbonyl)benzonitrile, (E)-methyl 4-(3-(2-(thiophen-2-yl)vinyl)-1H-pyrazole-1-carbonyl)benzoate, (E)-(3-(2-(thiophen-2-yl)vinyl)-1H-pyrazol-1-yl)(3-(trifluoromethoxy)phenyl)methanone, (E)-phenyl(3-(2-(thiophen-2-yl)vinyl)-1H-pyrazol-1-yl)methanone, (E)-benzo[d][1,3]dioxol-5-yl(3-(2-(thiophen-2-yl)vinyl)-1H-pyrazol-1-yl)methanone, (E)-3-(3-(2-(thiophen-2-yl)vinyl)-1H-pyrazole-1-carbonyl)benzonitrile, (E)-4-(3-(2-(thiophen-2-yl)vinyl)-1H-pyrazole-1-carbonyl)benzonitrile, (E)-4-(3-(2-(thiophen-2-yl)vinyl)-1H-pyrazole-1-carbonyl) benzoic acid, (E)-cyclohexyl(3-(2-(thiophen-2-yl)vinyl)-1H-pyrazol-1-yl)methanone, (E)-1-(4-(3-(2-(thiophen-2-yl) vinyl)-1H-pyrazole-1-carbonyl)piperidin-1-yl)ethanone, (E)-(3-(2-(furan-2-yl)vinyl)-1H-pyrazol-1-yl)(1-methyl-1H-pyrrol-2-yl)methanone, (E)-2-cyclopentyl-1-(3-(2-(thiophen-2-yl)vinyl)-1H-pyrazol-1-yl)ethanone, (E)-2-(4-chiorophenyl)-1-(3-(2-(thiophen-2-yl)vinyl)-1H-pyrazol-1-yl) ethanone, (E)-(6-chloropyridin-3-yl)(3-(2-(thiophen-2-yl) vinyl)-1H-pyrazol-1-yl)methanone, (E)-3-(3-(2-(1H-pyrrol-2-yl)vinyl)-1H-pyrazol-1-yl)benzonitrile, (E)-3-(3-(2-(furan-3-yl)vinyl)-1H-pyrazole-1-carbonyl)benzonitrile, (E)-3-(3-(2-(1H-pyrrol-3-yl)vinyl)-1H-pyrazole-1-carbonyl)benzonitrile, or (E)-3-(3-(2-(thiophen-3-yl)vinyl)-1H-pyrazole-1-carbonyl)benzonitrile.

In another embodiment, any of the aforementioned compounds can be formulated in a solid dosage form in hard gelatin capsules with one of the dosage size formulations mentioned below:

250 mg Active Capsule:

| | |
|---|---|
| Compound | 250.0 mg |
| Microcrystalline Cellulose NF (Avicel PH102) | 113.9 mg |
| Sodium Croscarmellose, NF (Ac-Di-Sol) | 20.0 mg |
| Sodium Lauryl Sulfate, NF | 0.8 mg |
| Magnesium Stearate, NF | 2.0 mg |
| Hard Gelatin Capsule Shell, Size 0 | 1 Unit |

50 mg Active Capsule:

| | |
|---|---|
| Compound | 50.0 mg |
| Microcrystalline Cellulose NF (Avicel PH102) | 165.6 mg |
| Sodium Croscarmellose, NF (Ac-Di-Sol) | 12.0 mg |
| Sodium Lauryl Sulfate, NF | 0.5 mg |
| Magnesium Stearate, NF | 1.2 mg |
| Hard Gelatin Capsule Shell, Size 1 | 1 Unit |

10 mg Active Capsule:

| | |
|---|---|
| Compound | 10.0 mg |
| Microcrystalline Cellulose NF (Avicel PH102) | 159.5 mg |
| Sodium Croscarmellose, NF (Ac-Di-Sol) | 9.0 mg |
| Sodium Lauryl Sulfate, NF | 0.4 mg |
| Magnesium Stearate, NF | 1.0 mg |
| Hard Gelatin Capsule Shell, Size 2 | 1 Unit |

What is claimed is:

1. A method of preparing a pharmaceutical composition comprising a compound (E)-3-[2-(2-thienyl)vinyl]-1H-pyrazole, or a tautomer thereof, or a pharmaceutically acceptable salt thereof,
   the method comprising (i) providing the compound or a tautomer thereof or a pharmaceutically acceptable salt thereof; and (ii) formulating the compound or a tautomer thereof or a pharmaceutically acceptable salt thereof in aqueous buffered saline comprising about 40% to about 60% (v/v) polyethylene glycol 300 and about 5% to about 15% (v/v) polysorbate 80.

2. The method of claim 1, wherein the pharmaceutical composition is an injectable pharmaceutical composition.

3. The method of claim 2, wherein the injectable pharmaceutical composition is sterile.

4. The method of claim 1, wherein the pharmaceutical composition comprises about 50% (v/v) polyethylene glycol 300.

5. The method of claim 4, wherein the pharmaceutical composition comprises about 10% (v/v) polysorbate 80.

6. The method of claim 5, wherein the pharmaceutical composition comprises about 0.8 mg/mL to about 10 mg/mL of the compound.

7. The method of claim 6, wherein the aqueous buffered saline is phosphate-buffered saline.

8. The method of claim 7, wherein the pH of the pharmaceutical composition is about 7.4.

9. The method of claim 1, wherein the pharmaceutical composition comprises about 10% (v/v) polysorbate 80.

10. The method of claim 1, wherein the pharmaceutical composition comprises about 0.8 mg/mL to about 10 mg/mL of the compound.

11. The method of claim 1, wherein the aqueous buffered saline is phosphate-buffered saline.

12. The method of claim 1, wherein the pH of the pharmaceutical composition is about 7.4.

13. A method of preparing a pharmaceutical composition comprising a compound (E)-3-[2-(2-thienyl)vinyl]-1H-pyrazole or a tautomer thereof,
the method comprising (i) providing the compound or a tautomer thereof; and (ii) formulating the compound or a tautomer thereof in aqueous buffered saline comprising about 40% to about 60% (v/v) polyethylene glycol 300 and about 5% to about 15% (v/v) polysorbate 80.

14. The method of claim 13, wherein the pharmaceutical composition is an injectable pharmaceutical composition.

15. The method of claim 14, wherein the injectable pharmaceutical composition is sterile.

16. The method of claim 13, wherein the pharmaceutical composition comprises about 50% (v/v) polyethylene glycol 300.

17. The method of claim 16, wherein the pharmaceutical composition comprises about 10% (v/v) polysorbate 80.

18. The method of claim 17, wherein the pharmaceutical composition comprises about 0.8 mg/mL to about 10 mg/mL of the compound.

19. The method of claim 18, wherein the aqueous buffered saline is phosphate-buffered saline.

20. The method of claim 19, wherein the pH of the pharmaceutical composition is about 7.4.

21. The method of claim 13, wherein the pharmaceutical composition comprises about 10% (v/v) polysorbate 80.

22. The method of claim 13, wherein the pharmaceutical composition comprises about 0.8 mg/mL to about 10 mg/mL of the compound.

23. The method of claim 13, wherein the aqueous buffered saline is phosphate-buffered saline.

24. The method of claim 13, wherein the pH of the pharmaceutical composition is about 7.4.

* * * * *